US012760086B2

(12) United States Patent
Jung et al.

(10) Patent No.: US 12,760,086 B2
(45) Date of Patent: Oct. 13, 2026

(54) PD-1 VARIANT HAVING IMPROVED BINDING ABILITY TO PD-L1

(71) Applicant: ELISIGEN INC., Seoul (KR)

(72) Inventors: Sang Taek Jung, Gyeonggi-do (KR); Kwang-Jin Chun, Seoul (KR); Ji Yeon Ha, Seoul (KR)

(73) Assignee: ELISIGEN INC., Seoul (KR)

( * ) Notice: Subject to any disclaimer, the term of this patent is extended or adjusted under 35 U.S.C. 154(b) by 1034 days.

(21) Appl. No.: 16/966,656

(22) PCT Filed: Jan. 30, 2019

(86) PCT No.: PCT/KR2019/001290
§ 371 (c)(1),
(2) Date: Jul. 31, 2020

(87) PCT Pub. No.: WO2019/151771
PCT Pub. Date: Aug. 8, 2019

(65) Prior Publication Data

US 2023/0002472 A1 Jan. 5, 2023

(30) Foreign Application Priority Data

Feb. 2, 2018 (KR) ........................ 10-2018-0013381
Jan. 29, 2019 (KR) ........................ 10-2019-0011181

(51) Int. Cl.
*A61P 37/02* (2006.01)
*A61P 35/00* (2006.01)
(Continued)

(52) U.S. Cl.
CPC ........ *C07K 14/70532* (2013.01); *A61P 35/00* (2018.01); *C12N 15/85* (2013.01)

(58) Field of Classification Search
CPC .......................... C07K 14/70532; C12N 15/85
See application file for complete search history.

(56) References Cited

U.S. PATENT DOCUMENTS

2009/0305950 A1 12/2009 Minato
2015/0203579 A1 7/2015 Papadopoulos
(Continued)

FOREIGN PATENT DOCUMENTS

EP 2638061 B1 4/2015
EP 3097119 A1 * 11/2016 ......... A61K 39/3955
(Continued)

OTHER PUBLICATIONS

Appendix A—Alignment SEQ ID 61 C69S and SEQ ID 351 (Year: 2023).*

(Continued)

*Primary Examiner* — Thane Underdahl
*Assistant Examiner* — Mary A Crum
(74) *Attorney, Agent, or Firm* — DUANE MORRIS LLP; Gregory M. Lefkowitz; Brandon A. Chan

(57) ABSTRACT

A PD-1 variant, which has improved binding affinity to PD-L1, and methods for preparing and screening the PD-1 variant. The PD-1 variant of the present disclosure effectively inhibits the binding between wild-type PD-1 and PD-L1, and thus is expected to have significantly higher penetration ability and anticancer effect by immune cells or therapeutic effect for infectious diseases as compared to existing immune checkpoint inhibitors. At the same time, the possibility of immunogenicity can be minimized. In addition, the convenience of developing biomedicine may be promoted through aglycosylation.

14 Claims, 17 Drawing Sheets

Specification includes a Sequence Listing.

(51) Int. Cl.
*C07K 14/705* (2006.01)
*C12N 15/85* (2006.01)

(56) References Cited

U.S. PATENT DOCUMENTS

| | | | | |
|---|---|---|---|---|
| 2016/0039903 | A1 | 2/2016 | Ring | |
| 2016/0340397 | A1 | 11/2016 | Ring | |
| 2017/0095531 | A1 * | 4/2017 | Schreiber | A61P 37/02 |
| 2018/0125934 | A1 | 5/2018 | Giaccia | |
| 2019/0381184 | A1 | 12/2019 | Huang | |
| 2020/0299353 | A1 | 9/2020 | Berry | |
| 2021/0284711 | A1 | 9/2021 | Pecker | |

FOREIGN PATENT DOCUMENTS

| | | | |
|---|---|---|---|
| KR | 1020160113113 | 9/2016 | |
| WO | WO-2016164428 A1 * | 10/2016 | A61K 38/1774 |
| WO | 2017/200796 | 11/2017 | |
| WO | 2018/077189 | 5/2018 | |
| WO | 2019/109954 | 6/2019 | |
| WO | 2019/241758 | 12/2019 | |

OTHER PUBLICATIONS

Betts, Matthew J., and Robert B. Russell. "Amino acid properties and consequences of substitutions." Bioinformatics for geneticists (2003): 289-316. (Year: 2003).*

Appendix A Protein alignment of reference SEQ ID No. 1 of Giaccia and instant SEQ ID No. 61, 2023 (Year: 2023).*

University of Arizona, The Biology Project, www.biology.arizona.edu/biochemistry/problem_sets/aa/isoleusine.html, 2003) (Year: 2003).*

University of Arizona, The Biology Project, http://www.biology.arizona.edu/biochemistry/problem_sets/aa/Valine.html, 2003 (Year: 2003).*

Li, Yanyan, et al. "High-affinity PD-1 molecules deliver improved interaction with PD-L1 and PD-L2." Cancer Science 109.8 (2018): 2435-2445 (Year: 2018).*

Appendix B, Protein alignment of reference SEQ ID No. 32 of Giaccia and instant SEQ ID No. 61, 2025 (Year: 2025).*

Mayer, Aaron T., et al. "Practical immuno-PET radiotracer design considerations for human immune checkpoint imaging." Journal of Nuclear Medicine 58.4 (2017): 538-546. (Year: 2017).*

Du, J., et al., "The design of high affinity human PD-1 mutant by using molecular dynamics simulations (MD)," Cell Communication and Signaling, 2018, 16:25.

Zak, K.M., et al., "Structure of the Complex of Human Programmed Death 1, PD-1, and its Ligand PD-L1," Structure, Dec. 2015; 23(12); 2341-2348.

Liu, C., et al., "Soluble PD-1 aggravates progression of collagen-induced arthritis through Th1 and Th17 pathways," Arthritis Research & Therapy (2015) 17:340.

Liang, Z., et al., "High-affinity human PD-L1 variants attenuate the suppression of T cell activation," Oncotarget, 2017, vol. 8, (No. 51), pp. 88360-88375.

Zak, K.M., et al., "Structural Biology of the Immune Checkpoint Receptor PD-1 and its Ligands PD-L1/PD-L2," Structure Review, vol. 25, Issue 8, Aug. 1, 2017, pp. 1163-1174.

* cited by examiner

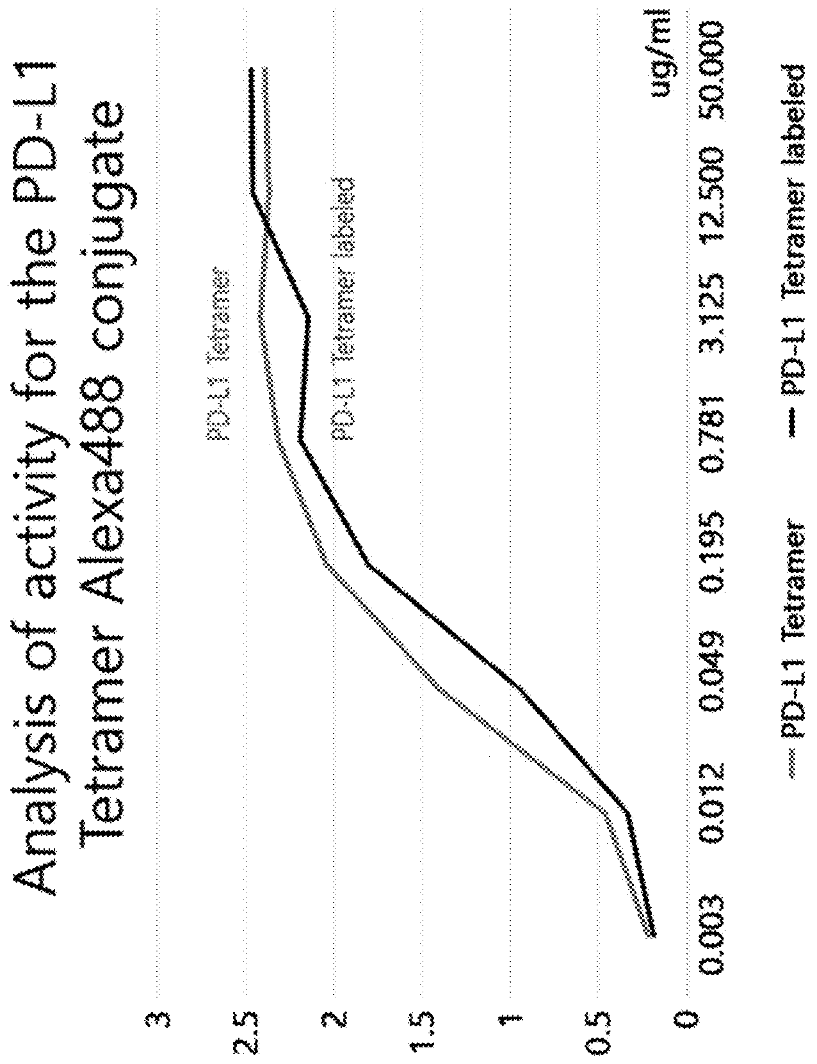
FIG. 3
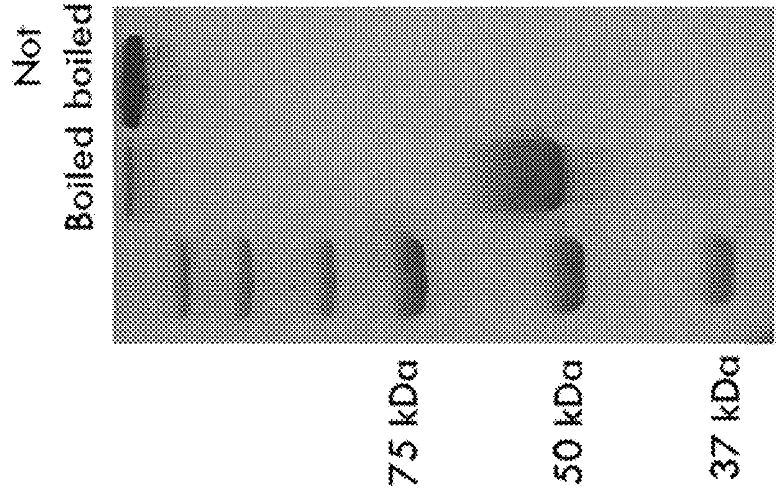

SEQUENCE LISTING

```
<160> NUMBER OF SEQ ID NOS: 95

<210> SEQ ID NO 1
<211> LENGTH: 45
<212> TYPE: DNA
<213> ORGANISM: Artificial Sequence
<220> FEATURE:
<223> OTHER INFORMATION: CKJ#1

<400> SEQUENCE: 1

gcggaattcg gcgcgcactc cgaattagac tccccagaca ggccc                  45


<210> SEQ ID NO 2
<211> LENGTH: 57
<212> TYPE: DNA
<213> ORGANISM: Artificial Sequence
<220> FEATURE:
<223> OTHER INFORMATION: CKJ#2

<400> SEQUENCE: 2

gaattccgct ctagattatc aatgatgatg gtggtgatgt tggaactggc cggctgg      57


<210> SEQ ID NO 3
<211> LENGTH: 41
<212> TYPE: DNA
<213> ORGANISM: Artificial Sequence
<220> FEATURE:
<223> OTHER INFORMATION: CKJ#3
```

```
<400> SEQUENCE: 3

cgtggtgacc gaaggggacg ccgccacctt cacctgcagc t                    41


<210> SEQ ID NO 4
<211> LENGTH: 41
<212> TYPE: DNA
<213> ORGANISM: Artificial Sequence
<220> FEATURE:
<223> OTHER INFORMATION: CKJ#4

<400> SEQUENCE: 4

agctgcaggt gaaggtggcg gcgtcccctt cggtcaccac g                    41


<210> SEQ ID NO 5
<211> LENGTH: 48
<212> TYPE: DNA
<213> ORGANISM: Artificial Sequence
<220> FEATURE:
<223> OTHER INFORMATION: CKJ#5

<400> SEQUENCE: 5

accttcacct gcagcttctc cgccacatcg gagagcttcg tgctaaac             48


<210> SEQ ID NO 6
<211> LENGTH: 48
<212> TYPE: DNA
<213> ORGANISM: Artificial Sequence
<220> FEATURE:
<223> OTHER INFORMATION: CKJ#6

<400> SEQUENCE: 6

gtttagcacg aagctctccg atgtggcgga gaagctgcag gtgaaggt             48


<210> SEQ ID NO 7
<211> LENGTH: 41
<212> TYPE: DNA
<213> ORGANISM: Artificial Sequence
<220> FEATURE:
<223> OTHER INFORMATION: CKJ#7

<400> SEQUENCE: 7

gtaccgcatg agccccagcg cccagacgga caagctggcc g                    41


<210> SEQ ID NO 8
<211> LENGTH: 41
<212> TYPE: DNA
<213> ORGANISM: Artificial Sequence
<220> FEATURE:
<223> OTHER INFORMATION: CKJ#8

<400> SEQUENCE: 8

cggccagctt gtccgtctgg gcgctggggc tcatgcggta c                    41


<210> SEQ ID NO 9
<211> LENGTH: 38
<212> TYPE: DNA
<213> ORGANISM: Artificial Sequence
<220> FEATURE:
<223> OTHER INFORMATION: CKJ#9

<400> SEQUENCE: 9

gtcagggccc ggcgcgccga cagcggcacc tacctctg                        38


<210> SEQ ID NO 10
<211> LENGTH: 38
```

<212> TYPE: DNA
<213> ORGANISM: Artificial Sequence
<220> FEATURE:
<223> OTHER INFORMATION: CKJ#10

<400> SEQUENCE: 10
cagaggtagg tgccgctgtc ggcgcgccgg gccctgac 38

<210> SEQ ID NO 11
<211> LENGTH: 49
<212> TYPE: DNA
<213> ORGANISM: Artificial Sequence
<220> FEATURE:
<223> OTHER INFORMATION: Hw#1

<400> SEQUENCE: 11
gcggaattcg gcgcgcactc cgaatttact gtcacggttc ccaaggacc 49

<210> SEQ ID NO 12
<211> LENGTH: 69
<212> TYPE: DNA
<213> ORGANISM: Artificial Sequence
<220> FEATURE:
<223> OTHER INFORMATION: Hw#2

<400> SEQUENCE: 12
cttgtgcctt gctatcttta gacgggtcag agccaccgcc accccttca tttggaggat 60 gtgccagag 69

<210> SEQ ID NO 13
<211> LENGTH: 28
<212> TYPE: DNA
<213> ORGANISM: Artificial Sequence
<220> FEATURE:
<223> OTHER INFORMATION: Hw#3

<400> SEQUENCE: 13
gacccgtcta aagatagcaa ggcacaag 28

<210> SEQ ID NO 14
<211> LENGTH: 41
<212> TYPE: DNA
<213> ORGANISM: Artificial Sequence
<220> FEATURE:
<223> OTHER INFORMATION: Hw#4

<400> SEQUENCE: 14
gaattccgct ctagatcatt agtggtgatg atggtggtga g 41

<210> SEQ ID NO 15
<211> LENGTH: 42
<212> TYPE: DNA
<213> ORGANISM: Artificial Sequence
<220> FEATURE:
<223> OTHER INFORMATION: JY#1

<400> SEQUENCE: 15
cgcagcgagg cccagccggc cttagactcc ccagacaggc cc 42

<210> SEQ ID NO 16
<211> LENGTH: 41
<212> TYPE: DNA
<213> ORGANISM: Artificial Sequence
<220> FEATURE:
<223> OTHER INFORMATION: JY#2

<400> SEQUENCE: 16
cgcagcgagg cccccgaggc cccttggaac tggccggctg g 41

<210> SEQ ID NO 17
<211> LENGTH: 21
<212> TYPE: DNA
<213> ORGANISM: Artificial Sequence
<220> FEATURE:
<223> OTHER INFORMATION: JY#3

<400> SEQUENCE: 17
cgcagcgagg cccagccggc c 21

<210> SEQ ID NO 18
<211> LENGTH: 23
<212> TYPE: DNA
<213> ORGANISM: Artificial Sequence
<220> FEATURE:
<223> OTHER INFORMATION: JY#4

<400> SEQUENCE: 18
cgcagcgagg cccccgaggc ccc 23

<210> SEQ ID NO 19
<211> LENGTH: 447
<212> TYPE: DNA
<213> ORGANISM: Artificial Sequence
<220> FEATURE:
<223> OTHER INFORMATION: pMaz-Wild type PD-1-His tag DNA sequence

<400> SEQUENCE: 19
ttagactccc cagacaggcc ctggaacccc cccaccttct ccccagccct gctcgtggtg 60
accgaagggg acaacgccac cttcacctgc agcttctcca acacatcgga gagcttcgtg 120
ctaaactggt accgcatgag ccccagcaac cagacggaca agctggccgc cttccccgag 180
gaccgcagcc agcccggcca ggactgccgc ttccgtgtca cacaactgcc caacgggcgt 240
gacttccaca tgagcgtggt cagggcccgg cgcaatgaca gcggcaccta cctctgtggg 300
gccatctccc tggcccccaa ggcgcagatc aaagagagcc tgcgggcaga gctcagggtg 360
acagagagaa gggcagaagt gcccacagcc caccccagcc cctcacccag gccagccggc 420
cagttccaac atcaccacca tcatcat 447

<210> SEQ ID NO 20
<211> LENGTH: 447
<212> TYPE: DNA
<213> ORGANISM: Artificial Sequence
<220> FEATURE:
<223> OTHER INFORMATION: pMaz-N25A PD-1-His tag DNA sequence

<400> SEQUENCE: 20
ttagactccc cagacaggcc ctggaacccc cccaccttct ccccagccct gctcgtggtg 60
accgaagggg acgccgccac cttcacctgc agcttctcca acacatcgga gagcttcgtg 120
ctaaactggt accgcatgag ccccagcaac cagacggaca agctggccgc cttccccgag 180
gaccgcagcc agcccggcca ggactgccgc ttccgtgtca cacaactgcc caacgggcgt 240
gacttccaca tgagcgtggt cagggcccgg cgcaatgaca gcggcaccta cctctgtggg 300
gccatctccc tggcccccaa ggcgcagatc aaagagagcc tgcgggcaga gctcagggtg 360
acagagagaa gggcagaagt gcccacagcc caccccagcc cctcacccag gccagccggc 420
cagttccaac atcaccacca tcatcat 447

<210> SEQ ID NO 21
<211> LENGTH: 447
<212> TYPE: DNA
<213> ORGANISM: Artificial Sequence
<220> FEATURE:
<223> OTHER INFORMATION: pMaz-N34A PD-1-His tag DNA sequence

<400> SEQUENCE: 21
ttagactccc cagacaggcc ctggaacccc cccaccttct ccccagccct gctcgtggtg 60
accgaagggg acaacgccac cttcacctgc agcttctccg ccacatcgga gagcttcgtg 120
ctaaactggt accgcatgag ccccagcaac cagacggaca agctggccgc cttccccgag 180
gaccgcagcc agcccggcca ggactgccgc ttccgtgtca cacaactgcc caacgggcgt 240
gacttccaca tgagcgtggt cagggcccgg cgcaatgaca gcggcaccta cctctgtggg 300
gccatctccc tggcccccaa ggcgcagatc aaagagagcc tgcgggcaga gctcagggtg 360
acagagagaa gggcagaagt gcccacagcc caccccagcc cctcacccag gccagccggc 420
cagttccaac atcaccacca tcatcat 447

<210> SEQ ID NO 22
<211> LENGTH: 447
<212> TYPE: DNA
<213> ORGANISM: Artificial Sequence
<220> FEATURE:
<223> OTHER INFORMATION: pMaz-N50A PD-1-His tag DNA sequence

<400> SEQUENCE: 22
ttagactccc cagacaggcc ctggaacccc cccaccttct ccccagccct gctcgtggtg 60
accgaagggg acaacgccac cttcacctgc agcttctcca acacatcgga gagcttcgtg 120
ctaaactggt accgcatgag ccccagcgcc cagacggaca agctggccgc cttccccgag 180
gaccgcagcc agcccggcca ggactgccgc ttccgtgtca cacaactgcc caacgggcgt 240
gacttccaca tgagcgtggt cagggcccgg cgcaatgaca gcggcaccta cctctgtggg 300
gccatctccc tggcccccaa ggcgcagatc aaagagagcc tgcgggcaga gctcagggtg 360
acagagagaa gggcagaagt gcccacagcc caccccagcc cctcacccag gccagccggc 420
cagttccaac atcaccacca tcatcat 447

<210> SEQ ID NO 23
<211> LENGTH: 447
<212> TYPE: DNA
<213> ORGANISM: Artificial Sequence
<220> FEATURE:
<223> OTHER INFORMATION: pMaz-N92A PD-1-His tag DNA sequence

<400> SEQUENCE: 23
ttagactccc cagacaggcc ctggaacccc cccaccttct ccccagccct gctcgtggtg 60
accgaagggg acaacgccac cttcacctgc agcttctcca acacatcgga gagcttcgtg 120
ctaaactggt accgcatgag ccccagcaac cagacggaca agctggccgc cttccccgag 180
gaccgcagcc agcccggcca ggactgccgc ttccgtgtca cacaactgcc caacgggcgt 240
gacttccaca tgagcgtggt cagggcccgg cgcgccgaca gcggcaccta cctctgtggg 300
gccatctccc tggcccccaa ggcgcagatc aaagagagcc tgcgggcaga gctcagggtg 360
acagagagaa gggcagaagt gcccacagcc caccccagcc cctcacccag gccagccggc 420
cagttccaac atcaccacca tcatcat 447

<210> SEQ ID NO 24
<211> LENGTH: 1185
<212> TYPE: DNA
<213> ORGANISM: Artificial Sequence
<220> FEATURE:
<223> OTHER INFORMATION: PD-L1-streptavidin DNA sequence

<400> SEQUENCE: 24
tttactgtca cggttcccaa ggacctatat gtggtagagt atggtagcaa tatgacaatt 60
gaatgcaaat tcccagtaga aaaacaatta gacctggctg cactaattgt ctattgggaa 120
atggaggata agaacattat tcaatttgtg catggagagg aagacctgaa ggttcagcat 180
agtagctaca gacagagggc ccggctgttg aaggaccagc tctccctggg aaatgctgca 240
cttcagatca cagatgtgaa attgcaggat gcaggggtgt accgctgcat gatcagctat 300
ggtggtgccg actacaagcg aattactgtg aaagtcaatg ccccatacaa caaaatcaac 360
caaagaattt tggttgtgga tccagtcacc tctgaacatg aactgacatg tcaggctgag 420 ggctaccccca aggccgaagt catctggaca agcagtgacc atcaagtcct gagtggtaag 480
accaccacca ccaattccaa gagagaggag aagcttttca atgtgaccag cacactgaga 540
atcaacacaa caactaatga gattttctac tgcactttta ggagattaga tcctgaggaa 600
aaccatacag ctgaattggt catcccagaa ctacctctgg cacatcctcc aaatgaaagg 660
ggtggcggtg gctctgaccc gtctaaagat agcaaggcac aagtgagcgc ggcagaggcc 720
ggtattaccg gcacctggta caaccaactg ggttctacgt tcattgttac ggccggtgcc 780
gatggtgcat taacgggtac ctacgaatct gcagtcggca acgcggagtc tcgttacgtt 840
ctgacgggcc gttatgattc tgcaccagcc acggacggca gcggcacggc cttaggttgg 900
accgtggcct ggaagaacaa ctatcgcaat gcccacagcg ccacgacctg gtctggccaa 960
tatgtcggcg gtgcggaagc ccgcattaat acccagtggt tactgacgtc tggcaccacg 1020
gaggccaacg catggaaaag caccctggtc ggccatgata ccttcacgaa ggtcaagcca 1080
tctgcggcca gcattgacgc agcaaaaaag gcaggcgtta acaacggcaa cccactggac 1140
gcagtgcagc agggtggcgg tggctctcac caccatcatc accac 1185

<210> SEQ ID NO 25
<211> LENGTH: 600
<212> TYPE: DNA
<213> ORGANISM: Artificial Sequence
<220> FEATURE:
<223> OTHER INFORMATION: NlpA-Wild type PD-1-FLAG DNA sequence

<400> SEQUENCE: 25
atgaaactga caacacatca tctacggaca ggggccgcat tattgctggc cggaattctg 60
ctggcaggtt gcgaccagag tagcagcgag gcccagccgg ccttagactc cccagacagg 120
ccctggaacc cccccacctt ctccccagcc ctgctcgtgg tgaccgaagg ggacaacgcc 180
accttcacct gcagcttctc caacacatcg gagagcttcg tgctaaactg gtaccgcatg 240
agccccagca accagacgga caagctggcc gccttccccg aggaccgcag ccagcccggc 300
caggactgcc gcttccgtgt cacacaactg cccaacgggc gtgacttcca catgagcgtg 360
gtcagggccc ggcgcaatga cagcggcacc tacctctgtg gggccatctc cctggccccc 420
aaggcgcaga tcaaagagag cctgcgggca gagctcaggg tgacagagag aagggcagaa 480
gtgcccacag cccaccccag cccctcaccc aggccagccg gccagttcca aggggcctcg 540
ggggccgaat tcgcggccgc tgcaccagat tataaagatg acgatgacaa agggcgcgcc 600

<210> SEQ ID NO 26
<211> LENGTH: 600
<212> TYPE: DNA
<213> ORGANISM: Artificial Sequence
<220> FEATURE:
<223> OTHER INFORMATION: NlpA- HAC-V PD-1 -FLAG DNA sequence

<400> SEQUENCE: 26
atgaaactga caacacatca tctacggaca ggggccgcat tattgctggc cggaattctg 60
ctggcaggtt gcgaccagag tagcagcgag gcccagccgg ccttagactc cccagacagg 120
ccctggaacc cccccacctt ctccccagcc ctgctcgtgg tgaccgaagg ggacaacgcc 180
accttcacct gcagcttctc caacacatcg gagagcttcc atgttgtttg gcatcgcgaa 240
agccccagcg gccagacgga caccctggcc gccttccccg aggaccgcag ccagcccggc 300
caggactgcc gcttccgtgt cacacaactg cccaacgggc gtgacttcca catgagcgtg 360
gtcagggccc ggcgcaatga cagcggcacc tacgtgtgtg gggtgatctc cctggccccc 420
aagatccaga tcaaagagag cctgcgggca gagctcaggg tgacagagag aagggcagaa 480
gtgcccacag cccaccccag cccctcaccc aggccagccg gccagttcca aggggcctcg 540
ggggccgaat tcgcggccgc tgcaccagat tataaagatg acgatgacaa agggcgcgcc 600

<210> SEQ ID NO 27
<211> LENGTH: 429
<212> TYPE: DNA
<213> ORGANISM: Artificial Sequence
<220> FEATURE:
<223> OTHER INFORMATION: PD-1 Variants No. 41 DNA sequence

<400> SEQUENCE: 27
ttagactccc cagacaggcc ctggaacccc cccaccttct ccccagccct gctcgtggtg 60
accgaagggg acaacgccac cttcacctgc agcttctcca acacaccgga gagcttcgtg 120
ctaaactggt accgcatgag ccccagcaac cagacggaca agctggccgc cttccccgag 180
gaccgcagcc agcccggcca ggacagccgc ttccgtgtca cacaactgcc caacgggcgt 240
gacttccaca tgagcgtggt cagggcccgg cgcaatgaca gcggcaccta cctctgtggg 300
gccatctccc tggcccccaa ggcgcagatc aaagagagcc cgcgggcaga gctcagggtg 360
acagagagaa gggcagaagt gcccacagcc caccccagcc cctcacccag gccagccggc 420
cagttccaa 429

<210> SEQ ID NO 28
<211> LENGTH: 429
<212> TYPE: DNA
<213> ORGANISM: Artificial Sequence
<220> FEATURE:
<223> OTHER INFORMATION: PD-1 Variants No. 44 DNA sequence

<400> SEQUENCE: 28
ttagactccc cagacaggcc ctggaacccc cccaccatct ccccagccct gctcgtggtg 60
accgaagggg acaacgccac cttcacctgc agcttctcca acacatcgga gagcttcgtg 120
ctaaactggt accgcataag ccccagcagc cagacggaca agctggccgc cttccccgag 180
gaccgcagcc agcccggcca ggactaccgc ttccgtgtca cacaactgcc caacgggcgt 240
gacttccaca tgagcgtggt cagggcccgg cgcaatgaca gcggcaccta cctctgtggg 300
gccatctccc tggcccccaa ggcgcagatc aaagagagcc tgcgggcaga gctcagggtg 360
acagagagaa gggcagaagc gcccacagcc caccccagcc cctcacccag gccagccggc 420
cagttccaa 429

<210> SEQ ID NO 29
<211> LENGTH: 429
<212> TYPE: DNA
<213> ORGANISM: Artificial Sequence
<220> FEATURE:
<223> OTHER INFORMATION: PD-1 Variants No. 45 DNA sequence

<400> SEQUENCE: 29
ttagactccc cagacaggcc ctggaacccc cccaccttct ccccagccct gctcgtggtg 60
accgaagggg acaacgccac cttcacctgc agcttctcca acactccgga gagcttcgtg 120
ctaaactggt accgcatgag ccccagcaac cagacggaca agctggccgc cttccccgag 180
gaccgcagcc agcccggcca ggacagccgc ttccgtgtca cacaactgcc caacgggcgt 240
gacttccaca tgagcgtggt cagggcccgg cgcaatgaca gcggcaccta cctctgtggg 300
gccatctccc tggcccccaa tgcgcagatc aaagagagcc cgcgggcaga gctcagggtg 360
acagagagaa gggcagaagt gcccacagcc caccccagcc cctcacccag gccagccggc 420
cagctccaa 429

<210> SEQ ID NO 30
<211> LENGTH: 429
<212> TYPE: DNA
<213> ORGANISM: Artificial Sequence
<220> FEATURE:
<223> OTHER INFORMATION: PD-1 Variants No. 46 DNA sequence

<400> SEQUENCE: 30
ttagactccc cagacaggcc ctggaacccc cccaccttct ccccagccct gctcgtggtg 60
accgaagggg acaacgccac cttcacctgc agcttctcca acacaccgga gagcttcgtg 120
ctaaactggt accgcatgag ccccagcaac cagacggaca agctggccgc cttccccgag 180
gaccgcagcc agcccggcca ggacagccgc ttccgtgtca cacaactgcc caacgggcgt 240
gacttccaca tgagcgtggt cagggcccgg cgcaatgaca gcggcaccta cctctgtggg 300
gccatctccc tggcccccaa ggcgcagatc aaagagagcc cgcgggcgga gctcagggtg 360
acagagagaa gggcagaagt gcccacagcc cacctcagcc cctcacccag gccagccggc 420
cagttccaa 429

<210> SEQ ID NO 31
<211> LENGTH: 429
<212> TYPE: DNA
<213> ORGANISM: Artificial Sequence
<220> FEATURE:
<223> OTHER INFORMATION: PD-1 Variants No. 49 DNA sequence

<400> SEQUENCE: 31
ttagactccc cagacaggcc ctggaacccc cccaccctct ccccagccct gctcgtggtg 60
accgaagggg acgacgccac cttcacctgc agcttctcca acacatcgga gagcttcgtg 120
ctaaactggt accgcatgag ccccagcaac cagacggaca agctggccgc cttccccgag 180
gaccgcagcc agcccggcca ggactcccgc ttccgtgtca cacaactgcc caacgggcgt 240
gacttccaca tgagcgtggt cagggcccgg cgcagtgaca gcggcaccta cctctgtggg 300
gccatctccc tggcccccaa ggcgcagatc aaagagagcc tgcgggcaga gctcagggtg 360
acagagagaa gggcagaagt gcccacagcc caccccagcc cctcacccaa gccagccggc 420
cagttccaa 429

<210> SEQ ID NO 32
<211> LENGTH: 429
<212> TYPE: DNA
<213> ORGANISM: Artificial Sequence
<220> FEATURE:
<223> OTHER INFORMATION: PD-1 Variants No. 50 DNA sequence

<400> SEQUENCE: 32
ttagactccc cagacaggcc ctggaacccc cccaccctct ccccagccct gctcgtggtg 60
accgaagggg acgacgccac cttcacctgc agcttctcca acacatcgga gagcttcgtg 120
ctaaactggt accgcatgag ccccagcaac cagacggaca agctggccgc cttccccgag 180
gaccgcagcc agcccggcca ggactcccgc ttccgtgtca cacaactgcc caacgggcgt 240
gacttccaca tgagcgtggt caaggcccgg cgcagtgaca gcggcaccta cctctgtggg 300
gccatctccc tggcccccaa ggcgcagatt aaagagagcc tgcgggcaga gctcagggtg 360
acagagagaa ggtcagaagt gcccacagcc caccccagcc cctcacccag gccagccggc 420
cagttccaa 429

<210> SEQ ID NO 33
<211> LENGTH: 429
<212> TYPE: DNA
<213> ORGANISM: Artificial Sequence
<220> FEATURE:
<223> OTHER INFORMATION: PD-1 Variants No. 52 DNA sequence

<400> SEQUENCE: 33
ttagactccc cagacaggcc ctggaacccc cccaccatct ccccagccct gctcgtggtg 60
accgaagggg acaacgccac cttcacctgc agcttctcca acacatcgga gagcttcgtg 120
ctaaactggt accgcataag ccccagcaac cagacggaca agctggccgc cttccccgag 180
gaccgcagcc agcccggcca ggactaccgc ttccgcgtca cacaactgcc caacgggcgt 240
gacttccaca tgagcgtggt cagggcccgg cgcaatgaca gcggcaccta cctctgtggg 300
gccatctccc tggcccccaa ggcgcagatc aaagagagcc tgcgggcaga gctcagggtg 360
acagagagaa gggcagaagt gcccacagcc caccccagcc cctcacccag gccagccggc 420
cagttccaa 429

<210> SEQ ID NO 34
<211> LENGTH: 429
<212> TYPE: DNA
<213> ORGANISM: Artificial Sequence
<220> FEATURE:
<223> OTHER INFORMATION: PD-1 Variants No. 55 DNA sequence

<400> SEQUENCE: 34
ttagactccc cagacaggcc ctggaacccc cccaccttct ccccagccct gctcgtggtg 60
accgaagggg acgacgccac cttcacctgc agcttctcca acacatcgga gagcttcgtg 120
ctaaactggt accgcatgag ccccagcaac cagacggaca agctggccgc cttccccgag 180
gaccgcagcc agcccggcca ggactcccgc ttccgtgtca cacaactgcc caacgggcgt 240
gacttccaca tgagcgtggt cagggcccgg cgcagtgaca gcggcaccta cctctgtggg 300
gtcatctccc tggcccccaa ggcgcagatc aaagagagcc tgcgggcaga gctcagggtg 360
acagagagaa gggcagaagt gcccacagcc caccccagcc cctcacccag gccagccggc 420
cagttccaa 429

<210> SEQ ID NO 35
<211> LENGTH: 429
<212> TYPE: DNA
<213> ORGANISM: Artificial Sequence
<220> FEATURE:
<223> OTHER INFORMATION: PD-1 Variants No. 56 DNA sequence

<400> SEQUENCE: 35
ttagactccc cagacaggcc ctggaacccc cccaccttct ccccagccct gctcgtggtg 60
accgaagggg acaacgccac cttcacctgc agcttctcca acacaccgga gagcttcgtg 120
ctgaactggt accgcatgag ccccagcaac cagacggaca agctggccgc cttccccgag 180
gaccgcagcc agcccggcca ggacagccgc ttccgtgtca cacaactgcc caacgggcgt 240
gacttccaca tgagcgtggt cagggcccgg cgcaaagaca gcggcaccta cctctgtggg 300
gccatctccc tggcccccaa ggcgcagatc aaagagagcc cgcgggcaga gctcagggtg 360
acagagagaa gggcagaagt gcccacagcc cgccccagcc cctcacccag gccagccggc 420
cagttccaa 429

<210> SEQ ID NO 36
<211> LENGTH: 429
<212> TYPE: DNA
<213> ORGANISM: Artificial Sequence
<220> FEATURE:
<223> OTHER INFORMATION: PD-1 Variants No. 66 DNA sequence

<400> SEQUENCE: 36
ttagactccc cagacaggcc ctgggacccc cccaccttct ccccagccct gctcgtggtg 60
accgaagggg acgacgccac cttcacctgc agcttctcca acacatcgga gagcttcgtg 120
ctaaactggt accgcatgag ccccagcaac cagacggaca agctggccgc cttccccgag 180
gaccgcagcc agcccggcca ggactcccgc ttccgtgtca cacaactgcc caacgggcgt 240
gacttccaca tgagcgtggt cagggcccgg cgcagtgaca gcggcaccta cctctgtggg 300
gtcatctccc tggcccccaa ggcgcagatc aaagagagcc tgcgggcaga gctcagggtg 360
acagagagaa gggcagaagt gcccacagcc caccccagcc cctcacccag gccagccggc 420
cagttccaa 429

<210> SEQ ID NO 37
<211> LENGTH: 429
<212> TYPE: DNA
<213> ORGANISM: Artificial Sequence
<220> FEATURE:
<223> OTHER INFORMATION: PD-1 Variants No. 67 DNA sequence

<400> SEQUENCE: 37
ttagactccc cagacaggcc ctggaacccc cccaccttct ccccagccct gctcgtggtg 60
accgaagggg acaacgccac cttcacctgc agcttctcca ccacaccgga gagcttcgtg 120
ctaaactggt accgcatgag ccccagcaac cagacggaca agctggccgc cttccccgag 180
gaccgcagcc agcccggcca ggacagccgc ttccgtgtca cacaactgcc caacgggcgt 240
gacttccaca tgagcgtggt cagggcccgg cgcaatgaca gcggcaccta cctctgtggg 300
gccatctccc tggcccccaa ggcgcagatc aaagagagcc cgcgggcaga gctcagggtg 360
acagagagaa gggcagaagt gcccacagcc caccccagcc cctcacccag gccagccggc 420
cagttccaa 429

<210> SEQ ID NO 38
<211> LENGTH: 429
<212> TYPE: DNA
<213> ORGANISM: Artificial Sequence
<220> FEATURE:
<223> OTHER INFORMATION: PD-1 Variants No. 70 DNA sequence

<400> SEQUENCE: 38
ttagactccc cagacaggcc ctggaacccc cccaccttct ccccagccct gctcgtggta 60
accgaagggg acaacgccac cttcacctgc agcttctcca acacaccgga gagcttcgtg 120
ctaaactggt accgcatgag ccccagcaac cagacggaca agctggccgc cttccccgag 180
gaccgcagcc agcccggcca ggacagccgc ttccgtgtca cacaactgcc caacgggcgt 240
gacttccaca tgagcgtggt cagggcccgg cgcaatgaca gcggcaccta cctctgtggg 300
gccatctccc tggcccccaa ggcgcagatc aaagagagcc tgcgggcaga gctcagggtg 360
acagagagaa gggcagaagt gcccacagcc caccccagcc cctcacccag accagccggc 420
cagttccaa 429

<210> SEQ ID NO 39
<211> LENGTH: 429
<212> TYPE: DNA
<213> ORGANISM: Artificial Sequence
<220> FEATURE:
<223> OTHER INFORMATION: PD-1 Variants No. 78 DNA sequence

<400> SEQUENCE: 39
ttagactccc cagacaggcc ctggaacccc ccctccttct ccccagccct gctcgtggtg 60
accgaagggg acaacgccac cttcacctgc agcttctcca acacaccgga gagcttcgtg 120
ctaaactggt accgcatgag ccccagcaac cagacggaca agctggccgc cttccccgag 180
gaccgcagcc agcccggcca ggacagccgc ttccgtgtca cacaactgcc caacgggcgt 240
gacttccaca tgagcgtggt cagggcccgg cgcaatgaca gcggcaccta cctctgtggg 300
gccatctccc tggcccccaa ggcgcagatc aaagagagcc cgcgggcaga gctcagggtg 360
acagagagaa gggcagaagt gcccacagcc caccccagcc cctcacccag gccagccggc 420
cagttccaa 429

<210> SEQ ID NO 40
<211> LENGTH: 149
<212> TYPE: PRT
<213> ORGANISM: Artificial Sequence
<220> FEATURE:
<223> OTHER INFORMATION: pMaz-Wild type PD-1-His tag Protein sequence

<400> SEQUENCE: 40

Leu Asp Ser Pro Asp Arg Pro Trp Asn Pro Pro Thr Phe Ser Pro Ala
1 5 10 15

Leu Leu Val Val Thr Glu Gly Asp Asn Ala Thr Phe Thr Cys Ser Phe
20 25 30

Ser Asn Thr Ser Glu Ser Phe Val Leu Asn Trp Tyr Arg Met Ser Pro
35 40 45

Ser Asn Gln Thr Asp Lys Leu Ala Ala Phe Pro Glu Asp Arg Ser Gln
50 55 60

Pro Gly Gln Asp Cys Arg Phe Arg Val Thr Gln Leu Pro Asn Gly Arg
65 70 75 80

Asp Phe His Met Ser Val Val Arg Ala Arg Arg Asn Asp Ser Gly Thr

```
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln His
    130                 135                 140

His His His His His
145


<210> SEQ ID NO 41
<211> LENGTH: 149
<212> TYPE: PRT
<213> ORGANISM: Artificial Sequence
<220> FEATURE:
<223> OTHER INFORMATION: pMaz-N25A PD-1-His tag  Protein sequence

<400> SEQUENCE: 41

Leu Asp Ser Pro Asp Arg Pro Trp Asn Pro Pro Thr Phe Ser Pro Ala
1               5                   10                  15

Leu Leu Val Val Thr Glu Gly Asp Ala Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln His
    130                 135                 140

His His His His His
145


<210> SEQ ID NO 42
<211> LENGTH: 149
<212> TYPE: PRT
<213> ORGANISM: Artificial Sequence
<220> FEATURE:
<223> OTHER INFORMATION: pMaz-N34A PD-1-His tag  Protein sequence

<400> SEQUENCE: 42

Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Ala Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80
```

```
Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln His
    130                 135                 140

His His His His His
145


<210> SEQ ID NO 43
<211> LENGTH: 149
<212> TYPE: PRT
<213> ORGANISM: Artificial Sequence
<220> FEATURE:
<223> OTHER INFORMATION: pMaz-N50A PD-1-His tag  Protein sequence

<400> SEQUENCE: 43

Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Ala Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln His
    130                 135                 140

His His His His His
145


<210> SEQ ID NO 44
<211> LENGTH: 149
<212> TYPE: PRT
<213> ORGANISM: Artificial Sequence
<220> FEATURE:
<223> OTHER INFORMATION: pMaz-N92A PD-1-His tag  Protein sequence

<400> SEQUENCE: 44

Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80
```

```
Asp Phe His Met Ser Val Val Arg Ala Arg Arg Ala Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln His
    130                 135                 140

His His His His His
145


<210> SEQ ID NO 45
<211> LENGTH: 395
<212> TYPE: PRT
<213> ORGANISM: Artificial Sequence
<220> FEATURE:
<223> OTHER INFORMATION: PD-L1-streptavidin  Protein sequence

<400> SEQUENCE: 45

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Gly Gly Gly Gly
    210                 215                 220

Ser Asp Pro Ser Lys Asp Ser Lys Ala Gln Val Ser Ala Ala Glu Ala
225                 230                 235                 240

Gly Ile Thr Gly Thr Trp Tyr Asn Gln Leu Gly Ser Thr Phe Ile Val
                245                 250                 255

Thr Ala Gly Ala Asp Gly Ala Leu Thr Gly Thr Tyr Glu Ser Ala Val
            260                 265                 270

Gly Asn Ala Glu Ser Arg Tyr Val Leu Thr Gly Arg Tyr Asp Ser Ala
        275                 280                 285
```

```
Pro Ala Thr Asp Gly Ser Gly Thr Ala Leu Gly Trp Thr Val Ala Trp
    290                 295                 300

Lys Asn Asn Tyr Arg Asn Ala His Ser Ala Thr Thr Trp Ser Gly Gln
305                 310                 315                 320

Tyr Val Gly Gly Ala Glu Ala Arg Ile Asn Thr Gln Trp Leu Leu Thr
                325                 330                 335

Ser Gly Thr Thr Glu Ala Asn Ala Trp Lys Ser Thr Leu Val Gly His
            340                 345                 350

Asp Thr Phe Thr Lys Val Lys Pro Ser Ala Ala Ser Ile Asp Ala Ala
        355                 360                 365

Lys Lys Ala Gly Val Asn Asn Gly Asn Pro Leu Asp Ala Val Gln Gln
    370                 375                 380

Gly Gly Gly Gly Ser His His His His His His
385                 390                 395


<210> SEQ ID NO 46
<211> LENGTH: 200
<212> TYPE: PRT
<213> ORGANISM: Artificial Sequence
<220> FEATURE:
<223> OTHER INFORMATION: NlpA-Wild type PD-1-FLAG  Protein sequence

<400> SEQUENCE: 46

Met Lys Leu Thr Thr His His Leu Arg Thr Gly Ala Ala Leu Leu Leu
1               5                   10                  15

Ala Gly Ile Leu Leu Ala Gly Cys Asp Gln Ser Ser Ser Glu Ala Gln
            20                  25                  30

Pro Ala Leu Asp Ser Pro Asp Arg Pro Trp Asn Pro Pro Thr Phe Ser
        35                  40                  45

Pro Ala Leu Leu Val Val Thr Glu Gly Asp Asn Ala Thr Phe Thr Cys
    50                  55                  60

Ser Phe Ser Asn Thr Ser Glu Ser Phe Val Leu Asn Trp Tyr Arg Met
65                  70                  75                  80

Ser Pro Ser Asn Gln Thr Asp Lys Leu Ala Ala Phe Pro Glu Asp Arg
                85                  90                  95

Ser Gln Pro Gly Gln Asp Cys Arg Phe Arg Val Thr Gln Leu Pro Asn
            100                 105                 110

Gly Arg Asp Phe His Met Ser Val Val Arg Ala Arg Arg Asn Asp Ser
        115                 120                 125

Gly Thr Tyr Leu Cys Gly Ala Ile Ser Leu Ala Pro Lys Ala Gln Ile
    130                 135                 140

Lys Glu Ser Leu Arg Ala Glu Leu Arg Val Thr Glu Arg Arg Ala Glu
145                 150                 155                 160

Val Pro Thr Ala His Pro Ser Pro Ser Pro Arg Pro Ala Gly Gln Phe
                165                 170                 175

Gln Gly Ala Ser Gly Ala Glu Phe Ala Ala Ala Ala Pro Asp Tyr Lys
            180                 185                 190

Asp Asp Asp Asp Lys Gly Arg Ala
        195                 200


<210> SEQ ID NO 47
<211> LENGTH: 200
<212> TYPE: PRT
<213> ORGANISM: Artificial Sequence
<220> FEATURE:
<223> OTHER INFORMATION: NlpA- HAC-V PD-1 -FLAG  Protein sequence
```

<400> SEQUENCE: 47

Met Lys Leu Thr Thr His His Leu Arg Thr Gly Ala Ala Leu Leu Leu
1 5 10 15

Ala Gly Ile Leu Leu Ala Gly Cys Asp Gln Ser Ser Ser Glu Ala Gln
20 25 30

Pro Ala Leu Asp Ser Pro Asp Arg Pro Trp Asn Pro Pro Thr Phe Ser
35 40 45

Pro Ala Leu Leu Val Val Thr Glu Gly Asp Asn Ala Thr Phe Thr Cys
50 55 60

Ser Phe Ser Asn Thr Ser Glu Ser Phe His Val Val Trp His Arg Glu
65 70 75 80

Ser Pro Ser Gly Gln Thr Asp Thr Leu Ala Ala Phe Pro Glu Asp Arg
85 90 95

Ser Gln Pro Gly Gln Asp Cys Arg Phe Arg Val Thr Gln Leu Pro Asn
100 105 110

Gly Arg Asp Phe His Met Ser Val Val Arg Ala Arg Arg Asn Asp Ser
115 120 125

Gly Thr Tyr Val Cys Gly Val Ile Ser Leu Ala Pro Lys Ile Gln Ile
130 135 140

Lys Glu Ser Leu Arg Ala Glu Leu Arg Val Thr Glu Arg Arg Ala Glu
145 150 155 160

Val Pro Thr Ala His Pro Ser Pro Ser Pro Arg Pro Ala Gly Gln Phe
165 170 175

Gln Gly Ala Ser Gly Ala Glu Phe Ala Ala Ala Ala Pro Asp Tyr Lys
180 185 190

Asp Asp Asp Asp Lys Gly Arg Ala
195 200

<210> SEQ ID NO 48
<211> LENGTH: 143
<212> TYPE: PRT
<213> ORGANISM: Artificial Sequence
<220> FEATURE:
<223> OTHER INFORMATION: PD-1 Variants No. 41 Protein sequence

<400> SEQUENCE: 48

Leu Asp Ser Pro Asp Arg Pro Trp Asn Pro Pro Thr Phe Ser Pro Ala
1 5 10 15

Leu Leu Val Val Thr Glu Gly Asp Asn Ala Thr Phe Thr Cys Ser Phe
20 25 30

Ser Asn Thr Pro Glu Ser Phe Val Leu Asn Trp Tyr Arg Met Ser Pro
35 40 45

Ser Asn Gln Thr Asp Lys Leu Ala Ala Phe Pro Glu Asp Arg Ser Gln
50 55 60

Pro Gly Gln Asp Ser Arg Phe Arg Val Thr Gln Leu Pro Asn Gly Arg
65 70 75 80

Asp Phe His Met Ser Val Val Arg Ala Arg Arg Asn Asp Ser Gly Thr
85 90 95

Tyr Leu Cys Gly Ala Ile Ser Leu Ala Pro Lys Ala Gln Ile Lys Glu
100 105 110

Ser Pro Arg Ala Glu Leu Arg Val Thr Glu Arg Arg Ala Glu Val Pro
115 120 125

Thr Ala His Pro Ser Pro Ser Pro Arg Pro Ala Gly Gln Phe Gln
130 135 140

<210> SEQ ID NO 49
<211> LENGTH: 143
<212> TYPE: PRT
<213> ORGANISM: Artificial Sequence
<220> FEATURE:
<223> OTHER INFORMATION: PD-1 Variants No. 44 Protein sequence

<400> SEQUENCE: 49

```
Leu Asp Ser Pro Asp Arg Pro Trp Asn Pro Pro Thr Ile Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Ile Ser Pro
        35                  40                  45

Ser Ser Gln Thr Asp Lys Leu Ala Ala Phe Pro Glu Asp Arg Ser Gln
    50                  55                  60

Pro Gly Gln Asp Tyr Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Ala Pro
        115                 120                 125

Thr Ala His Pro Ser Pro Ser Pro Arg Pro Ala Gly Gln Phe Gln
    130                 135                 140
```

<210> SEQ ID NO 50
<211> LENGTH: 143
<212> TYPE: PRT
<213> ORGANISM: Artificial Sequence
<220> FEATURE:
<223> OTHER INFORMATION: PD-1 Variants No. 45 Protein sequence

<400> SEQUENCE: 50

```
Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Pro Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Ser Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Asn Ala Gln Ile Lys Glu
            100                 105                 110

Ser Pro Arg Ala Glu Leu Arg Val Thr Glu Arg Arg Ala Glu Val Pro
        115                 120                 125

Thr Ala His Pro Ser Pro Ser Pro Arg Pro Ala Gly Gln Leu Gln
    130                 135                 140
```

<210> SEQ ID NO 51
<211> LENGTH: 143
<212> TYPE: PRT
<213> ORGANISM: Artificial Sequence
<220> FEATURE:

<223> OTHER INFORMATION: PD-1 Variants No. 46 Protein sequence

<400> SEQUENCE: 51

```
Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Pro Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Ser Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Pro Arg Ala Glu Leu Arg Val Thr Glu Arg Arg Ala Glu Val Pro
        115                 120                 125

Thr Ala His Leu Ser Pro Ser Pro Arg Pro Ala Gly Gln Phe Gln
    130                 135                 140
```

<210> SEQ ID NO 52
<211> LENGTH: 143
<212> TYPE: PRT
<213> ORGANISM: Artificial Sequence
<220> FEATURE:
<223> OTHER INFORMATION: PD-1 Variants No. 49 Protein sequence

<400> SEQUENCE: 52

```
Leu Asp Ser Pro Asp Arg Pro Trp Asn Pro Pro Thr Leu Ser Pro Ala
1               5                   10                  15

Leu Leu Val Val Thr Glu Gly Asp Asp Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Ser Arg Phe Arg Val Thr Gln Leu Pro Asn Gly Arg
65                  70                  75                  80

Asp Phe His Met Ser Val Val Arg Ala Arg Arg Ser Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Lys Pro Ala Gly Gln Phe Gln
    130                 135                 140
```

<210> SEQ ID NO 53
<211> LENGTH: 143
<212> TYPE: PRT
<213> ORGANISM: Artificial Sequence
<220> FEATURE:
<223> OTHER INFORMATION: PD-1 Variants No. 50 Protein sequence

<400> SEQUENCE: 53

```
Leu Asp Ser Pro Asp Arg Pro Trp Asn Pro Pro Thr Leu Ser Pro Ala
```

1               5                   10                  15

Leu Leu Val Val Thr Glu Gly Asp Asp Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Ser Arg Phe Arg Val Thr Gln Leu Pro Asn Gly Arg
65                  70                  75                  80

Asp Phe His Met Ser Val Val Lys Ala Arg Arg Ser Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ser Glu Val Pro
        115                 120                 125

Thr Ala His Pro Ser Pro Ser Pro Arg Pro Ala Gly Gln Phe Gln
    130                 135                 140

<210> SEQ ID NO 54
<211> LENGTH: 143
<212> TYPE: PRT
<213> ORGANISM: Artificial Sequence
<220> FEATURE:
<223> OTHER INFORMATION: PD-1 Variants No. 52 Protein sequence

<400> SEQUENCE: 54

Leu Asp Ser Pro Asp Arg Pro Trp Asn Pro Pro Thr Ile Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Ile Ser Pro
        35                  40                  45

Ser Asn Gln Thr Asp Lys Leu Ala Ala Phe Pro Glu Asp Arg Ser Gln
    50                  55                  60

Pro Gly Gln Asp Tyr Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln
    130                 135                 140

<210> SEQ ID NO 55
<211> LENGTH: 143
<212> TYPE: PRT
<213> ORGANISM: Artificial Sequence
<220> FEATURE:
<223> OTHER INFORMATION: PD-1 Variants No. 55 Protein sequence

<400> SEQUENCE: 55

Leu Asp Ser Pro Asp Arg Pro Trp Asn Pro Pro Thr Phe Ser Pro Ala
1               5                   10                  15

Leu Leu Val Val Thr Glu Gly Asp Asp Ala Thr Phe Thr Cys Ser Phe
            20                  25                  30

Ser Asn Thr Ser Glu Ser Phe Val Leu Asn Trp Tyr Arg Met Ser Pro
35 40 45

Ser Asn Gln Thr Asp Lys Leu Ala Ala Phe Pro Glu Asp Arg Ser Gln
50 55 60

Pro Gly Gln Asp Ser Arg Phe Arg Val Thr Gln Leu Pro Asn Gly Arg
65 70 75 80

Asp Phe His Met Ser Val Val Arg Ala Arg Arg Ser Asp Ser Gly Thr
85 90 95

Tyr Leu Cys Gly Val Ile Ser Leu Ala Pro Lys Ala Gln Ile Lys Glu
100 105 110

Ser Leu Arg Ala Glu Leu Arg Val Thr Glu Arg Arg Ala Glu Val Pro
115 120 125

Thr Ala His Pro Ser Pro Ser Pro Arg Pro Ala Gly Gln Phe Gln
130 135 140

<210> SEQ ID NO 56
<211> LENGTH: 143
<212> TYPE: PRT
<213> ORGANISM: Artificial Sequence
<220> FEATURE:
<223> OTHER INFORMATION: PD-1 Variants No. 56 Protein sequence

<400> SEQUENCE: 56

Leu Asp Ser Pro Asp Arg Pro Trp Asn Pro Pro Thr Phe Ser Pro Ala
1 5 10 15

Leu Leu Val Val Thr Glu Gly Asp Asn Ala Thr Phe Thr Cys Ser Phe
20 25 30

Ser Asn Thr Pro Glu Ser Phe Val Leu Asn Trp Tyr Arg Met Ser Pro
35 40 45

Ser Asn Gln Thr Asp Lys Leu Ala Ala Phe Pro Glu Asp Arg Ser Gln
50 55 60

Pro Gly Gln Asp Ser Arg Phe Arg Val Thr Gln Leu Pro Asn Gly Arg
65 70 75 80

Asp Phe His Met Ser Val Val Arg Ala Arg Arg Lys Asp Ser Gly Thr
85 90 95

Tyr Leu Cys Gly Ala Ile Ser Leu Ala Pro Lys Ala Gln Ile Lys Glu
100 105 110

Ser Pro Arg Ala Glu Leu Arg Val Thr Glu Arg Arg Ala Glu Val Pro
115 120 125

Thr Ala Arg Pro Ser Pro Ser Pro Arg Pro Ala Gly Gln Phe Gln
130 135 140

<210> SEQ ID NO 57
<211> LENGTH: 143
<212> TYPE: PRT
<213> ORGANISM: Artificial Sequence
<220> FEATURE:
<223> OTHER INFORMATION: PD-1 Variants No. 66 Protein sequence

<400> SEQUENCE: 57

Leu Asp Ser Pro Asp Arg Pro Trp Asp Pro Pro Thr Phe Ser Pro Ala
1 5 10 15

Leu Leu Val Val Thr Glu Gly Asp Asp Ala Thr Phe Thr Cys Ser Phe
20 25 30

Ser Asn Thr Ser Glu Ser Phe Val Leu Asn Trp Tyr Arg Met Ser Pro
35 40 45

Ser Asn Gln Thr Asp Lys Leu Ala Ala Phe Pro Glu Asp Arg Ser Gln
50 55 60

Pro Gly Gln Asp Ser Arg Phe Arg Val Thr Gln Leu Pro Asn Gly Arg
65 70 75 80

Asp Phe His Met Ser Val Val Arg Ala Arg Arg Ser Asp Ser Gly Thr
85 90 95

Tyr Leu Cys Gly Val Ile Ser Leu Ala Pro Lys Ala Gln Ile Lys Glu
100 105 110

Ser Leu Arg Ala Glu Leu Arg Val Thr Glu Arg Arg Ala Glu Val Pro
115 120 125

Thr Ala His Pro Ser Pro Ser Pro Arg Pro Ala Gly Gln Phe Gln
130 135 140

<210> SEQ ID NO 58
<211> LENGTH: 143
<212> TYPE: PRT
<213> ORGANISM: Artificial Sequence
<220> FEATURE:
<223> OTHER INFORMATION: PD-1 Variants No. 67 Protein sequence

<400> SEQUENCE: 58

Leu Asp Ser Pro Asp Arg Pro Trp Asn Pro Pro Thr Phe Ser Pro Ala
1 5 10 15

Leu Leu Val Val Thr Glu Gly Asp Asn Ala Thr Phe Thr Cys Ser Phe
20 25 30

Ser Thr Thr Pro Glu Ser Phe Val Leu Asn Trp Tyr Arg Met Ser Pro
35 40 45

Ser Asn Gln Thr Asp Lys Leu Ala Ala Phe Pro Glu Asp Arg Ser Gln
50 55 60

Pro Gly Gln Asp Ser Arg Phe Arg Val Thr Gln Leu Pro Asn Gly Arg
65 70 75 80

Asp Phe His Met Ser Val Val Arg Ala Arg Arg Asn Asp Ser Gly Thr
85 90 95

Tyr Leu Cys Gly Ala Ile Ser Leu Ala Pro Lys Ala Gln Ile Lys Glu
100 105 110

Ser Pro Arg Ala Glu Leu Arg Val Thr Glu Arg Arg Ala Glu Val Pro
115 120 125

Thr Ala His Pro Ser Pro Ser Pro Arg Pro Ala Gly Gln Phe Gln
130 135 140

<210> SEQ ID NO 59
<211> LENGTH: 143
<212> TYPE: PRT
<213> ORGANISM: Artificial Sequence
<220> FEATURE:
<223> OTHER INFORMATION: PD-1 Variants No. 70 Protein sequence

<400> SEQUENCE: 59

Leu Asp Ser Pro Asp Arg Pro Trp Asn Pro Pro Thr Phe Ser Pro Ala
1 5 10 15

Leu Leu Val Val Thr Glu Gly Asp Asn Ala Thr Phe Thr Cys Ser Phe
20 25 30

Ser Asn Thr Pro Glu Ser Phe Val Leu Asn Trp Tyr Arg Met Ser Pro
35 40 45

Ser Asn Gln Thr Asp Lys Leu Ala Ala Phe Pro Glu Asp Arg Ser Gln
50 55 60

Pro Gly Gln Asp Ser Arg Phe Arg Val Thr Gln Leu Pro Asn Gly Arg
65 70 75 80

Asp Phe His Met Ser Val Val Arg Ala Arg Arg Asn Asp Ser Gly Thr

```
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln
    130                 135                 140


<210> SEQ ID NO 60
<211> LENGTH: 143
<212> TYPE: PRT
<213> ORGANISM: Artificial Sequence
<220> FEATURE:
<223> OTHER INFORMATION: PD-1 Variants No. 78  Protein sequence

<400> SEQUENCE: 60

Leu Asp Ser Pro Asp Arg Pro Trp Asn Pro Pro Ser Phe Ser Pro Ala
1               5                   10                  15

Leu Leu Val Val Thr Glu Gly Asp Asn Ala Thr Phe Thr Cys Ser Phe
            20                  25                  30

Ser Asn Thr Pro Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Ser Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Pro Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln
    130                 135                 140


<210> SEQ ID NO 61
<211> LENGTH: 143
<212> TYPE: PRT
<213> ORGANISM: Artificial Sequence
<220> FEATURE:
<223> OTHER INFORMATION: Wild type PD-1

<400> SEQUENCE: 61

Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110
```

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln
    130                 135                 140

<210> SEQ ID NO 62
<211> LENGTH: 61
<212> TYPE: DNA
<213> ORGANISM: Artificial Sequence
<220> FEATURE:
<223> OTHER INFORMATION: JY#5

<400> SEQUENCE: 62
ttagactccc cagacaggcc ctggaacccc cccaccttct ccccagccct gctcgtggtg 60
a 61

<210> SEQ ID NO 63
<211> LENGTH: 75
<212> TYPE: DNA
<213> ORGANISM: Artificial Sequence
<220> FEATURE:
<223> OTHER INFORMATION: JY#6

<400> SEQUENCE: 63
acgaagctct ccgatgtgtt ggagaagctg caggtgaagg tggcgttgtc cccttcggtc 60
accacgagca gggct 75

<210> SEQ ID NO 64
<211> LENGTH: 75
<212> TYPE: DNA
<213> ORGANISM: Artificial Sequence
<220> FEATURE:
<223> OTHER INFORMATION: JY#7

<400> SEQUENCE: 64
aacacatcgg agagcttcgt gctaaactgg taccgcatga gccccagcaa ccagacggac 60
aagctggccg ccttc 75

<210> SEQ ID NO 65
<211> LENGTH: 75
<212> TYPE: DNA
<213> ORGANISM: Artificial Sequence
<220> FEATURE:
<223> OTHER INFORMATION: JY#8

<400> SEQUENCE: 65
tgggcagttg tgtgacacgg aagcggctgg cctggcccag ctggccgcgg tcctcgggga 60
aggcggccag cttgt 75

<210> SEQ ID NO 66
<211> LENGTH: 75
<212> TYPE: DNA
<213> ORGANISM: Artificial Sequence
<220> FEATURE:
<223> OTHER INFORMATION: JY#9

<400> SEQUENCE: 66
cgtgtcacac aactgcccaa cgggcgtgac ttccacatga gcgtggtcag ggcccggcgc 60
agcgacagcg gcacc 75

<210> SEQ ID NO 67
<211> LENGTH: 75

<212> TYPE: DNA
<213> ORGANISM: Artificial Sequence
<220> FEATURE:
<223> OTHER INFORMATION: JY#10

<400> SEQUENCE: 67
acccgcaggc tctcccggat ctggatccgg ggggccagca ggatggcgct acagaggtag 60
gtgccgctgt cgctg 75

<210> SEQ ID NO 68
<211> LENGTH: 75
<212> TYPE: DNA
<213> ORGANISM: Artificial Sequence
<220> FEATURE:
<223> OTHER INFORMATION: JY#11

<400> SEQUENCE: 68
gggagagcct gcgggtggag ctcagggtga cagagagaag ggcagaagtg cccacagccc 60
accccagccc ctcac 75

<210> SEQ ID NO 69
<211> LENGTH: 39
<212> TYPE: DNA
<213> ORGANISM: Artificial Sequence
<220> FEATURE:
<223> OTHER INFORMATION: JY#12

<400> SEQUENCE: 69
ttggaactgg ccggctggcc tgggtgaggg gctggggtg 39

<210> SEQ ID NO 70
<211> LENGTH: 70
<212> TYPE: DNA
<213> ORGANISM: Artificial Sequence
<220> FEATURE:
<223> OTHER INFORMATION: JY#13

<400> SEQUENCE: 70
ttagactccc cagacaggcc ctggaacccc cccaccttct ccccagccct gctcgtggtg 60
accgaagggg 70

<210> SEQ ID NO 71
<211> LENGTH: 75
<212> TYPE: DNA
<213> ORGANISM: Artificial Sequence
<220> FEATURE:
<223> OTHER INFORMATION: JY#14

<400> SEQUENCE: 71
cagtttagca cgaagctctc cgatgtgttg gagaagctgc aggtgaaggt ggcgctgtcc 60
ccttcggtca ccacg 75

<210> SEQ ID NO 72
<211> LENGTH: 75
<212> TYPE: DNA
<213> ORGANISM: Artificial Sequence
<220> FEATURE:
<223> OTHER INFORMATION: JY#15

<400> SEQUENCE: 72
ggagagcttc gtgctaaact ggtaccgcat gagccccagc aaccaggccg acaagctggc 60
cgccttcccc gagga 75

<210> SEQ ID NO 73
<211> LENGTH: 75
<212> TYPE: DNA
<213> ORGANISM: Artificial Sequence
<220> FEATURE:
<223> OTHER INFORMATION: JY#16

<400> SEQUENCE: 73
cacgcccgtt gggcagttgt gtgacacgga agcgggagtc ctggccgggc tggctgcggt 60
cctcggggaa ggcgg 75

<210> SEQ ID NO 74
<211> LENGTH: 75
<212> TYPE: DNA
<213> ORGANISM: Artificial Sequence
<220> FEATURE:
<223> OTHER INFORMATION: JY#17

<400> SEQUENCE: 74
ctgcccaacg ggcgtgactt ccacatgagc gtggtcgggg cccggcgctc cgacagcggc 60
acctacctct gttcc 75

<210> SEQ ID NO 75
<211> LENGTH: 75
<212> TYPE: DNA
<213> ORGANISM: Artificial Sequence
<220> FEATURE:
<223> OTHER INFORMATION: JY#18

<400> SEQUENCE: 75
ctgagctctg cccgcaggct ctcccggatc tgcaccttgg gggccaggga gatggcggaa 60
cagaggtagg tgccg 75

<210> SEQ ID NO 76
<211> LENGTH: 75
<212> TYPE: DNA
<213> ORGANISM: Artificial Sequence
<220> FEATURE:
<223> OTHER INFORMATION: JY#19

<400> SEQUENCE: 76
ctgcgggcag agctcagggt ggcagagaga agggcagaag tgcccacagc ccaccccagc 60
ccctcaccca ggcca 75

<210> SEQ ID NO 77
<211> LENGTH: 31
<212> TYPE: DNA
<213> ORGANISM: Artificial Sequence
<220> FEATURE:
<223> OTHER INFORMATION: JY#20

<400> SEQUENCE: 77
ttggaactgg ccggctggcc tgggtgaggg g 31

<210> SEQ ID NO 78
<211> LENGTH: 35
<212> TYPE: DNA
<213> ORGANISM: Artificial Sequence
<220> FEATURE:
<223> OTHER INFORMATION: JY#21

<400> SEQUENCE: 78
ccccagcccc tcacccaggc cagccggcca gttcc 35

<210> SEQ ID NO 79
<211> LENGTH: 35
<212> TYPE: DNA
<213> ORGANISM: Artificial Sequence
<220> FEATURE:
<223> OTHER INFORMATION: JY#22

<400> SEQUENCE: 79
ggaactggcc ggctggcctg ggtgaggggc tgggg 35

<210> SEQ ID NO 80
<211> LENGTH: 600
<212> TYPE: DNA
<213> ORGANISM: Artificial Sequence
<220> FEATURE:
<223> OTHER INFORMATION: NlpA-PD-1 S.6.8.3-FLAG DNA sequence

<400> SEQUENCE: 80
atgaaactga caacacatca tctacggaca ggggccgcat tattgctggc cggaattctg 60
ctggcaggtt gcgaccagag tagcagcgag gcccagccgg ccttagactc cccagacagg 120
ccctggaacc cccccacctt ctccccagcc ctgctcgtgg tgaccgaagg ggacaacgcc 180
accttcacct gcagcttctc caacacatcg gagagcttcg tgctaaactg gtaccgcatg 240
agccccagca accagacgga caagctggcc gccttccccg aggaccgcgg ccagctgggc 300
caggccagcc gcttccgtgt cacacaactg cccaacgggc gtgacttcca catgagcgtg 360
gtcagggccc ggcgcagcga cagcggcacc tacctctgta gcgccatcct gctggccccc 420
cggatccaga tccgggagag cctgcgggtg gagctcaggg tgacagagag aagggcagaa 480
gtgcccacag cccaccccag cccctcaccc aggccagccg gccagttcca aggggcctcg 540
ggggccgaat tcgcggccgc tgcaccagat tataaagatg acgatgacaa agggcgcgcc 600

<210> SEQ ID NO 81
<211> LENGTH: 633
<212> TYPE: DNA
<213> ORGANISM: Artificial Sequence
<220> FEATURE:
<223> OTHER INFORMATION: NlpA-PD-1 S.5.1T-FLAG DNA sequence

<400> SEQUENCE: 81
atgaaactga caacacatca tctacggaca ggggccgcat tattgctggc cggaattctg 60
ctggcaggtt gcgaccagag tagcagcgag gcccagccgg cctgcgacca gagtagcagc 120
gaggcccagc cggccttaga ctccccagac aggccctgga acccccccac cttctcccca 180
gccctgctcg tggtgaccga aggggacagc gccaccttca cctgcagctt ctccaacaca 240
tcggagagct tcgtgctaaa ctggtaccgc atgagcccca gcaaccaggc cgacaagctg 300
gccgccttcc ccgaggaccg cagccagccc ggccaggact cccgcttccg tgtcacacaa 360
ctgcccaacg ggcgtgactt ccacatgagc gtggtcgggg cccggcgctc cgacagcggc 420
acctacctct gttccgccat ctccctggcc cccaaggtgc agatccggga gagcctgcgg 480
gcagagctca gggtggcaga gagaagggca gaagtgccca cagcccaccc cagcccctca 540
cccaggccag ccggccagtt ccaaggggcc tcgggggccg aattcgcggc cgctgcacca 600
gattataaag atgacgatga caaagggcgc gcc 633

<210> SEQ ID NO 82
<211> LENGTH: 429
<212> TYPE: DNA

<213> ORGANISM: Artificial Sequence
<220> FEATURE:
<223> OTHER INFORMATION: PD-1 Variants CKJ 41T DNA sequence

<400> SEQUENCE: 82
ttagactccc cagacaggcc ctggaacccc cccaccttct ccccagccct gctcgtggtg 60
accgaagggg acaacgccac cttcacctgc agcttctcca acacaccgga gagcttcgtg 120
ctaaactggt accgcatgag ccccagcaac cagacggaca agctggccgc cttccccgag 180
gaccgcagcc agcccggcca ggacacacgc ttccgtgtca cacaactgcc caacgggcgt 240
gacttccaca tgagcgtggt cagggcccgg cgcaatgaca gcggcaccta cctctgtggg 300
gccatctccc tggcccccaa ggcgcagatc aaagagagcc cgcgggcaga gctcagggtg 360
acagagagaa gggcagaagt gcccacagcc caccccagcc cctcacccag gccagccggc 420
cagttccaa 429

<210> SEQ ID NO 83
<211> LENGTH: 429
<212> TYPE: DNA
<213> ORGANISM: Artificial Sequence
<220> FEATURE:
<223> OTHER INFORMATION: PD-1 Variants CKJ 41Y DNA sequence

<400> SEQUENCE: 83
ttagactccc cagacaggcc ctggaacccc cccaccttct ccccagccct gctcgtggtg 60
accgaagggg acaacgccac cttcacctgc agcttctcca acacaccgga gagcttcgtg 120
ctaaactggt accgcatgag ccccagcaac cagacggaca agctggccgc cttccccgag 180
gaccgcagcc agcccggcca ggactaccgc ttccgtgtca cacaactgcc caacgggcgt 240
gacttccaca tgagcgtggt cagggcccgg cgcaatgaca gcggcaccta cctctgtggg 300
gccatctccc tggcccccaa ggcgcagatc aaagagagcc cgcgggcaga gctcagggtg 360
acagagagaa gggcagaagt gcccacagcc caccccagcc cctcacccag gccagccggc 420
cagttccaa 429

<210> SEQ ID NO 84
<211> LENGTH: 429
<212> TYPE: DNA
<213> ORGANISM: Artificial Sequence
<220> FEATURE:
<223> OTHER INFORMATION: PD-1 Variants CKJ 41G DNA sequence

<400> SEQUENCE: 84
ttagactccc cagacaggcc ctggaacccc cccaccttct ccccagccct gctcgtggtg 60
accgaagggg acaacgccac cttcacctgc agcttctcca acacaccgga gagcttcgtg 120
ctaaactggt accgcatgag ccccagcaac cagacggaca agctggccgc cttccccgag 180
gaccgcagcc agcccggcca ggacgggcgc ttccgtgtca cacaactgcc caacgggcgt 240
gacttccaca tgagcgtggt cagggcccgg cgcaatgaca gcggcaccta cctctgtggg 300
gccatctccc tggcccccaa ggcgcagatc aaagagagcc cgcgggcaga gctcagggtg 360
acagagagaa gggcagaagt gcccacagcc caccccagcc cctcacccag gccagccggc 420
cagttccaa 429

<210> SEQ ID NO 85
<211> LENGTH: 429
<212> TYPE: DNA
<213> ORGANISM: Artificial Sequence
<220> FEATURE:
<223> OTHER INFORMATION: PD-1 Variants CKJ 41A DNA sequence

<400> SEQUENCE: 85
ttagactccc cagacaggcc ctggaacccc cccaccttct ccccagccct gctcgtggtg 60
accgaagggg acaacgccac cttcacctgc agcttctcca acacaccgga gagcttcgtg 120
ctaaactggt accgcatgag ccccagcaac cagacggaca agctggccgc cttccccgag 180
gaccgcagcc agcccggcca ggacgcccgc ttccgtgtca cacaactgcc caacgggcgt 240
gacttccaca tgagcgtggt cagggcccgg cgcaatgaca gcggcaccta cctctgtggg 300
gccatctccc tggcccccaa ggcgcagatc aaagagagcc cgcgggcaga gctcagggtg 360
acagagagaa gggcagaagt gcccacagcc caccccagcc cctcacccag gccagccggc 420
cagttccaa 429

<210> SEQ ID NO 86
<211> LENGTH: 429
<212> TYPE: DNA
<213> ORGANISM: Artificial Sequence
<220> FEATURE:
<223> OTHER INFORMATION: PD-1 Variants JY 101 DNA sequence

<400> SEQUENCE: 86
tcagactccc cagacaggcc ctggaacccc cccaccatat ccccagccat gctcgtggtg 60
accgaagggg acaacgctac cttcacctgc agcttctcca acacaccgga gagcttcgtg 120
ctaaactggt accgcataag ccccagcaac cagacggaca agctggccgc cttccccgag 180
gaccgcagcc agcccggcca ggacacacgc ttccgtgtca cacaactgcc caacaggcgt 240
gacttccaca tgagcgtggt cagggcccgg cgcaatgaca gcggcaccta cctctgtgtg 300
gccatctccc tggcccccaa ggcgcagatc aaagagagcc cgcgggcaga gctcagggtg 360
acagagagaa gggcagaagt gcccacagcc caccccagcc cctcacccag gccattaggc 420
cagttccaa 429

<210> SEQ ID NO 87
<211> LENGTH: 429
<212> TYPE: DNA
<213> ORGANISM: Artificial Sequence
<220> FEATURE:
<223> OTHER INFORMATION: PD-1 Variants LDSS DNA sequence

<400> SEQUENCE: 87
ttagactccc cagacaggcc ctggaacccc cccaccctct ccccagccct gctcgtggtg 60
accgaagggg acgacgccac cttcacctgc agcttctcca acacatcgga gagcttcgtg 120
ctaaactggt accgcatgag ccccagcaac cagacggaca agctggccgc cttccccgag 180
gaccgcagcc agcccggcca ggactcccgc ttccgtgtca cacaactgcc caacgggcgt 240
gacttccaca tgagcgtggt cagggcccgg cgcagtgaca gcggcaccta cctctgtggg 300
gccatctccc tggcccccaa ggcgcagatc aaagagagcc tgcgggcaga gctcagggtg 360
acagagagaa gggcagaagt gcccacagcc caccccagcc cctcacccag gccagccggc 420
cagttccaa 429

<210> SEQ ID NO 88
<211> LENGTH: 200
<212> TYPE: PRT
<213> ORGANISM: Artificial Sequence
<220> FEATURE:

<223> OTHER INFORMATION: NlpA-PD-1 S.6.8.3-FLAG Protein sequence

<400> SEQUENCE: 88

Met Lys Leu Thr Thr His His Leu Arg Thr Gly Ala Ala Leu Leu Leu
1 5 10 15

Ala Gly Ile Leu Leu Ala Gly Cys Asp Gln Ser Ser Ser Glu Ala Gln
20 25 30

Pro Ala Leu Asp Ser Pro Asp Arg Pro Trp Asn Pro Pro Thr Phe Ser
35 40 45

Pro Ala Leu Leu Val Val Thr Glu Gly Asp Asn Ala Thr Phe Thr Cys
50 55 60

Ser Phe Ser Asn Thr Ser Glu Ser Phe Val Leu Asn Trp Tyr Arg Met
65 70 75 80

Ser Pro Ser Asn Gln Thr Asp Lys Leu Ala Ala Phe Pro Glu Asp Arg
85 90 95

Gly Gln Leu Gly Gln Ala Ser Arg Phe Arg Val Thr Gln Leu Pro Asn
100 105 110

Gly Arg Asp Phe His Met Ser Val Val Arg Ala Arg Arg Ser Asp Ser
115 120 125

Gly Thr Tyr Leu Cys Ser Ala Ile Leu Leu Ala Pro Arg Ile Gln Ile
130 135 140

Arg Glu Ser Leu Arg Val Glu Leu Arg Val Thr Glu Arg Arg Ala Glu
145 150 155 160

Val Pro Thr Ala His Pro Ser Pro Ser Pro Arg Pro Ala Gly Gln Phe
165 170 175

Gln Gly Ala Ser Gly Ala Glu Phe Ala Ala Ala Ala Pro Asp Tyr Lys
180 185 190

Asp Asp Asp Asp Lys Gly Arg Ala
195 200

<210> SEQ ID NO 89
<211> LENGTH: 200
<212> TYPE: PRT
<213> ORGANISM: Artificial Sequence
<220> FEATURE:
<223> OTHER INFORMATION: NlpA-PD-1 S.5.1T-FLAG Protein sequence

<400> SEQUENCE: 89

Met Lys Leu Thr Thr His His Leu Arg Thr Gly Ala Ala Leu Leu Leu
1 5 10 15

Ala Gly Ile Leu Leu Ala Gly Cys Asp Gln Ser Ser Ser Glu Ala Gln
20 25 30

Pro Ala Leu Asp Ser Pro Asp Arg Pro Trp Asn Pro Pro Thr Phe Ser
35 40 45

Pro Ala Leu Leu Val Val Thr Glu Gly Asp Ser Ala Thr Phe Thr Cys
50 55 60

Ser Phe Ser Asn Thr Ser Glu Ser Phe Val Leu Asn Trp Tyr Arg Met
65 70 75 80

Ser Pro Ser Asn Gln Ala Asp Lys Leu Ala Ala Phe Pro Glu Asp Arg
85 90 95

Ser Gln Pro Gly Gln Asp Ser Arg Phe Arg Val Thr Gln Leu Pro Asn
100 105 110

Gly Arg Asp Phe His Met Ser Val Val Gly Ala Arg Arg Ser Asp Ser
115 120 125

Gly Thr Tyr Leu Cys Ser Ala Ile Ser Leu Ala Pro Lys Val Gln Ile
130 135 140

```
Arg Glu Ser Leu Arg Ala Glu Leu Arg Val Ala Glu Arg Arg Ala Glu
145                 150                 155                 160

Val Pro Thr Ala His Pro Ser Pro Ser Pro Arg Pro Ala Gly Gln Phe
                165                 170                 175

Gln Gly Ala Ser Gly Ala Glu Phe Ala Ala Ala Ala Pro Asp Tyr Lys
            180                 185                 190

Asp Asp Asp Asp Lys Gly Arg Ala
        195                 200


<210> SEQ ID NO 90
<211> LENGTH: 143
<212> TYPE: PRT
<213> ORGANISM: Artificial Sequence
<220> FEATURE:
<223> OTHER INFORMATION: PD-1 Variants CKJ 41T Protein sequence

<400> SEQUENCE: 90

Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Pro Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Thr Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Pro Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln
    130                 135                 140


<210> SEQ ID NO 91
<211> LENGTH: 143
<212> TYPE: PRT
<213> ORGANISM: Artificial Sequence
<220> FEATURE:
<223> OTHER INFORMATION: PD-1 Variants CKJ 41Y Protein sequence

<400> SEQUENCE: 91

Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Pro Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Tyr Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
```

100 105 110

Ser Pro Arg Ala Glu Leu Arg Val Thr Glu Arg Arg Ala Glu Val Pro
115 120 125

Thr Ala His Pro Ser Pro Ser Pro Arg Pro Ala Gly Gln Phe Gln
130 135 140

<210> SEQ ID NO 92
<211> LENGTH: 143
<212> TYPE: PRT
<213> ORGANISM: Artificial Sequence
<220> FEATURE:
<223> OTHER INFORMATION: PD-1 Variants CKJ 41G Protein sequence

<400> SEQUENCE: 92

Leu Asp Ser Pro Asp Arg Pro Trp Asn Pro Pro Thr Phe Ser Pro Ala
1 5 10 15

Leu Leu Val Val Thr Glu Gly Asp Asn Ala Thr Phe Thr Cys Ser Phe
20 25 30

Ser Asn Thr Pro Glu Ser Phe Val Leu Asn Trp Tyr Arg Met Ser Pro
35 40 45

Ser Asn Gln Thr Asp Lys Leu Ala Ala Phe Pro Glu Asp Arg Ser Gln
50 55 60

Pro Gly Gln Asp Gly Arg Phe Arg Val Thr Gln Leu Pro Asn Gly Arg
65 70 75 80

Asp Phe His Met Ser Val Val Arg Ala Arg Arg Asn Asp Ser Gly Thr
85 90 95

Tyr Leu Cys Gly Ala Ile Ser Leu Ala Pro Lys Ala Gln Ile Lys Glu
100 105 110

Ser Pro Arg Ala Glu Leu Arg Val Thr Glu Arg Arg Ala Glu Val Pro
115 120 125

Thr Ala His Pro Ser Pro Ser Pro Arg Pro Ala Gly Gln Phe Gln
130 135 140

<210> SEQ ID NO 93
<211> LENGTH: 143
<212> TYPE: PRT
<213> ORGANISM: Artificial Sequence
<220> FEATURE:
<223> OTHER INFORMATION: PD-1 Variants CKJ 41A Protein sequence

<400> SEQUENCE: 93

Leu Asp Ser Pro Asp Arg Pro Trp Asn Pro Pro Thr Phe Ser Pro Ala
1 5 10 15

Leu Leu Val Val Thr Glu Gly Asp Asn Ala Thr Phe Thr Cys Ser Phe
20 25 30

Ser Asn Thr Pro Glu Ser Phe Val Leu Asn Trp Tyr Arg Met Ser Pro
35 40 45

Ser Asn Gln Thr Asp Lys Leu Ala Ala Phe Pro Glu Asp Arg Ser Gln
50 55 60

Pro Gly Gln Asp Ala Arg Phe Arg Val Thr Gln Leu Pro Asn Gly Arg
65 70 75 80

Asp Phe His Met Ser Val Val Arg Ala Arg Arg Asn Asp Ser Gly Thr
85 90 95

Tyr Leu Cys Gly Ala Ile Ser Leu Ala Pro Lys Ala Gln Ile Lys Glu
100 105 110

Ser Pro Arg Ala Glu Leu Arg Val Thr Glu Arg Arg Ala Glu Val Pro
115 120 125

Thr Ala His Pro Ser Pro Ser Pro Arg Pro Ala Gly Gln Phe Gln
130 135 140

<210> SEQ ID NO 94
<211> LENGTH: 143
<212> TYPE: PRT
<213> ORGANISM: Artificial Sequence
<220> FEATURE:
<223> OTHER INFORMATION: PD-1 Variants JY 101 Protein sequence

<400> SEQUENCE: 94

Ser Asp Ser Pro Asp Arg Pro Trp Asn Pro Pro Thr Ile Ser Pro Ala
1 5 10 15

Met Leu Val Val Thr Glu Gly Asp Asn Ala Thr Phe Thr Cys Ser Phe
20 25 30

Ser Asn Thr Pro Glu Ser Phe Val Leu Asn Trp Tyr Arg Ile Ser Pro
35 40 45

Ser Asn Gln Thr Asp Lys Leu Ala Ala Phe Pro Glu Asp Arg Ser Gln
50 55 60

Pro Gly Gln Asp Thr Arg Phe Arg Val Thr Gln Leu Pro Asn Arg Arg
65 70 75 80

Asp Phe His Met Ser Val Val Arg Ala Arg Arg Asn Asp Ser Gly Thr
85 90 95

Tyr Leu Cys Val Ala Ile Ser Leu Ala Pro Lys Ala Gln Ile Lys Glu
100 105 110

Ser Pro Arg Ala Glu Leu Arg Val Thr Glu Arg Arg Ala Glu Val Pro
115 120 125

Thr Ala His Pro Ser Pro Ser Pro Arg Pro Leu Gly Gln Phe Gln
130 135 140

<210> SEQ ID NO 95
<211> LENGTH: 143
<212> TYPE: PRT
<213> ORGANISM: Artificial Sequence
<220> FEATURE:
<223> OTHER INFORMATION: PD-1 Variants LDSS Protein sequence

<400> SEQUENCE: 95

Leu Asp Ser Pro Asp Arg Pro Trp Asn Pro Pro Thr Leu Ser Pro Ala
1 5 10 15

Leu Leu Val Val Thr Glu Gly Asp Asp Ala Thr Phe Thr Cys Ser Phe
20 25 30

Ser Asn Thr Ser Glu Ser Phe Val Leu Asn Trp Tyr Arg Met Ser Pro
35 40 45

Ser Asn Gln Thr Asp Lys Leu Ala Ala Phe Pro Glu Asp Arg Ser Gln
50 55 60

Pro Gly Gln Asp Ser Arg Phe Arg Val Thr Gln Leu Pro Asn Gly Arg
65 70 75 80

Asp Phe His Met Ser Val Val Arg Ala Arg Arg Ser Asp Ser Gly Thr
85 90 95

Tyr Leu Cys Gly Ala Ile Ser Leu Ala Pro Lys Ala Gln Ile Lys Glu
100 105 110

Ser Leu Arg Ala Glu Leu Arg Val Thr Glu Arg Arg Ala Glu Val Pro
115 120 125

Thr Ala His Pro Ser Pro Ser Pro Arg Pro Ala Gly Gln Phe Gln
130 135 140

PD-1 VARIANT HAVING IMPROVED BINDING ABILITY TO PD-L1

CROSS-REFERENCE TO RELATED APPLICATIONS

This application is a § 371 national stage entry of International Application No. PCT/KR2019/001290, filed on Jan. 30, 2019, which claims priority to South Korean Patent Application No. 10-2018-0013381, filed on Feb. 2, 2018, and South Korean Patent Application No. 10-2019-0011181, filed on Jan. 29, 2019, the entire contents of which are incorporated herein by reference.

TECHNICAL FIELD

The present disclosure relates to a PD-1 variant having improved binding affinity to PD-L1 and, thus, effectively inhibiting the binding between wild-type PD-1 and PD-L1, and a method for preparing the same.

SEQUENCE LISTING

The instant application contains a Sequence Listing which has been submitted electronically in ASCII format and is hereby incorporated by reference in its entirety. Said ASCII copy, created on Oct. 5, 2020, is named G1035-17001_SequenceListingRevised.txt and is 73,835 bytes in size.

BACKGROUND ART

Drugs for treating cancer are largely classified into low-molecular-weight drugs and high-molecular-weight drugs. The high-molecular-weight drugs having specificity are more popular than the low-molecular-weight drugs which lack specificity and, thus, have relatively more side effects.

Recently, it was reported that the inhibition of the binding of immune checkpoint inhibitor proteins, particularly PD-1/PD-L1, is significantly effective in treating cancer and that they have fewer side effects as compared to other immune checkpoint inhibitor proteins (J. Naidoo et al. (2015) Annals of Oncology, Lucia Gelao et al. (2014) Toxins, Gorge K. Philips et al. (2015) International Immunology).

Big pharmaceutical companies such as Bristol-Myers Squibb, etc. are making efforts to develop therapeutic drugs such as through inhibition of PD-1/PD-L1 immune checkpoint inhibitors, and anticancer drugs such as Yervoy (ipilimumab) and Opdivo (nivolumab) are being developed using antibody formats.

In order to remove the binding of tumor-infiltrating lymphocytes (TILs) to PD-1/PD-L1, a therapeutic agent with excellent cell infiltration ability is necessary. However, antibodies have disadvantages in infiltrating into cells because they are macromolecular proteins with a very large size of about 150 kDa.

For treatment of cancer through effective immune checkpoint inhibition, PD-1 having superior cell infiltration ability due to smaller size seems more suitable than PD-L1. However, the existing PD-1 engineering has been based on screening through yeast display and there is a risk of immunogenicity due to glycan heterogeneity and various mutations.

Meanwhile, aglycosylated protein drugs can be easily produced in large scale in bacteria and have great advantages in biomedicine preparation with no glycan heterogeneity problem associated with cell lines, culturing process or purification process.

Accordingly, screening of an aglycosylated PD-1 variant having little mutation and high binding affinity to PD-L1 is necessary.

The foregoing description of the background art is given only for enhancing the understanding of the background of the present disclosure and it should not be accepted to acknowledge as a prior art well known to those of ordinary skill in the art.

DISCLOSURE

Technical Problem

The inventors of the present disclosure have made consistent efforts to screen a PD-1 variant having high binding affinity to PD-L1 and thus capable of effectively inhibiting the binding between wild-type PD-1 and PD-L1 and minimizing the possibility of immunogenicity at the same time. As a result, they have identified that, the binding affinity to PD-L1 can be improved greatly by substituting a part of the amino sequence of wild-type PD-1 with another amino sequence and the possibility of immunogenicity can be reduced through minimization of mutation sites and/or aglycosylated PD-1, and have completed the present disclosure.

The present disclosure is directed to providing a PD-1 variant having improved binding affinity to PD-L1.

The present disclosure is also directed to providing a nucleic acid molecule encoding the PD-1 variant.

The present disclosure is also directed to providing a vector including the nucleic acid molecule.

The present disclosure is also directed to providing a host cell including the vector.

The present disclosure is also directed to providing a composition including the PD-1 variant, the nucleic acid molecule or the vector.

The present disclosure is also directed to providing a method for preparing the PD-1 variant.

The present disclosure is also directed to providing an inhibitor of the binding between wild-type PD-1 and PD-L1, which includes the PD-1 variant, the nucleic acid molecule or the vector as an active ingredient.

The present disclosure is also directed to providing a method for inhibiting the binding between wild-type PD-1 and PD-L1, which includes a step of administering an effective amount of the PD-1 variant, the nucleic acid molecule or the vector to a subject.

The present disclosure is also directed to providing a method for treating a cancer disease or an infectious disease, which includes a step of administering a therapeutically effective amount of the PD-1 variant, the nucleic acid molecule or the vector to a subject.

The present disclosure is also directed to providing a method for screening the PD-1 variant.

Other purposes and advantages of the present disclosure will become more apparent by the following detailed description, claims and drawings.

Technical Solution

In an aspect of the present disclosure, the present disclosure provides a PD-1 variant having improved binding affinity to PD-L1.

The inventors of the present disclosure have made consistent efforts to screen a PD-1 variant having high binding affinity to PD-L1 and thus capable of effectively inhibiting the binding between wild-type PD-1 and PD-L1 and minimizing the possibility of immunogenicity at the same time.

As a result, they have identified that, the binding affinity to PD-L1 can be improved greatly by substituting a part of the amino sequence of wild-type PD-1 with another amino sequence and the possibility of immunogenicity can be reduced through minimization of mutation sites and/or aglycosylated PD-1, and have completed the present disclosure.

As used herein, the term "PD-1 variant" or "programmed cell death protein 1 variant" refers to a variant of wild-type PD-1, wherein one or two or more amino acids in the amino sequence includes a substitution, deletion or addition mutation.

In a specific exemplary embodiment of the present disclosure, the amino sequence of wild-type PD-1 includes an amino sequence of SEQ ID NO 61.

In a specific exemplary embodiment of the present disclosure, the PD-1 (programmed cell death protein 1) variant having improved binding affinity to PD-L1 (programmed death-ligand 1) includes a part of the amino sequence of wild-type PD-1, and includes substitution of the 69th amino acid of the amino sequence of wild-type PD-1 of SEQ ID NO 61 with a sequence different from the wild-type amino acid.

In a specific exemplary embodiment of the present disclosure, the 69th amino acid is substituted with C69S, C69T, C69Y, C69G or C69A.

In a specific exemplary embodiment of the present disclosure, the PD-1 variant further includes substitution of the 36th amino acid of the amino sequence of wild-type PD-1 of SEQ ID NO 61 with S36P.

In a specific exemplary embodiment of the present disclosure, the PD-1 variant further includes substitution of the 114th amino acid of the amino sequence of wild-type PD-1 of SEQ ID NO 61 with L114P.

In a specific exemplary embodiment of the present disclosure, the PD-1 variant further includes substitution of one or more amino acid selected from a group consisting of the 12th, 34th, 92nd, 107th, 131st, 132nd and 142nd amino acids of the amino sequence of wild-type PD-1 of SEQ ID NO 61 with a sequence different from the wild-type amino acid.

In a specific exemplary embodiment of the present disclosure, the PD-1 variant includes one or more amino acid substitutions selected from a group consisting of T12S, N34T, N92K or N92S, K107N, H131R, P132L and F142L.

In a specific exemplary embodiment of the present disclosure, the PD-1 variant further includes substitution of the 13th amino acid of the amino sequence of wild-type PD-1 of SEQ ID NO 61 with F13I or F13L, and the 46th amino acid with M46I.

In a specific exemplary embodiment of the present disclosure, the PD-1 variant further includes substitution of one or more amino acids selected from a group consisting of the 1st, 17th, 36th, 50th, 79th, 100th, 114th, 127th and 139th amino acids of the amino sequence of wild-type PD-1 of SEQ ID NO 61 with a sequence different from the wild-type amino acid.

In a specific exemplary embodiment of the present disclosure, the PD-1 variant includes one or more amino acid substitutions selected from the group consisting of L1S, L17M, S36P, N50S, G79R, G100V, L114P, V127A and A139L.

In a specific exemplary embodiment of the present disclosure, the PD-1 variant further includes substitution of the 25th amino acid of the amino sequence of wild-type PD-1 of SEQ ID NO 61 with N25D, and the 92nd amino acid with N92S or N92K.

In a specific exemplary embodiment of the present disclosure, the PD-1 variant further includes substitution of the 13th amino acid of the amino sequence of wild-type PD-1 of SEQ ID NO 61 with F13I or F13L.

In a specific exemplary embodiment of the present disclosure, the PD-1 variant further includes substitution of one or more amino acids selected from a group consisting of the 9th, 88th, 101st, 125th and 137th amino acids of the amino sequence of wild-type PD-1 of SEQ ID NO 61 with a sequence different from the wild-type amino acid.

In a specific exemplary embodiment of the present disclosure, the PD-1 variant includes one or more amino acid substitutions selected from a group consisting of N9D, R88K, A101V, A125S and R137K.

In a specific exemplary embodiment of the present disclosure, the PD-1 variant is an aglycosylated PD-1 variant.

At present, most of commercially available therapeutic proteins are produced through animal cell culturing. When the proteins are produced, they are modified by various sugar (carbohydrate) variants. In this regard, glycan heterogeneity causes variation in the efficacy and stability of the therapeutic proteins, and a significant cost is required for purification, analysis and quality control (QC) during the preparation process of the proteins.

When compared with glycosylated proteins requiring the expensive animal cell culturing system, the aglycosylated proteins can be produced on a large scale in bacteria and exhibit superior excellence in terms of production speed and costs.

In another aspect of the present disclosure, the present disclosure provides a nucleic acid molecule encoding the PD-1 variant, a vector including the same or a host cell including the vector.

In a specific exemplary embodiment of the present disclosure, the host cell is a bacterial cell.

The nucleic acid molecule of the present disclosure may be an isolated or recombinant nucleic acid molecule, and includes not only single-stranded and double-stranded DNA and RNA but also complementary sequences corresponding thereto. When the "isolated nucleic acid" is a nucleic acid isolated from a natural origin, the nucleic acid is a nucleic acid separated from nearby gene sequences existing in the isolated genome of an individual. For nucleic acids, e.g., PCR products, cDNA molecules or oligonucleotides, enzymatically or chemically synthesized from a template, the nucleic acids produced from these procedures may be understood as isolated nucleic acid molecules. An isolated nucleic acid molecule may be a component of a fragment or a lager nucleic acid construct. A nucleic acid is "operably linked" when it is placed into a functional relationship with another nucleic acid sequence. For example, a DNA for a pre-sequence or a secretory leader is operably linked to a DNA for a polypeptide if it is expressed as a pre-protein that participates in the secretion of the polypeptide. A promoter or enhancer is operably linked to a coding sequence if it affects the transcription of the polypeptide sequence. And, a ribosome-binding site is operably linked to a coding sequence if it is positioned so as to facilitate translation. In general, "operably linked" means that the DNA sequences being linked are contiguous, and, in the case of a secretory leader, contiguous and present in the same reading frame. However, enhancers do not have to be contiguous. The linking is accomplished by ligation at convenient restriction enzyme sites. If such sites do not exist, synthetic oligonucleotide adaptors or linkers are used in accordance with common methods.

As used herein, the term "vector" refers to a carrier capable of inserting a nucleic acid sequence for introduction into a cell capable of replicating the nucleic acid sequence. The nucleic acid sequence may be exogenous or heterologous. The vector may be a plasmid, a cosmid or a virus (e.g., a bacteriophage), although not being limited thereto. Those skilled in the art can construct the vector according to the standard recombination technology (Maniatis, et al., Molecular Cloning, A Laboratory Manual, Cold Spring Harbor Press, Cold Spring Harbor, N.Y., 1988; Ausubel et al., In: Current Protocols in Molecular Biology, John, Wiley & Sons, Inc., NY, 1994, etc.).

As used herein, the term "expression vector" refers to a vector including a nucleic acid sequence encoding at least a part of a transcribed gene product. In some cases, an RNA molecule is post-translated into a protein, a polypeptide or a peptide. The expression vector may contain various regulatory sequences. A vector or an expression vector may further contain a nucleic acid sequence that provides another function, in addition to a regulatory sequence regulating transcription and translation.

As used herein, the term "host cell" refers to a cell of any transformable organism, including a eukaryote and a prokaryote, which is capable of replicating the vector or expressing a gene encoded by the vector. The host cell may be transfected or transformed by the vector, which means a process by which an exogenous nucleic acid molecule is delivered or introduced into the host cell.

In a specific exemplary embodiment of the present disclosure, the host cell of the present disclosure is a bacterial cell, more specifically a Gram-negative bacterial cell. The cell is adequate for the present disclosure in that it has a periplasmic region between the inner and outer membranes. Specific examples of the host cell according to the present disclosure include the cell of *E. coli, Pseudomonas aeruginosa, Vibrio cholera, Salmonella typhimurium, Shigella flexneri, Haemophilus* influenza, *Bordotella pertussi, Erwinia amylovora, Rhizobium* sp., etc., although not being limited thereto.

In another aspect of the present disclosure, the present disclosure provides an inhibitor of the binding between wild-type PD-1 (programmed cell death protein 1) and PD-L1 (programmed death-ligand 1), which includes the PD-1 variant, the nucleic acid molecule or the vector as an active ingredient.

In another aspect of the present disclosure, the present disclosure provides a composition including the PD-1 variant, the nucleic acid molecule or the vector as an active ingredient.

The composition is specifically a pharmaceutical composition, more specifically a pharmaceutical composition for preventing or treating a cancer disease or an infectious disease.

In another aspect of the present disclosure, the present disclosure provides a method for inhibiting binding between wild-type PD-1 (programmed cell death protein 1) and PD-L1 (programmed death-ligand 1), which includes a step of administering an effective amount of the PD-1 variant, the nucleic acid molecule or the vector to a subject.

In another aspect of the present disclosure, the present disclosure provides a method for enhancing immune response, which includes a step of administering an effective amount of the PD-1 variant, the nucleic acid molecule or the vector to a subject.

In another aspect of the present disclosure, the present disclosure provides a method for treating a cancer disease or an infectious disease, which includes a step of administering a therapeutically effective amount of the PD-1 variant, the nucleic acid molecule or the vector to a subject.

The pharmaceutical composition of the present disclosure may include: (a) the PD-1 variant, the nucleic acid molecule or the vector; and (b) a pharmaceutically acceptable carrier.

The type of the cancer to be prevented or treated in the present disclosure is not limited. The pharmaceutical composition may be administered to treat various cancers including leukemia such as acute lymphocytic leukemia, acute nonlymphocytic leukemia, chronic lymphocytic leukemia and chronic myelogenous leukemia, lymphomas such as Hodgkin's disease, non-Hodgkin lymphoma, multiple myeloma, etc., childhood solid tumors such as brain tumor, neuroblastoma, retinoblastoma, Wilms' tumors, bone tumors, soft-tissue sarcomas, etc., and common solid tumors in adults such as lung cancer, breast cancer, prostate cancer, urinary cancer, uterine cancer, oral cancer, pancreatic cancer, melanoma and other skin cancers, stomach cancer, ovarian cancer, brain tumor, liver cancer, laryngeal cancer, thyroid cancer, esophageal cancer, testicular cancer, etc.

The infectious diseases to be prevented or treated in the present disclosure are not limited in type and includes viral infection, influenza infection, bacterial infection and fungal infection.

The pharmaceutically acceptable carrier contained in the pharmaceutical composition of the present disclosure is one commonly used for preparation and includes lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., although not being limited thereto. The pharmaceutical composition of the present disclosure may further include a lubricant, a humectant, a sweetener, a flavorant, an emulsifier, a suspending agent, a preservative, etc. in addition to the above-described ingredients. Adequate pharmaceutically acceptable carriers and preparations are described in detail in Remington's Pharmaceutical Sciences (19th ed., 1995).

The pharmaceutical composition of the present disclosure may be administered orally or parenterally, specifically parenterally. For example, it may be administered via intravenous injection, topical injection, intraperitoneal injection, etc.

As used herein, the term "subject" refers to a subject in which the above-described disease is to be prevented or treated by inhibiting the binding between PD-1 and PD-L1, and includes specifically human and animals.

An adequate administration dosage of the pharmaceutical composition of the present disclosure varies depending on factors such as formulation method, administration method, the age, body weight, sex and pathological condition of a patient, diet, administration time, administration route, excretion rate and response sensitivity. A normally skilled practitioner can easily determine and prescribe an administration dosage effective for desired treatment or prevention. In a specific exemplary embodiment of the present disclosure, a daily administration dosage of the pharmaceutical composition of the present disclosure is 0.0001-100 mg/kg.

The pharmaceutical composition of the present disclosure may be prepared as a single-dose or multiple-dose formulation using a pharmaceutically acceptable carrier and/or excipient according to a method that can be easily carried out by those of ordinary skill in the art to which the present disclosure belongs. The formulation may be in the form of a solution in an oily or aqueous medium, a suspension, an emulsion, an extract, a powder, a granule, a tablet or a capsule, and may further contain a dispersant or a stabilizer.

The pharmaceutical composition of the present disclosure may be used either alone or in combination with common biological, chemical or radiation therapies. The combined therapies may be more effective in treating a cancer or an infectious disease. A chemotherapeutic agent that may be used together with the composition of the present disclosure includes cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicamycin, mitomycin, etoposide, tamoxifen, taxol, transplatinum, 5-fluorouracil, vincristine, vinblastine, methotrexate, etc. The radiation therapy that may be used together with the composition of the present disclosure includes X-ray radiation, γ-ray radiation, etc.

In another aspect of the present disclosure, the present disclosure provides a method for preparing the PD-1 variant, which includes the following steps:

a) a step of culturing a host cell including a vector including a nucleic acid molecule encoding the PD-1 variant; and b) a step of recovering the PD-1 variant expressed by the host cell.

In another aspect, the present disclosure is a method for screening the PD-1 variant, which includes the following steps:

a) a step of establishing a library of the PD-1 variant to which random point mutations have been introduced or a nucleic acid molecule encoding the same; and b) a step of screening the PD-1 variant which inhibits the binding between wild-type PD-1 (programmed cell death protein 1) and PD-L1 (programmed death-ligand 1) from the library.

The screening method according to the present disclosure may employ fluorescence-activated cell sorting (FACS) screening or other automated flow cytometry techniques. The instruments for carrying out flow cytometry are known to those skilled in the art. Examples of the instruments include FACSAria, FACS Star Plus, FACScan and FACSort (Becton Dickinson, Foster City, CA), Epics C (Coulter Epics Division, Hialeah, FL), MOFLO (Cytomation, Colorado Springs, Colo.), and MOFLO-XDP (Beckman Coulter, Indianapolis, IN). Generally, the flow cytometry technique involves separation of cells or other particles from a liquid sample. Typically, the purpose of flow cytometry is to analyze the separated particles for one or more characteristics (for example, the presence of a labeled ligand or other molecules). The particles are sorted based on their size, refraction, light scattering, opacity, roughness, shape, fluorescence, etc. by a sensor as they flow one by one.

Advantageous Effects

The features and advantages of the present disclosure may be summarized as follows:

(i) The present disclosure provides a PD-1 variant having improved binding affinity to PD-L1.

(ii) The present disclosure also provides a method for preparing and a method for screening the PD-1 variant.

(iii) The PD-1 variant of the present disclosure effectively inhibits the binding between wild-type PD-1 and PD-L1, and thus is expected to have significantly higher penetration affinity and anticancer effect by immune cells or therapeutic effect for infectious diseases as compared to existing immune checkpoint inhibitors. At the same time, the possibility of immunogenicity can be minimized. In addition, the convenience of developing biomedicine may be promoted through aglycosylation.

BRIEF DESCRIPTION OF DRAWINGS

FIG. 3 shows a result of preparing fluorescence-labeling tetrameric PD-L1 and investigating its activity.

BEST MODE

Hereinafter, the present disclosure will be described in detail through examples. The examples are provided only for the purpose of describing the present disclosure specifically and it will be obvious to those of ordinary skill in the art that the scope of the present disclosure is not limited by the examples.

EXAMPLES

Example 1: Verification of N-Linked Glycosylation Site Affecting Binding to Human PD-L1

Figure 1:
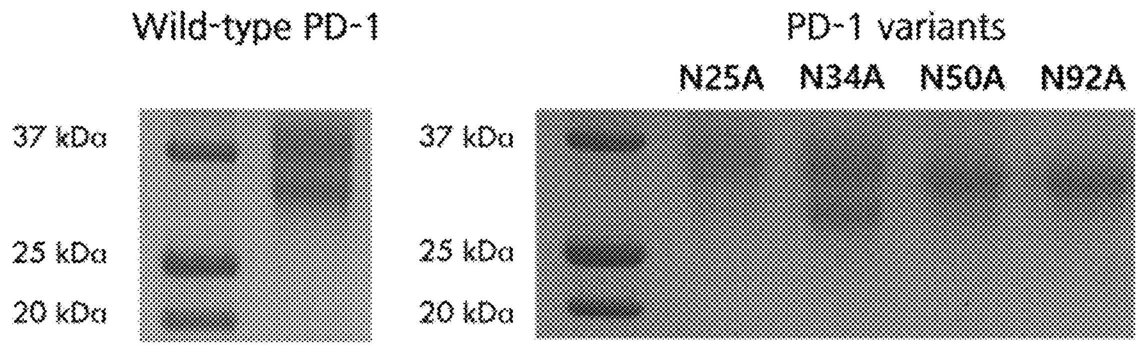
FIG. 1 shows SDS-PAGE images of wild-type PD-1 and four PD-1 glycovariants, which have been produced in animal cells and then purified.
Figure 2:
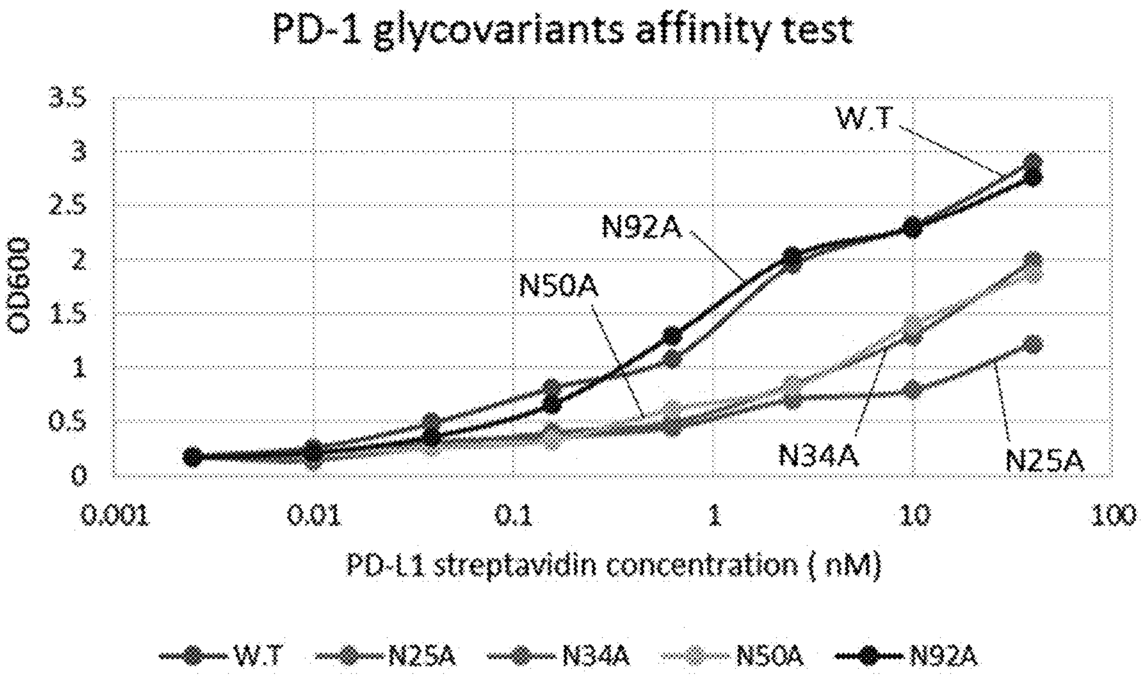
FIG. 2 shows a result of investigating the binding affinity of wild-type PD-1 and four PD-1 variants to PD-L1.

In order to verify that the glycosylation of human PD-1 actually plays an important role in binding affinity to PD-L1, the effect of each glycosylation on the binding affinity was tested by deglycosylating the four glycosylation sites existing in PD-1. Because PD-1 has four N-glycosylation sites, four genes (N25A, N34A, N50A, N92A) were prepared by replacing each asparagine at the four sites with alanine. The DNA fragment encoding the outer membrane site (amino sequences L25-Q167) of PD-1 was amplified by PCR using a template gene (catalog number: HG10377-M) and primers (CKJ#1, CKJ#2) of PD-1 and Vent polymerase. The amplified DNA fragment was treated with BssHll and XbaI enzymes and was ligated into the pMaz vector, which is a vector for expression in animal cells, which was treated with the same enzymes. The sequences of the ligated plasmids were analyzed to identify a desired plasmid by individual colony analysis after transforming into Judet ((F-mcrA Δ(mrr-hsdRMS-mcrBC) φ80lacZΔM15 ΔlacX74 recA1 endA1 araD139 Δ(ara, leu)7697 galU galK A-rpsL nupG) *E. coli*. Primers (CKJ#3, CKJ#4, CKJ#5, CKJ#6, CKJ#7, CKJ#8, CKJ#9, CKJ#10) were designed to obtain variants with asparagine substituted with alanine through site-directed mutagenesis by QuikChange PCR using the plasmid. The DNA fragments containing the gene were amplified using the designed primers and Pfu Turbo polymerase (Agilent). The amplified genes were sequenced and confirmed after transforming into Judel. After transfecting animal cells (HEK293F) with the prepared vectors for expressing wild-type PD-1 (pMaz-wild-type PD-1-His tag) and PD-1 glycovariants (pMaz-N25A PD-1-His tag, pMaz-N34A PD-1-His tag, pMaz-N50A PD-1-His tag, pMaz-N92A PD-1-His tag) and culturing for 6 days, the cell culture was centrifuged at 6,000 rpm for 20 minutes and then the supernatant was filtered through a 0.22-μm filter. The filtered supernatant was incubated with 1 mL of Ni-NTA resin (Qiagen) at 4° C. for 16 hours. The protein-bound resin was washed with 10 CV (column volume) of a PBS solution containing 10 mM imidazole (Sigma), and then washed again with 10 CV of a PBS solution containing 20 mM imidazole. Finally, an eluate was recovered with a PBS solution containing 250 mM imidazole (FIG. 1). The binding affinity of the wild-type PD-1 and four PD-1 glycovariants to PD-L1 was investigated by ELISA. Each protein was diluted with 0.05 M $Na_2CO_3$ (pH 9.6, Junsei) to 200 ng/well and then bound to a high-binding 96-well plate (Costar) at 4° C. for 16 hours. After removing the protein, each 96-well plate was incubated in a PBST (PBS containing 0.5% Tween 20) solution containing 5% skim milk solution at 5% (w/v) for 1 hour at room temperature. After discarding the upper solution and washing 4 times with 200 μL of a PBS solution containing 0.5% Tween 20, the PD-L1 tetramer was diluted with a PBS solution and then added to each 96-well plate and incubated for 1 hour at room temperature. After washing 4 times with 200 μL of a 0.5% PBST solution, anti-streptavidin-HRP (Genetex) diluted with PBS to 1:2,000 was added to each 96-well plate and incubated for 1 hour at room temperature. After discarding the upper solution and washing 4 times with 200 μL of a 0.5% PBST solution, reaction was initiated by adding 50 μL of TMB (Thermo Scientific) and was terminated after 20 minutes with 4 N $H_2SO_4$ (FIG. 2). As a result, whereas the N92A variant showed no significant difference in binding affinity from the wild-type PD-1, the remaining three glycovariants showed remarkable reduction in binding affinity, showing that the glycosylation of N25, N34 and N50 has a significant effect on the binding affinity to PD-L1.

TABLE 1

| SEQ ID NO | Primer | Sequence (5'→3') |
|---|---|---|
| SEQ ID NO 1 | CKJ#1 | GCGGAATTCGGCGCGCACTCCGAATTAGACTCCCC AGACAGGCCC |
| SEQ ID NO 2 | CKJ#2 | GAATTCCGCTCTAGATTATCAATGATGATGGTGGTG ATGTTGGAACTGGCCGGCTGG |
| SEQ ID NO 3 | CKJ#3 | CGTGGTGACCGAAGGGGACGCCGCCACCTTCACC TGCAGCT |
| SEQ ID NO 4 | CKJ#4 | AGCTGCAGGTGAAGGTGGCGGCGTCCCCTTCGGT CACCACG |
| SEQ ID NO 5 | CKJ#5 | ACCTTCACCTGCAGCTTCTCCGCCACATCGGAGAG CTTCGTGCTAAAC |
| SEQ ID NO 6 | CKJ#6 | GTTTAGCACGAAGCTCTCCGATGTGGCGGAGAAGC TGCAGGTGAAGGT |
| SEQ ID NO 7 | CKJ#7 | GTACCGCATGAGCCCCAGCGCCCAGACGGACAAG CTGGCCG |
| SEQ ID NO 8 | CKJ#8 | CGGCCAGCTTGTCCGTCTGGGCGCTGGGGCTCAT GCGGTAC |
| SEQ ID NO 9 | CKJ#9 | GTCAGGGCCCGGCGCGCCGACAGCGGCACCTACC TCTG |
| SEQ ID NO 10 | CKJ#10 | CAGAGGTAGGTGCCGCTGTCGGCGCGCCGGGCCC TGAC |
| SEQ ID NO 11 | Hw#1 | GCGGAATTCGGCGCGCACTCCGAATTTACTGTCAC GGTTCCCAAGGACC |
| SEQ ID NO 12 | Hw#2 | CTTGTGCCTTGCTATCTTTAGACGGGTCAGAGCCA CCGCCACCCCTTTCATTTGGAGGATGTGCCAGAG |
| SEQ ID NO 13 | HW#3 | GACCCGTCTAAAGATAGCAAGGCACAAG |

TABLE 1-continued

| SEQ ID NO | Primer | Sequence (5'→3') |
|---|---|---|
| SEQ ID NO 14 | HW#4 | GAATTCCGCTCTAGATCATTAGTGGTGATGATGGTGGTGAG |
| SEQ ID NO 15 | JY#1 | CGCAGCGAGGCCCAGCCGGCCTTAGACTCCCCAGACAGGCCC |
| SEQ ID NO 16 | JY#2 | CGCAGCGAGGCCCCCGAGGCCCCTTGGAACTGGCCGGCTGG |
| SEQ ID NO 17 | JY#3 | CGCAGCGAGGCCCAGCCGGCC |
| SEQ ID NO 18 | JY#4 | CGCAGCGAGGCCCCCGAGGCCCCC |

Primers Used in the Experiment

Example 2: Cloning of Tetrameric Human PD-L1 (PD-L1-Streptavidin) for PD-1 Engineering The cDNA of the human PD-L1 gene was purchased from Sino Biotech (Catalog number: HG10084-M) and the gene of the outer membrane of PD-L1 cells (amino sequences F19-R238) was amplified by PCR using primers (HW#1, HW#2) and Vent polymerase. Because the dissociation constant of wild-type PD-1 to wild-type PD-L1 is not good enough (equilibrium dissociation constant, $K_D$=~8.7 μM), avidity effect was induced through tetramerization for effective screening of aglycosylated PD-1 variants. The tetramerization was induced by expressing streptavidin at the C-terminal of PD-L1, and a GS linker was inserted between streptavidin and PD-L1 to ensure the flexibility of each protein. After amplifying the gene using primers (HW#3, HW#4) and Vent polymerase (New England Biolab), assembly PCR was conducted using the previously amplified PD-L1 gene and Vent polymerase. The prepared gene was treated with BssHII and XbaI restriction enzymes (New England Biolab). The restriction enzyme-treated PD-L1-streptavidin-His tag gene was ligated into a pMaz vector, which is a vector for mammalian expression, which had been treated with the same restriction enzymes. The ligated plasmid was transformed into Jude1 *E. coli*. Single clones were obtained and then it was confirmed through sequencing that the PD-L1-streptavidin-His tag was successfully inserted into the pMaz vector.

Example 3: Expression of Tetrameric PD-L1-Streptavidin in Animal Cells Purification, and Fluorescence Labeling The prepared vector for tetrameric PD-L1 expression was transfected into animal cells (HEK293F). After culturing the cells for 6 days, the cell culture was centrifuged at 6,000 rpm for 20 minutes and the supernatant was taken and filtered through a 0.22-μm filter. The filtered supernatant was induced to bind to 1 mL of Ni-NTA resin (Qiagen) at 4° C. for 16 hours. The bound resin was washed with 10 CV of a PBS solution containing 10 mM imidazole (Sigma) and then washed again with 10 CV of a PBS solution containing 20 mM imidazole. Finally, proteins were eluted and recovered with a PBS solution containing 250 mM imidazole. The purified PD-L1 tetramer was fluorescence-labeled using an Alexa-488 labeling kit. As a result of ELISA assay, the fluorescence-labeled tetrameric PD-L1 showed superior binding affinity to PD-1 (FIG. 3).

Example 4: Construction of Wild-Type PD-1, HAC-V PD-1 Expressing Plasmids for Displaying Human PD-1 in Inner Membrane of Bacterial Cells In order to display the outer membrane site of PD-1, the DNA of PD-1 (amino sequences L25-Q167) was amplified by PCR using primers (JY#1, JY#2) and Vent polymerase and then treated with a SfiI restriction enzyme. In order to immobilize PD-1 protein to the cellular inner membrane during the transport to the periplasmic region of *E. coli* through NlpA signal peptide, a pMopac12-NlpA-WTPD-1-FLAG vector was prepared by ligating SfiI-treated PD-1 DNA fragment with a SfiI fragment of pMopac12-NlpA-FLAG vector. For a HAC-V variant as a control group, a synthesized HAC-V DNA fragment was also cloned into SfiI site of pMopac12-NlpA-FLAG vector to construct pMopac12-NlpA-HAC-V PD-1-FLAG. Then, after transforming into *E. coli* Jude1 and obtaining single clones, it was confirmed through sequencing that wild-type PD-1 and HAC-V PD-1 were successfully inserted into the pMopac-12 vector.

Figure 4:
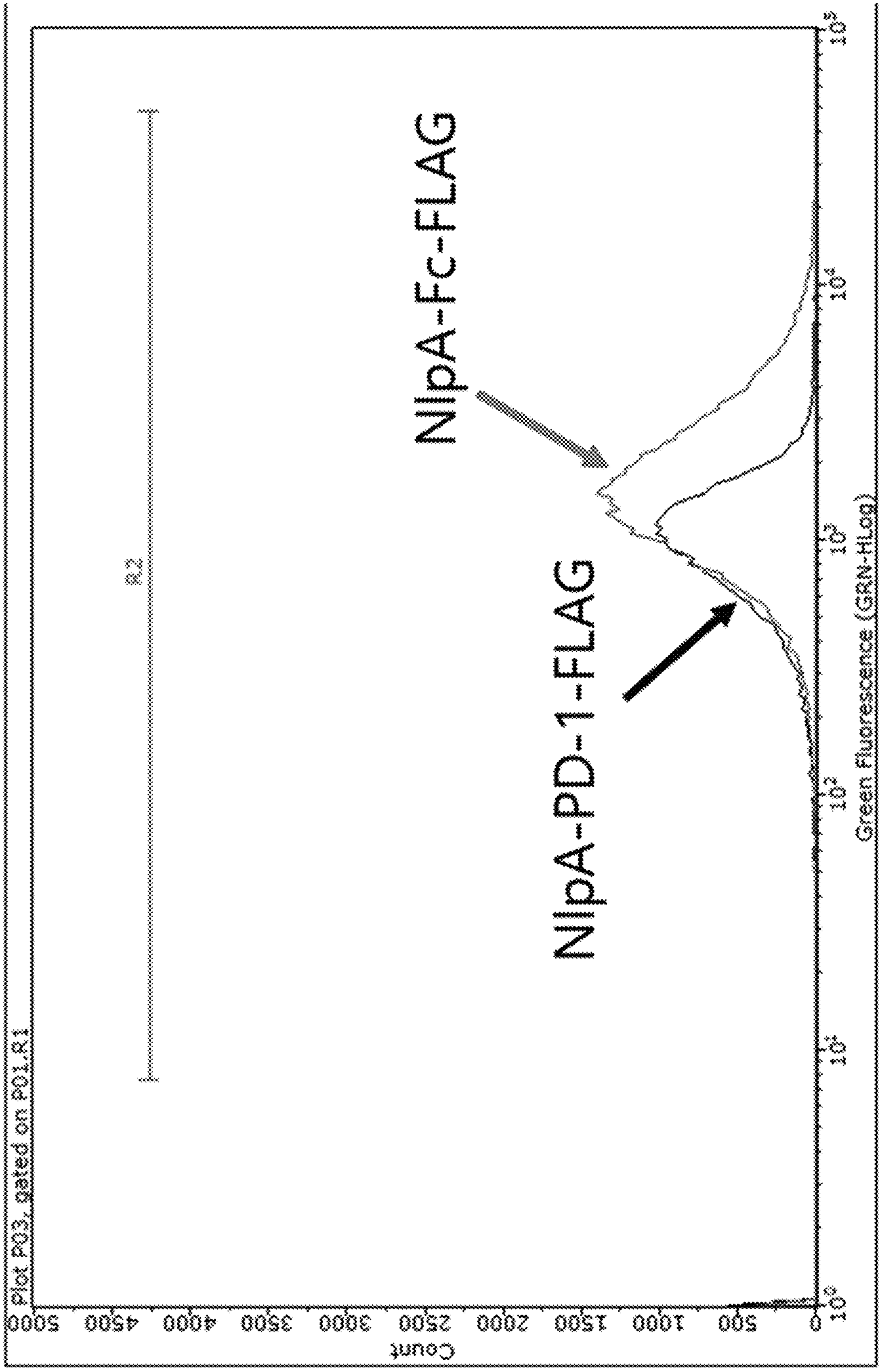
FIG. 4 shows a result of analyzing the expression of aglycosylated PD-1 in *E. coli* using anti-FLAG-FITC.
Figure 5:
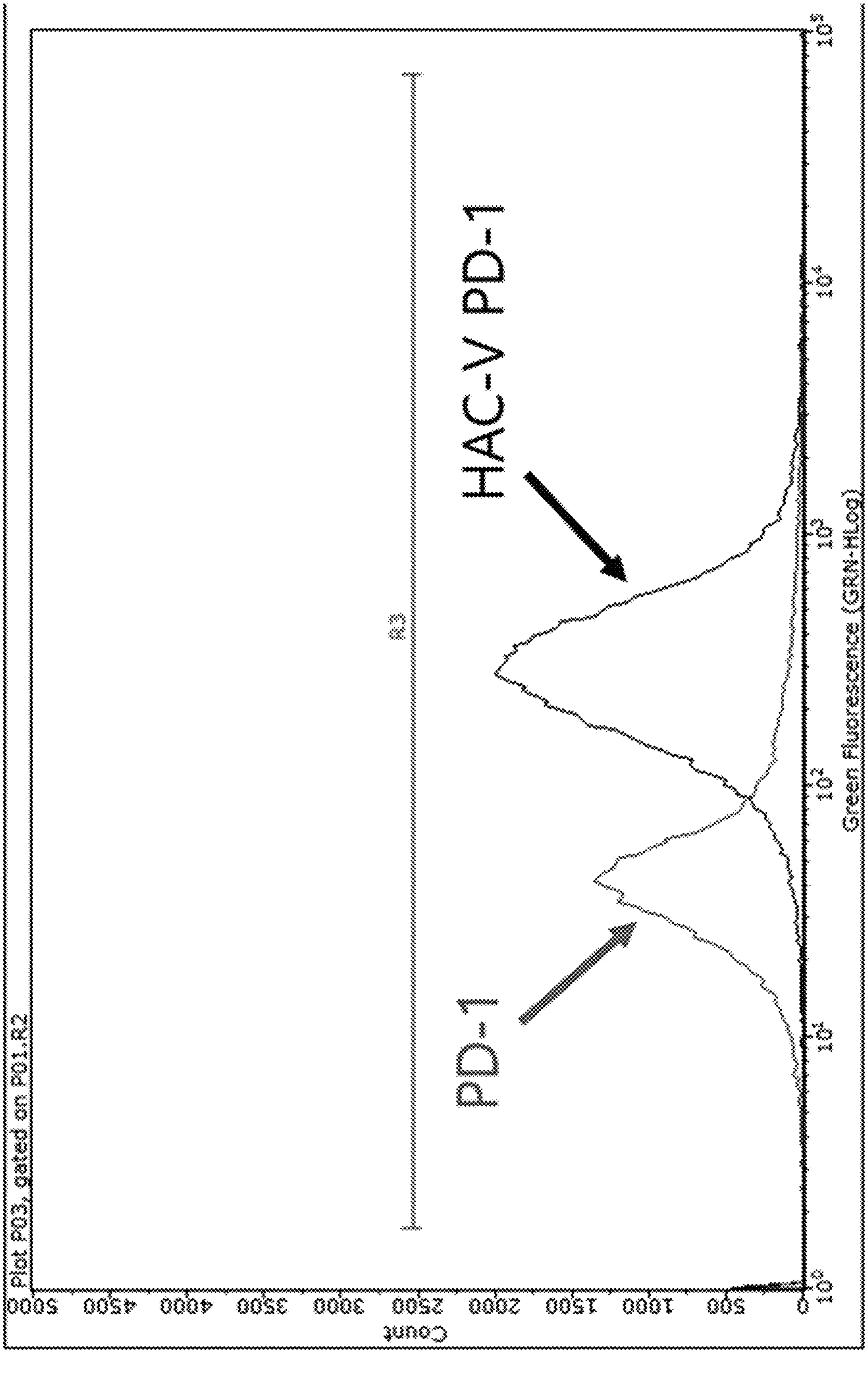
FIG. 5 shows a result of measuring the activation of aglycosylated PD-1s.

Example 5: Verification of Expression of PD-1 and PD-1 Variants (Wild-Type PD-1, HAC-V PD-1) in *E. coli* and Binding Affinity to PD-L1 by Flow Cytometry Each of the plasmids (pMopac12-NlpA-PD-1-FLAG, pMopac12-NlpA-HAC-V PD-1-FLAG, pMopac12-NlpA-Fc-FLAG) prepared through cloning was transformed into Jude1. Each of the prepared samples was cultured in a TB medium containing 2% glucose and 40 μg/mL chloramphenicol at 37° C. and 250 rpm for 16 hours. The cultured cells were inoculated into 6 mL of a TB medium containing 40 μg/mL chloramphenicol at a ratio of 1:50. After culturing to $OD_{600}$=0.5, followed by cooling for 20 minutes at 25° C. and 250 rpm, the protein overexpression was induced at 25° C. and 250 rpm for 5 hours by adding 1 mM IPTG. The same number of the protein-overexpressing *E. coli* was added to an e-tube through $OD_{600}$ normalization and the cells were recovered through centrifugation at 14,000 rpm for 1 minute. In order to remove the remaining medium, the cells were washed twice through resuspension of the pellet in 1 mL of 10 mM Tris-HCl (pH 8.0) and centrifugation at 13,500 rpm for 1 minute. The cells were resuspended in 1 mL of STE [0.5 M sucrose, 10 mM Tris-HCl, 10 mM EDTA (pH 8.0)] solution and rotated at 37° C. for 30 minutes to remove the outer membrane of the cells. After collecting *E. coli* by centrifuging at 13,500 rpm for 1 minute, the supernatant was removed. The *E. coli* cell pellet was resuspended in 1 mL of solution A [0.5 M sucrose, 20 mM $MgCl_2$, 10 mM MOPS, pH 6.8] and then centrifuged at 13,500 rpm for 1 minute. After resuspending the cell pellet by adding 1 mL of a solution prepared by mixing 1 mL of solution A with 20 µL of a 50 mg/mL lysozyme solution, a peptidoglycan layer was removed by rotating at 37° C. for 15 minutes. After the centrifugation, the supernatant was removed. After resuspending the pellt in 1 mL of PBS, 300 µL was taken and added by 700 µL of PBS, 12.5 nM of a tetrameric PD-L1-Alexa488 probe and 33 nM of anti-FLAG-FTIC (Sigma). Then, spheroplasts were labeled with the fluorescent probe by rotating at room temperature. After conducting the labeling process for 1 hour, centrifugation was performed at 13,500 rpm for 1 minute. After discarding the supernatant, the cells were washed once with 1 mL of PBS and then centrifuged again at 13,500 rpm for 1 minute. The cells were resuspended in 1 mL of PBS and then analyzed using the Guava instrument (Merck Millipore). As a result, it was confirmed that the aglycosylated PD-1 was expressed well in *E. coli* (FIG. 4) but did not show binding affinity to PD-L1. It was also confirmed that the aglycosylated HAC-V PD-1 show weak binding affinity to PD-L1 (FIG. 5).

Figure 6:
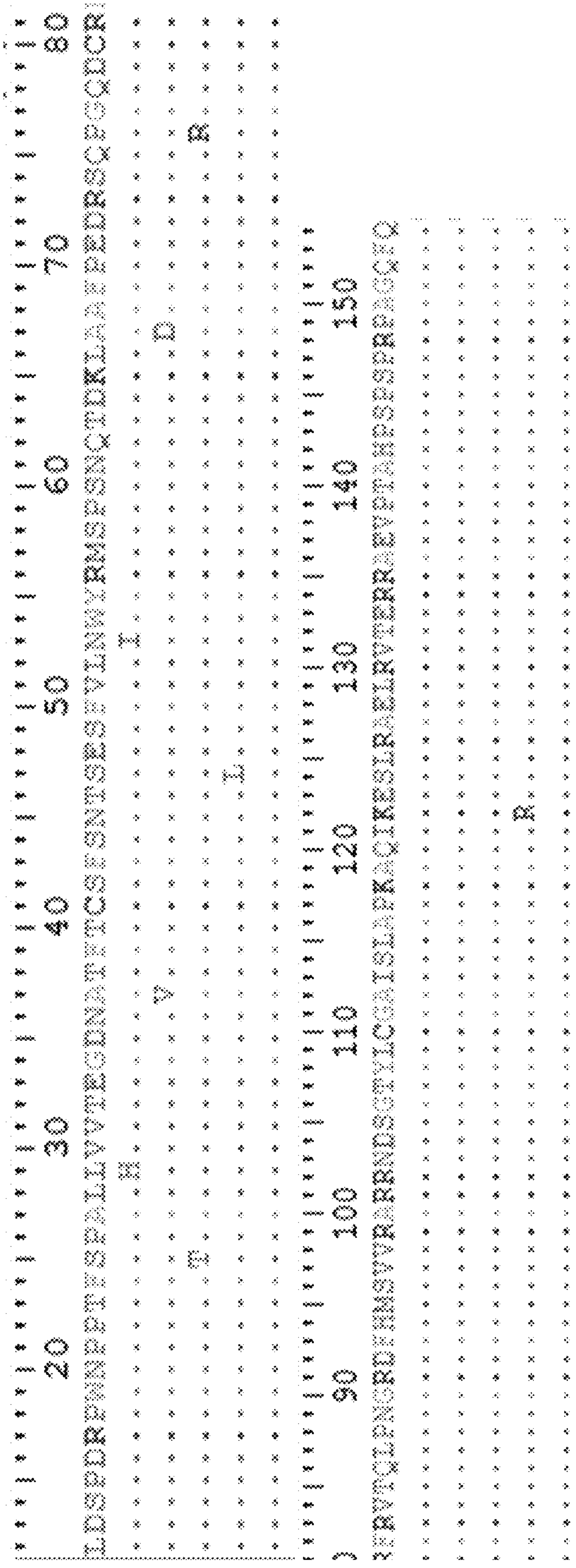
FIG. 6 shows the amino sequences of an established primary library.

Example 6: Construction of Error-Prone PD-1 Library for Use in High-Throughput Screening For high-throughput screening of aglycosylated PD-1 showing high binding affinity to PD-L1, primers having SfiI sites on both sides (JY#3, JY#4) were designed such that errors can be inserted in all the sites of PD-1 during PCR-based amplification using pMopac12-NIpA-PD-1-FLAG as a template. In order to construct a library using the designed primers, Taq polymerase (Takara), dNTPs (Invitrogen), $MgCl_2$ and $MnCl_2$ (Sigma), the gene was amplified by error-prone PCR. The PCR product was treated with the SfiI enzyme, ligated to a SfiI fragment of pMopac12-NIpA-FLAG vector, and then transformed into Jude1 cells. The transformed *E. coli* cells were spread onto a square plate and cultured at 37° C. for 16 hours. Then, a primary library was obtained by recovering the *E. coli* cells with TB containing 2% glucose (FIG. 6).

Example 7: Screening of PD-1 Variant by Flow Cytometry Sorting

After adding 40 µg/mL chloramphenicol to 25 mL of a TB medium containing 2% glucose, the constructed *E. coli* library was inoculated to a 250-mL flask and incubated at 37° C. and 250 rpm for 4 hours. Then, the *E. coli* cells were inoculated to 100 mL of a TB medium containing 40 µg/mL chloramphenicol at a ratio of 1:100. After culturing to $OD_{600}$=0.5, followed by cooling for 20 minutes at 25° C. and 250 rpm, protein overexpression was induced at 25° C. and 250 rpm for 5 hours by adding 1 mM IPTG, and the cells were recovered by centrifuging at 14,000 rpm for 1 minute. In order to remove the remaining medium, the cells were resuspended in 1 mL of 10 mM Tris-HCl (pH 8.0), centrifuged at 13,500 rpm for 1 minute and then washed. This procedure was repeated 2 times. The cells were resuspended in 1 mL of STE [0.5 M sucrose, 10 mM Tris-HCl, 10 mM EDTA (pH 8.0)] solution and rotated at 37° C. for 30 minutes to remove the outer membrane of the cells. After collecting *E. coli* by centrifuging at 13,500 rpm for 1 minute, the supernatant was removed. The cells were resuspended in 1 mL of solution A [0.5 M sucrose, 20 mM $MgCl_2$, 10 mM MOPS, pH 6.8] and then centrifuged at 13,500 rpm for 1 minute. After resuspending the cells by adding 1 mL of a solution prepared by mixing 1 mL of solution A with 20 µL of a 50 mg/mL lysozyme solution, a peptidoglycan layer was removed by rotating at 37° C. for 15 minutes. After the centrifugation, the supernatant was removed. After resuspending the cells in 1 mL of PBS, 300 µL was taken and 700 µL of PBS and 12.5 nM of a tetrameric PD-L1-Alexa488 probe were added. Then, spheroplasts were labeled with the fluorescent probe by rotating at room temperature. After conducting the labeling process for 1 hour, centrifugation was performed at 13,500 rpm for 1 minute. After discarding the supernatant, the cells were washed once with 1 mL of PBS and then centrifuged again at 13,500 rpm for 1 minute. From the cells resuspended in 1 mL of PBS, *E. coli* cells with high binding affinity to PD-L1 were chosen and recovered using an S3 sorter (Bio-Rad). Genes were obtained from the recovered *E. coli* by PCR using primers (JY#1, JY#2). The genes were treated with the SfiI restriction enzyme and then ligated to SfiI fragment of pMopac12-NIpA-FLAG vector. The resulting plasmid was transformed into Jude1 and the cells were spread onto a square plate. After incubation at 37° C. for 16 hours, the cells were recovered and stored in a deep freezer. This screening procedure was repeated 5 more times.

Example 8: Culturing of *E. coli* for Investigation of Enrichment of PD-1 Variants with Increased Affinity for PD-L1

After adding 40 µg/mL chloramphenicol to 25 mL of TB containing 2% glucose, a primary library, a 1st-round library, a 2vd-round library, a 3rd-round library, a 4th-round library, a 5th-round library and a 6th-round library were added to a 250-mL flask. After incubation at 37° C. and 250 rpm for 4 hours, *E. coli* cultured in 100 mL of TB containing 40 µg/mL chloramphenicol was inoculated at a ratio of 1:100. After culturing to $OD_{600}$=0.5, followed by cooling for 20 minutes at 25° C. and 250 rpm, protein overexpression was induced at 25° C. and 250 rpm for 5 hours by adding 1 mM IPTG. In addition, wild-type PD-1 and HAC-V-PD-1 expressing cells for use as a control group were inoculated into 4 mL of a TB medium containing 2% glucose and 40 µg/mL chloramphenicol and grown at 37° C. and 250 rpm for 16 hours. The cultured cells were inoculated to 6 mL of a TB medium containing 40 µg/mL chloramphenicol at a ratio of 1:50. After culturing to $OD_{600}$=0.5, followed by cooling for 20 minutes at 25° C. and 250 rpm, protein overexpression was induced at 25° C. and 250 rpm for 5 hours by adding 1 mM IPTG. The same number of the *E. coli* was added to an e-tube through $OD_{600}$ normalization and the cells were recovered through centrifugation at 14,000 rpm for 1 minute.

Figure 7:
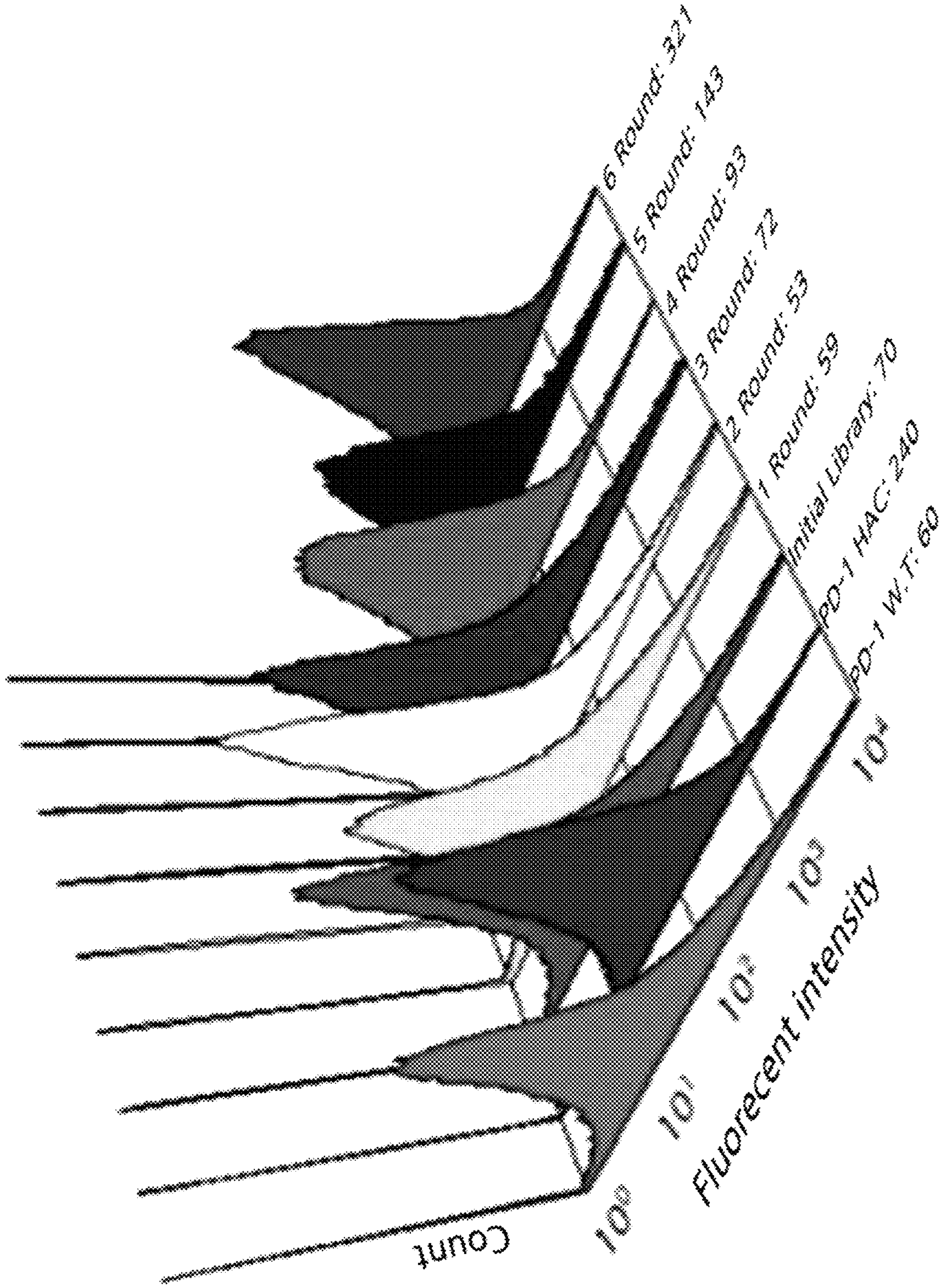
FIG. 7 shows the result of library enrichment by flow cytometry.

Example 9: Investigation of Enrichment of PD-1 Variants with Increased Affinity for PD-L1 by Flow Cytometry In order to remove the remaining medium, the cells that had been added to an e-tube were resuspended in 1 mL of 10 mM Tris-HCl (pH 8.0), centrifuged at 13,500 rpm for 1 minute and then washed. This procedure was repeated 2 times. The cells were resuspended in 1 mL of STE [0.5 M sucrose, 10 mM Tris-HCl, 10 mM EDTA (pH 8.0)] solution and rotated at 37° C. for 30 minutes to remove the outer membrane of the cells. After collecting *E. coli* by centrifuging at 13,500 rpm for 1 minute, the supernatant was removed. The cell pellet was resuspended in 1 mL of solution A [0.5 M sucrose, 20 mM $MgCl_2$, 10 mM MOPS, pH 6.8] and then centrifuged at 13,500 rpm for 1 minute. After resuspending the cells by adding 1 mL of a solution prepared by mixing 1 mL of solution A with 20 μL of a 50 mg/mL lysozyme solution, a peptidoglycan layer was removed by rotating at 37° C. for 15 minutes. After the centrifugation, the supernatant was removed. After resuspending in 1 mL of PBS, 300 μL was taken and 700 μL of PBS and 12.5 nM of a tetrameric PD-L1-Alexa488 probe were added together. Then, spheroplasts were labeled with the fluorescent probe by rotating at room temperature. After conducting the labeling process for 1 hour, centrifugation was performed at 13,500 rpm for 1 minute. After discarding the supernatant, the cell pellet was washed once with 1 mL of PBS and then centrifuged again at 13,500 rpm for 1 minute. After resuspending the cells in 1 mL of PBS, the binding affinity to PD-L1 was analyzed by measuring mean fluorescence intensity (MFI) using a flow cytometer (Guava, Millipore). It was confirmed that variants with higher binding affinity to PD-L1 were amplified from the libraries as the screening proceeded (FIG. 7).

Figure 8:
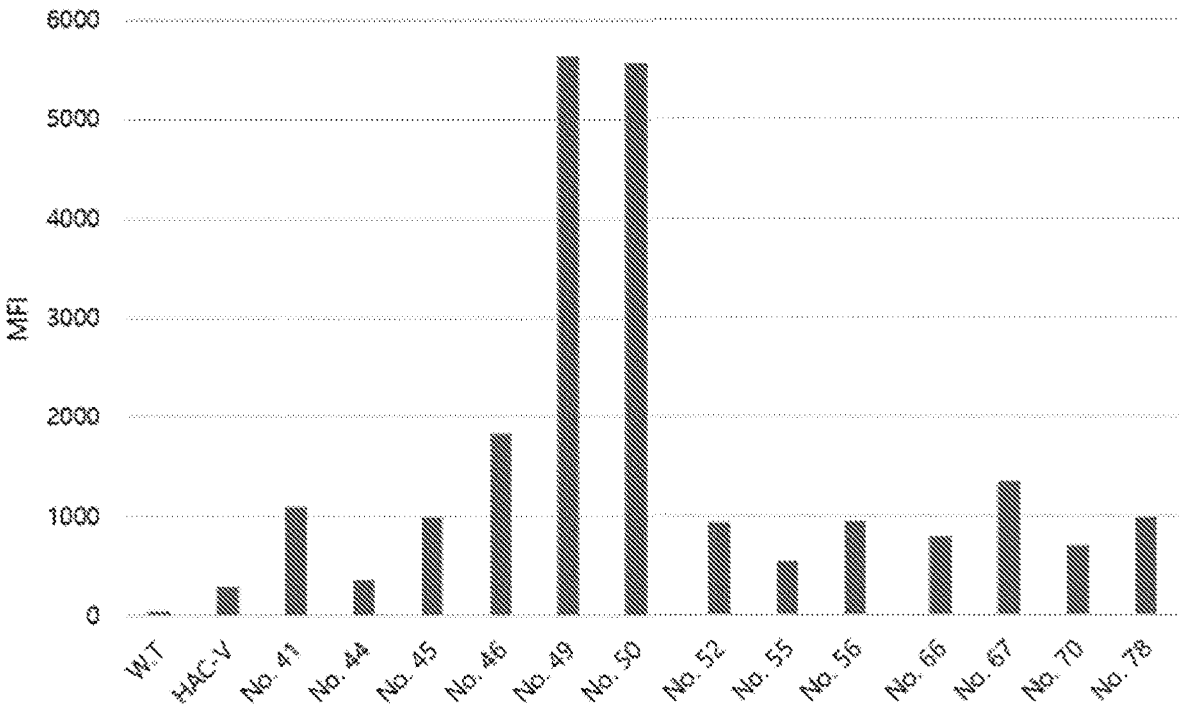
FIG. 8 shows a result of analyzing the binding affinity of *E. coli* cells displaying aglycosylated PD-1 variants to PD-L1.
Figure 9:
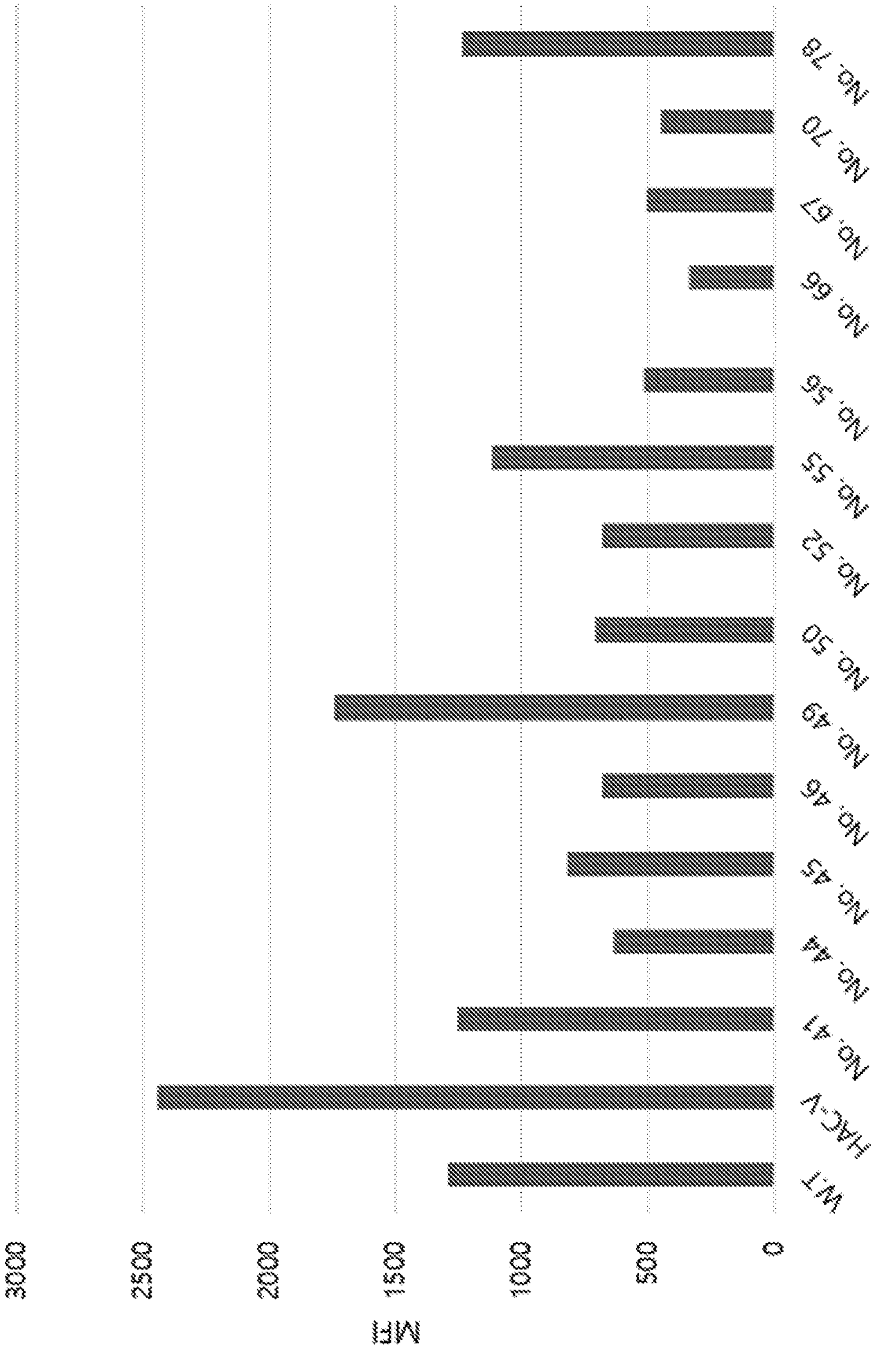
FIG. 9 shows a result of analyzing the protein expression level in *E. coli* cells displaying aglycosylated PD-1 variants using anti-FLAG-FITC.

Example 10: Securing of PD-1 Variants Having Improved Binding Affinity to PD-L1 by Flow Cytometry The individual colonies from the final round were inoculated to a TB medium containing 2% glucose and 40 μg/mL chloramphenicol and then cultured at 37° C. and 250 rpm for 16 hours. The cultured cells were inoculated to 6 mL of a TB medium containing 40 μg/mL chloramphenicol by diluting to a ratio of 1:50. After culturing to $OD_{600}$=0.5, followed by cooling for 20 minutes at 25° C. and 250 rpm, the protein overexpression was induced at 25° C. and 250 rpm for 5 hours by adding 1 mM IPTG. The same number of the *E. coli* was added to an e-tube through $OD_{600}$ normalization and the cells were recovered through centrifugation at 14,000 rpm for 1 minute. In order to remove the remaining medium, the cells that had been added into the e-tube were resuspended in 1 mL of 10 mM Tris-HCl (pH 8.0), centrifuged at 13,500 rpm for 1 minute and then washed. This procedure was repeated 2 times. The cells were resuspended in 1 mL of STE [0.5 M sucrose, 10 mM Tris-HCl, 10 mM EDTA (pH 8.0)] solution and rotated at 37° C. for 30 minutes to remove the outer membrane of the cells. After collecting cells by centrifuging at 13,500 rpm for 1 minute, the supernatant was removed. The cell pellet was resuspended in 1 mL of solution A [0.5 M sucrose, 20 mM $MgCl_2$, 10 mM MOPS, pH 6.8] and then centrifuged at 13,500 rpm for 1 minute. After resuspending the cells by adding 1 mL of a solution prepared by mixing 1 mL of solution A with 20 μL of a 50 mg/mL lysozyme solution, a peptidoglycan layer was removed by rotating at 37° C. for 15 minutes. After the centrifugation, the supernatant was removed. After resuspending in 1 mL of PBS, 300 μL was taken and 700 μL of PBS and 12.5 nM of a tetrameric PD-L1-Alexa488 probe were added together. Then, spheroplasts were labeled with the fluorescent probe by rotating at room temperature. After conducting the labeling process for 1 hour, centrifugation was performed at 13,500 rpm for 1 minute. After discarding the supernatant, the cells were washed once with 1 mL of PBS and then centrifuged again at 13,500 rpm for 1 minute. The cells were resuspended in 1 mL of PBS and the binding affinity to PD-L1 was analyzed by measuring fluorescence signals using the Guava instrument (FIG. 8). In addition, as the expression level of the PD-1 protein displayed by *E. coli* can affect fluorescence intensity, it was necessary to determine the expression level of PD-1. For this, 300 μL of the *E. coli*, remained after resuspending in PBS, was added to 700 μL of PBS and 1 μL of anti-FLAG-FITC and rotated at room temperature to label spheroplasts with the fluorescent probe. After conducting the labeling process for 1 hour, centrifugation was performed at 13,500 rpm for 1 minute. After discarding the supernatant, the cells were washed once with 1 mL of PBS and then centrifuged again at 13,500 rpm for 1 minute. The cells were resuspended in 1 mL of PBS and the binding affinity to anti-FLAG-FITC was analyzed by measuring fluorescence signals by flow cytometry (FIG. 9).

TABLE 2

| SEQ ID NO | PD-1 variant | Location of PD-1 variant and substituted amino acids |
|---|---|---|
| SEQ ID NO 48 | No. 41 (CKJ 41) | S36P/C69S/L114P |
| SEQ ID NO 50 | No. 45 (CKJ 45) | S36P/C69S/K107N/L114P/F142L |
| SEQ ID NO 51 | No. 46 (CKJ 46) | S36P/C69S/L114P/P132L |
| SEQ ID NO 56 | No. 56 (CKJ 56) | S36P/C69S/N92K/L114P/H131R |
| SEQ ID NO 58 | No. 67 (CKJ 67) | N34T/S36P/C69S/L114P |
| SEQ ID NO 59 | No. 70 (CKJ 70) | S36P/C69S |
| SEQ ID NO 60 | No. 78 (CKJ 78) | T12S/S36P/C69S/L114P |
| SEQ ID NO 49 | No. 44 (CKJ 44) | F13I/M46I/N50S/C69Y/V127A |
| SEQ ID NO 54 | No. 52 (CKJ 52) | F13I/M46I/C69Y |
| SEQ ID NO 52 | No. 49 (CKJ 49) | F13L/N25D/C69S/N92S/R137K |
| SEQ ID NO 53 | No. 50 (CKJ 50) | F13L/N25D/C69S/R88K/N92S/A125S |
| SEQ ID NO 55 | No. 55 (CKJ 55) | N25D/C69S/N92S/A101V |
| SEQ ID NO 57 | No. 66 (CKJ 66) | N9D/N25D/C69S/N92S/A101V |

PD-1 Variants Having Improved Binding Affinity to PD-L1

Example 11. Cloning for Comparison with PD-1 Variants of Additional Control Groups (PD-1 S.6.8.3 and S.5.1T)

For use as additional control groups, S.6.8.3 and S.5.1T variants were cloned through primer assembly PCR. First, after conducting primer assembly PCR using primers (S.6.8.3: JY#5,6,7,8,9,10,11,12/S.5.1T: JY#13,14,15,16,17, 18,19,20) and Vent polymerase, the assembled gene was amplified through Amplify PCR. The assembled gene was treated with SfiI and then ligated with SfiI fragment of pMopac12-NIpA-FLAG vector to construct pMopac12-NIpA-PD-1 S.6.8.3-FLAG and pMopac12-NIpA-PD-1 S.5.1T-FLAG vectors. Then, after obtaining single clones by transforming into *E. coli* Jude1, it was confirmed through sequencing that they were inserted successfully.

TABLE 3

| SEQ ID NO | Primer | Sequence (5'→3') |
|---|---|---|
| SEQ ID NO 62 | JY#5 | TTAGACTCCCCAGACAGGCCCTGGAACCCCCCCACC TTCTCCCCAGCCCTGCTCGTGGTGA |
| SEQ ID NO 63 | JY#6 | ACGAAGCTCTCCGATGTGTTGGAGAAGCTGCAGGTG AAGGTGGCGTTGTCCCCTTCGGTCACCACGAGCAGG GCT |

TABLE 3-continued

| SEQ ID NO | Primer | Sequence (5'→3') |
|---|---|---|
| SEQ ID NO 64 | JY#7 | AACACATCGGAGAGCTTCGTGCTAAACTGGTACCGCA TGAGCCCCAGCAACCAGACGGACAAGCTGGCCGCCT TC |
| SEQ ID NO 65 | JY#8 | TGGGCAGTTGTGTGACACGGAAGCGGCTGGCCTGGC CCAGCTGGCCGCGGTCCTCGGGGAAGGCGGCCAGC TTGT |
| SEQ ID NO 66 | JY#9 | CGTGTCACACAACTGCCCAACGGGCGTGACTTCCAC ATGAGCGTGGTCAGGGCCCGGCGCAGCGACAGCGG CACC |
| SEQ ID NO 67 | JY#10 | ACCCGCAGGCTCTCCCGGATCTGGATCCGGGGGGCC AGCAGGATGGCGCTACAGAGGTAGGTGCCGCTGTCG CTG |
| SEQ ID NO 68 | JY#11 | GGGAGAGCCTGCGGGTGGAGCTCAGGGTGACAGAG AGAAGGGCAGAAGTGCCCACAGCCCACCCCAGCCCC TCAC |
| SEQ ID NO 69 | JY#12 | TTGGAACTGGCCGGCTGGCCTGGGTGAGGGGCTGG GGTG |
| SEQ ID NO 70 | JY#13 | TTAGACTCCCCAGACAGGCCCTGGAACCCCCCCACC TTCTCCCCAGCCCTGCTCGTGGTGACCGAAGGGG |
| SEQ ID NO 71 | JY#14 | CAGTTTAGCACGAAGCTCTCCGATGTGTTGGAGAAGC TGCAGGTGAAGGTGGCGCTGTCCCCTTCGGTCACCA CG |
| SEQ ID NO 72 | JY#15 | GGAGAGCTTCGTGCTAAACTGGTACCGCATGAGCCC CAGCAACCAGGCCGACAAGCTGGCCGCCTTCCCCGA GGA |
| SEQ ID NO 73 | JY#16 | CACGCCCGTTGGGCAGTTGTGTGACACGGAAGCGGG AGTCCTGGCCGGGCTGGCTGCGGTCCTCGGGGAAG GCGG |
| SEQ ID NO 74 | JY#17 | CTGCCCAACGGGCGTGACTTCCACATGAGCGTGGTC GGGGCCCGGCGCTCCGACAGCGGCACCTACCTCTGT TCC |
| SEQ ID NO 75 | JY#18 | CTGAGCTCTGCCCGCAGGCTCTCCCGGATCTGCACC TTGGGGGCCAGGGAGATGGCGGAACAGAGGTAGGT GCCG |
| SEQ ID NO 76 | JY#19 | CTGCGGGCAGAGCTCAGGGTGGCAGAGAGAAGGGC AGAAGTGCCCACAGCCCACCCCAGCCCCTCACCCAG GCCA |
| SEQ ID NO 77 | JY#20 | TTGGAACTGGCCGGCTGGCCTGGGTGAGGGG |
| SEQ ID NO 78 | JY#21 | CCCCAGCCCCTCACCCAGGCCAGCCGGCCAGTTCC |
| SEQ ID NO 79 | JY#22 | GGAACTGGCCGGCTGGCCTGGGTGAGGGGCTGGGG |

Primers Used in Additional Experiments

Figure 10:
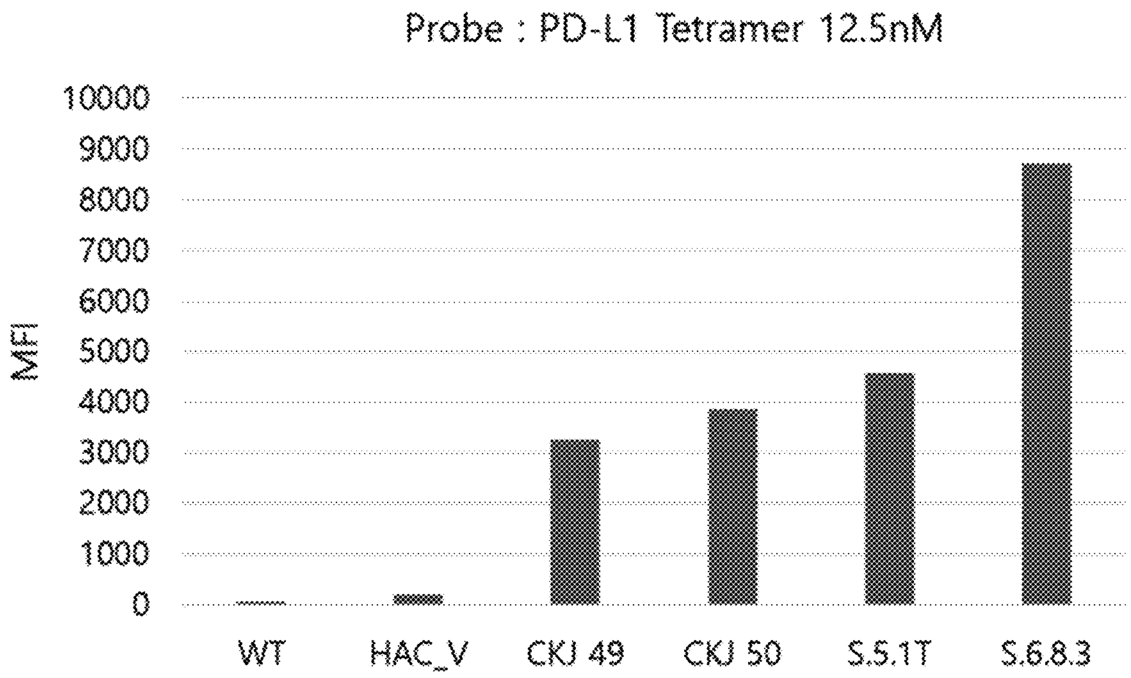
FIG. 10 shows a result of analyzing the binding affinity of *E. coli* cells displaying aglycosylated PD-1 variants to PD-L1.
Figure 11:
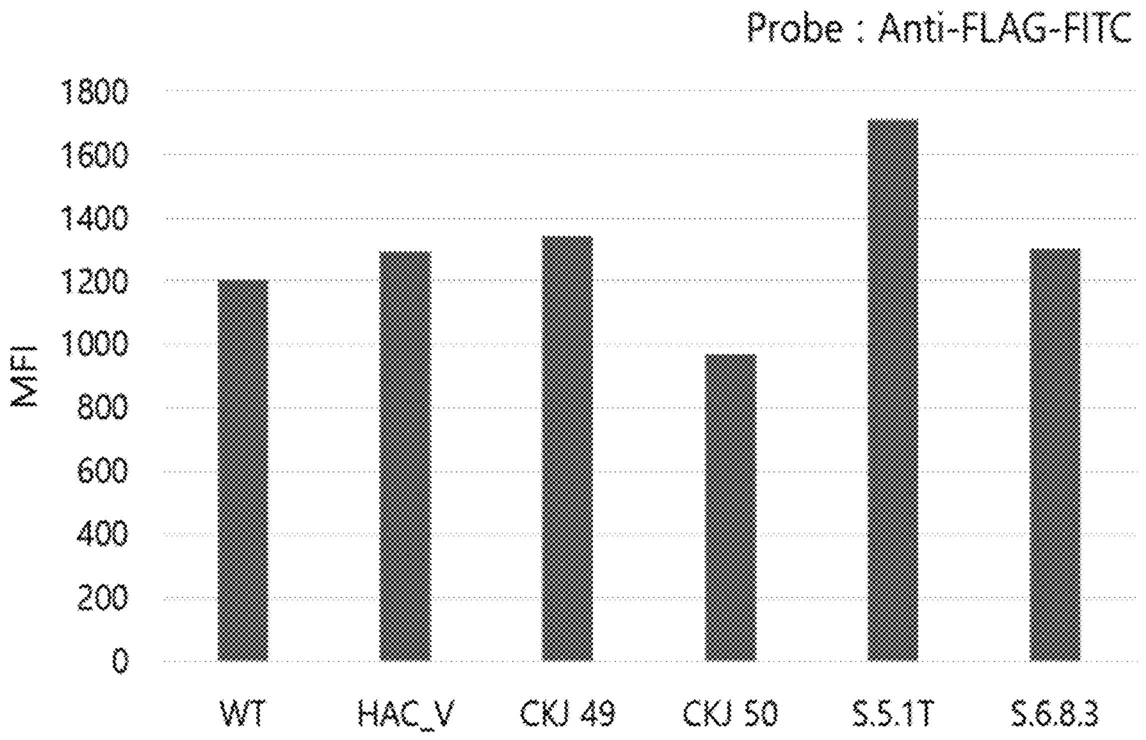
FIG. 11 shows a result of analyzing the protein expression level in *E. coli* cells displaying aglycosylated PD-1 variants using anti-FLAG-FITC.

Example 12. Comparison of Screened PD-1 Variants with Control Groups in Binding Affinity to PD-L1 by Flow Cytometry In order to compare the binding affinity to PD-L1 of PD-1 variants having high binding affinity with those of additional control groups, each of wild-type PD-1, PD-1 HAC-V, S.6.8.3 and S.5.1T, as control groups, CKJ 49 and CKJ 50 was inoculated to a TB medium containing 2% glucose and 40 μg/mL chloramphenicol and then cultured at 37° C. and 250 rpm for 16 hours. The cultured cells were inoculated to 6 mL of a TB medium containing 40 μg/mL chloramphenicol by diluting to a ratio of 1:100. After culturing to $OD_{600}$=0.5, followed by cooling for 20 minutes at 25° C. and 250 rpm, the protein overexpression was induced at 25° C. and 250 rpm for 5 hours by adding 1 mM IPTG. The same number of the *E. coli* was added to an e-tube through $OD_{600}$ normalization and the cells were recovered through centrifugation at 14,000 rpm for 1 minute. After conducting spheroplasting in the same manner as described in Example 5, 12.5 nM of a tetrameric PD-L1-Alexa488 probe was added to the prepared spheroplasts and they were labeled with the fluorescent probe by rotating at room temperature. After conducting the labeling process for 1 hour, centrifugation was performed at 13,500 rpm for 1 minute. After discarding the supernatant, the cells were washed once with 1 mL of PBS and then centrifuged again at 13,500 rpm for 1 minute. The cells were resuspended in 1 mL of PBS and the binding affinity to PD-L1 was analyzed by measuring fluorescence using the Guava instrument (FIG. 10). In addition, because the expression level of the PD-1 protein displayed by *E. coli* can affect fluorescence intensity, the expression level of PD-1 was determined. For this, 300 μL of the *E. coli* remaining after resuspending in PBS was taken and 700 μL of PBS and 1 μL of anti-FLAG-FITC were added together and spheroplasts were labeled with the fluorescent probe by rotating at room temperature. After conducting the labeling process for 1 hour, centrifugation was performed at 13,500 rpm for 1 minute. After discarding the supernatant, the cells were washed once with 1 mL of PBS and then centrifuged again at 13,500 rpm for 1 minute. The cells were resuspended in 1 mL of PBS and the binding affinity to anti-FLAG-FITC was analyzed by measuring fluorescence signals by flow cytometry (FIG. 11).

Example 13. Cloning for Screening of Variants Having Novel Mutations

In order to screen variants having novel mutations of CKJ 41, which has the newest mutation and high binding affinity from among the screened variants, the C69S in CKJ 41 was substituted with several amino acids (C, T, Y, A, G). For this, genes were amplified by Quikchange PCR using designed primers and Pfu Turbo polymerase (Agilent). The amplified genes were transformed into Jude1 and then analyzed by sequencing.

Example 14. Screening of Variants Having Novel Mutations by Flow Cytometry

Figure 12:
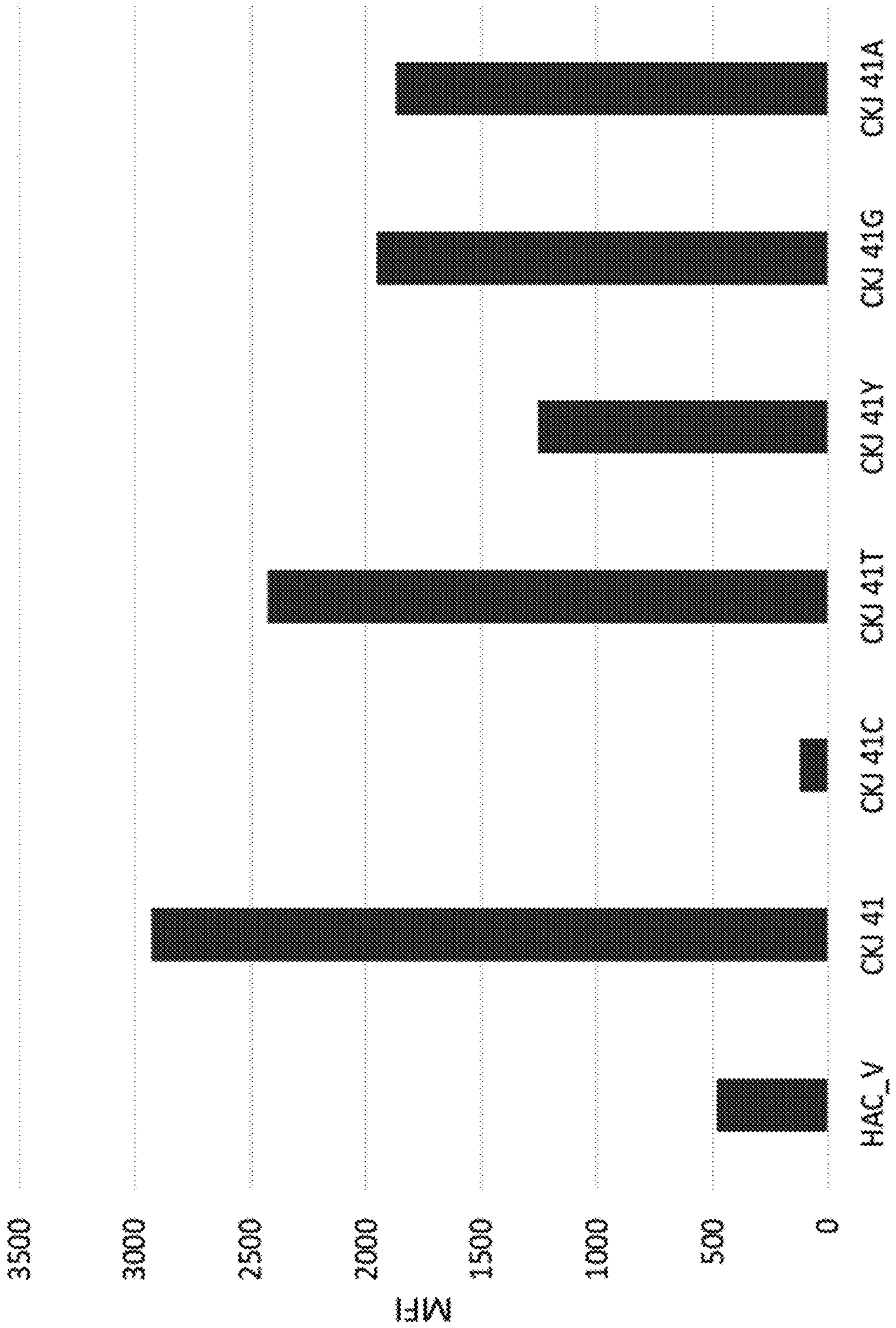
FIG. 12 shows a result of screening variants having novel mutations on CKJ 41.

CKJ 41, the HAC-V variant (control group) and CKJ 41C, CKJ 41T, CKJ 41Y, CKJ 41A, and CKJ 41G, wherein the 69th amino acid of CKJ 41 had been changed, were inoculated into TB medium containing 2% glucose and 40 μg/mL chloramphenicol and were cultured at 37° C. and 250 rpm for 16 hours. The cultured cells were inoculated again to 6 mL of a TB medium containing 40 μg/mL chloramphenicol by diluting to 1:100. After culturing to $OD_{600}$=0.5, followed by cooling for 20 minutes at 25° C. and 250 rpm, the protein overexpression was induced at 25° C. and 250 rpm for 5 hours by adding 1 mM IPTG. The same quantity of the *E. coli* was added to an e-tube through $OD_{600}$ normalization and the cells were recovered through centrifugation at 14,000 rpm for 1 minute. After conducting spheroplasting in the same manner as described in Example 5, 12.5 nM of a tetrameric PD-L1-Alexa488 probe was added to the prepared spheroplasts and they were labeled with the fluorescent probe by rotating at room temperature. After conducting the labeling process for 1 hour, centrifugation was performed at 13,500 rpm for 1 minute. After discarding the supernatant, the cells were washed once with 1 mL of PBS and then centrifuged again at 13,500 rpm for 1 minute. The cells were resuspended in 1 mL of PBS and the binding affinity to PD-L1 was analyzed by measuring fluorescence using the Guava instrument (FIG. 12).

Figure 13:
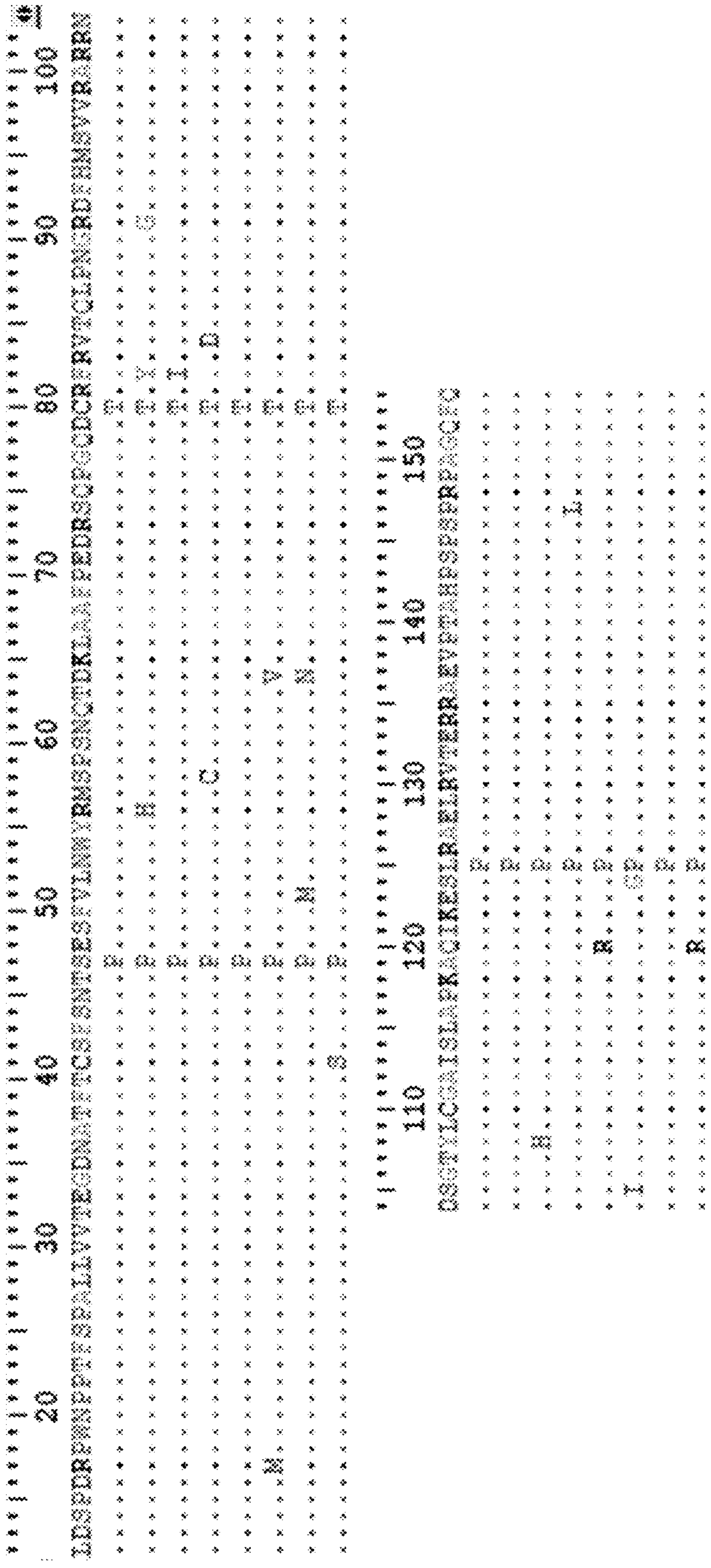
FIG. 13 shows the analysis of amino acid sequences of a secondary library established using CKJ 41T as a template.

Example 15. Construction of Secondary Error-Prone PD-1 Library for Securing PD-1 Variant Having Improved Binding Affinity For high-throughput screening of PD-1 showing higher binding affinity to PD-L1, inserts were prepared using pMopac12-NIpA-PD-1 CKJ 41T-FLAG, which exhibited less mutations but high fluorescence intensity, as a template such that errors can be inserted in all regions. A library was constructed by amplifying genes by error-prone PCR using primers having SfiI sites on both sides (JY#3, JY#4), Taq polymerase (Takara), dNTPs (Invitrogen), $MgCl_2$ and $MnCl_2$ (Sigma). The amplified genome was treated with the SfiI enzyme and ligated with SfiI fragment of pMopac12-NIpA-FLAG vector, and then transformed into Jude1 cells. The transformed *E. coli* cells were spread onto a square plate and cultured at 37° C. for 16 hours. Then, a primary library was prepared by recovering the *E. coli* cells with TB containing 2% glucose (FIG. 13).

Example 16. Secondary Screening of PD-1 Variant by Flow Cytometry Sorting

After adding 40 μg/mL chloramphenicol to 25 mL of a TB medium containing 2% glucose, the constructed library was inoculated to a 250-mL flask and incubated at 37° C. and 250 rpm for 4 hours. Then, the *E. coli* was inoculated to 100 mL of a TB medium containing 40 μg/mL chloramphenicol at a ratio of 1:100. After culturing to $OD_{600}$=0.5, followed by cooling for 20 minutes at 25° C. and 250 rpm, protein overexpression was induced at 25° C. and 250 rpm for 5 hours by adding 1 mM IPTG, and the cells were recovered by centrifuging at 14,000 rpm for 1 minute. After conducting spheroplasting in the same manner as described in Example 5, 12.5 nM of a tetrameric PD-L1-Alexa488 probe was added and rotated at room temperature to label the prepared spheroplasts. After conducting the labeling process for 1 hour, centrifugation was performed at 13,500 rpm for 1 minute. After discarding the supernatant, the cells were washed once with 1 mL of PBS and then centrifuged again at 13,500 rpm for 1 minute. The cells were resuspended in 1 mL of PBS and *E. coli* cells with higher binding affinity to PD-L1 were recovered using an S3 sorter (Bio-Rad). Genes were prepared from the recovered *E. coli* by PCR using primers (JY#3, JY#4)). The genes were treated with the SfiI restriction enzyme and then ligated to SfiI fragment of pMopac12-NIpA-FLAG vector. The resulting plasmid was transformed into Jude1 and the *E. coli* was spread onto a square plate. After incubation at 37° C. for 16 hours, the cells were recovered and stored in a deep freezer. This screening procedure was repeated 3 more times while gradually lowering the concentration of the probe.

Example 17. Culturing of *E. coli* for Investigation of Enrichment of Secondary PD-1 Variants with Increased Affinity for PD-L1

After adding 40 μg/mL chloramphenicol to 25 mL of TB containing 2% glucose, a primary library, a 1-round library, a 2-round library, a 3-round library and a 4-round library were added to a 250-mL flask. After incubation at 37° C. and 250 rpm for 4 hours, *E. coli* cultured in 100 mL of TB containing 40 μg/mL chloramphenicol was inoculated at a ratio of 1:100. After culturing to $OD_{600}$=0.5, followed by cooling for 20 minutes at 25° C. and 250 rpm, protein overexpression was induced at 25° C. and 250 rpm for 5 hours by adding 1 mM IPTG. In addition, for use as a control group, 40 μg/mL chloramphenicol was added to 4 mL of a TB medium containing 2% glucose and, after inoculating wild-type PD-1 and HAC-V-PD-1 cells, respectively, the cells were cultured at 37° C. and 250 rpm for 16 hours. The cultured cells were inoculated to 6 mL of a TB medium containing 40 μg/mL chloramphenicol at 1:100. After culturing to $OD_{600}$=0.5, followed by cooling for 20 minutes at 25° C. and 250 rpm, protein overexpression was induced at 25° C. and 250 rpm for 5 hours by adding 1 mM IPTG. The same number of the *E. coli* was added to an e-tube through $OD_{600}$ normalization and the cells were recovered through centrifugation at 14,000 rpm for 1 minute.

Figure 14:
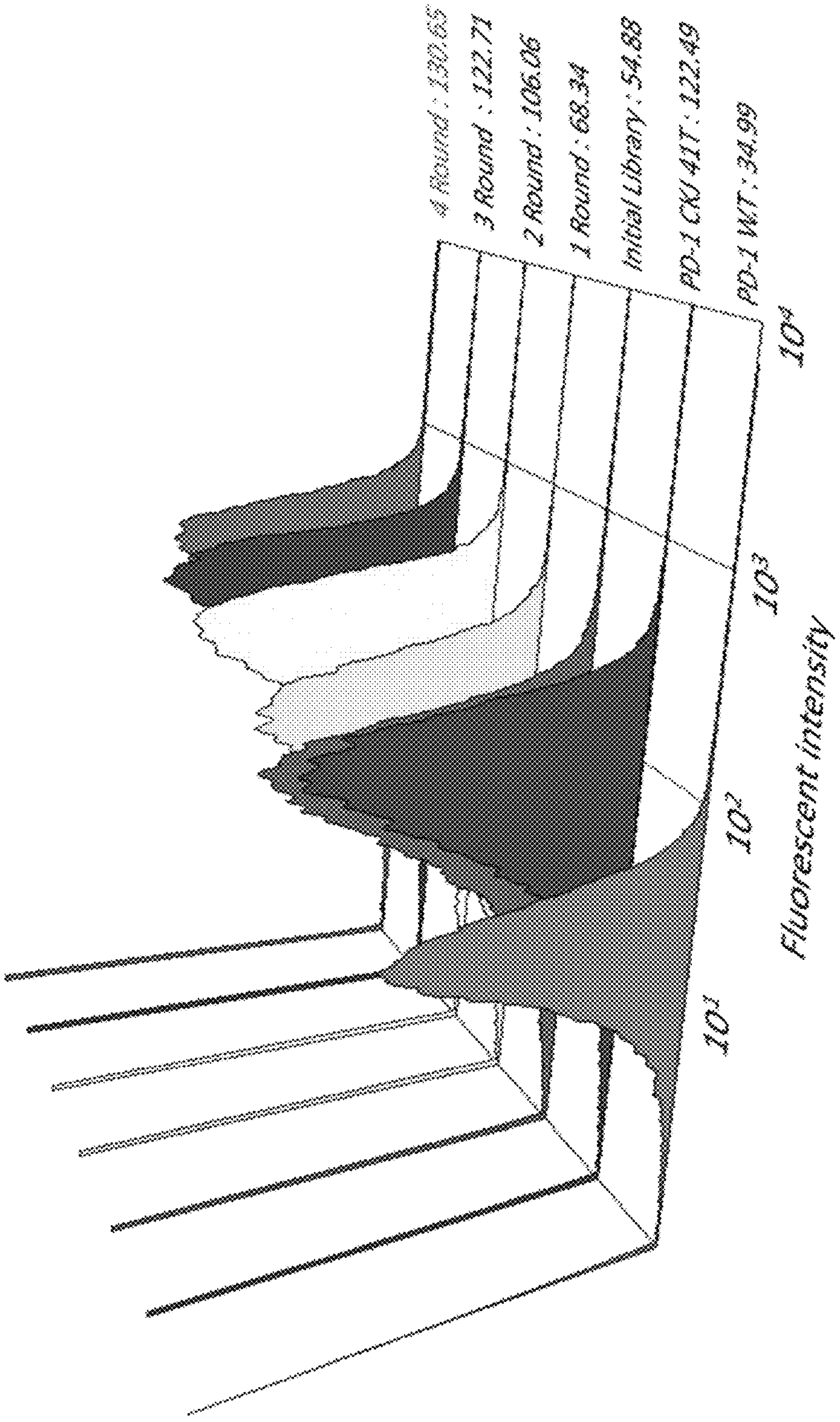
FIG. 14 shows a result of library enrichment by flow cytometry.

Example 18. Determination of Enrichment of PD-1 Variants with Increased PD-L1 Affinity by Flow Cytometry After conducting spheroplasting in the same manner as described in Example 5, 4 nM of a tetrameric PD-L1-Alexa488 probe was added to the prepared spheroplasts and rotated at room temperature for labeling. After conducting the labeling process for 1 hour, centrifugation was performed at 13,500 rpm for 1 minute. After discarding the supernatant, the cells were washed once with 1 mL of PBS and then centrifuged again at 13,500 rpm for 1 minute. The cells were resuspended in 1 mL of PBS and the binding affinity to PD-L1 was analyzed by measuring mean fluorescence intensity (MFI) using a flow cytometer (Guava, Millipore). It was confirmed that variants with higher binding affinity to PD-L1 were amplified from the libraries as the screening proceeded (FIG. 14).

Figure 15:
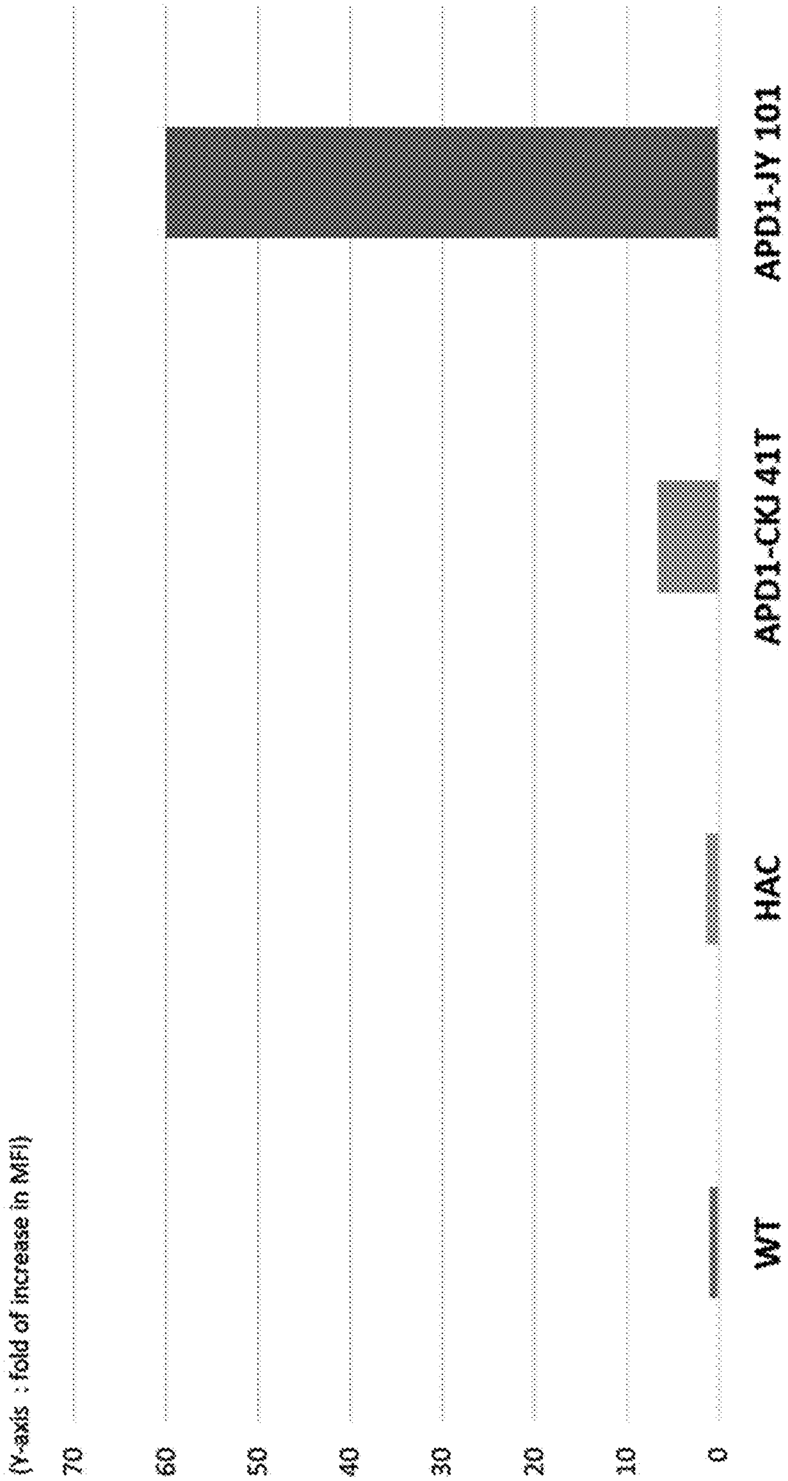
FIG. 15 shows a result of analyzing the binding affinity of *E. coli* cells displaying aglycosylated PD-1 variants screened through secondary screening to PD-L1.

Example 19. Securing of Additional PD-1 Variants Having Improved Binding Affinity to PD-L1 by Flow Cytometry Each of the single colonies from the final round (APD1-CKJ 41T: aglycosylated form of CKJ 41T, APD1-JY 101: aglycosylated form JY 101), wild-type PD-1 and HAC-V was inoculated to a TB medium containing 2% glucose and 40 μg/mL chloramphenicol and then cultured at 37° C. and 250 rpm for 16 hours. The cultured cells were inoculated again to 6 mL of a TB medium containing 40 μg/mL chloramphenicol by diluting to a ratio of 1:100. After culturing to $OD_{600}$=0.5, followed by cooling for 20 minutes at 25° C. and 250 rpm, the protein overexpression was induced at 25° C. and 250 rpm for 5 hours by adding 1 mM IPTG. The same quantity of the *E. coli* was added to an e-tube through $OD_{600}$ normalization and the cells were recovered through centrifugation at 14,000 rpm for 1 minute. After conducting spheroplasting in the same manner as described in Example 5, 4 nM of a tetrameric PD-L1-Alexa488 probe was added to the prepared spheroplasts and they were labeled with the fluorescent probe by rotating at room temperature. After conducting the labeling process for 1 hour, centrifugation was performed at 13,500 rpm for 1 minute. After discarding the supernatant, the cells were washed once with 1 mL of PBS and then centrifuged again at 13,500 rpm for 1 minute. The cells were resuspended in 1 mL of PBS and the binding affinity to PD-L1 was analyzed by measuring fluorescence signals using the Guava instrument (FIG. 15).

Example 20. Cloning of Variants for Comparing Mutation Sites of Screened PD-1 Variants It was investigated whether the introduction of novel mutation of CKJ 49 and 50 to LDSS affects binding affinity by cloning a PD-1_LDSS variant having overlapping mutations of CKJ 49 and CKJ 50. In order to prepare PD-1_LDSS, Quikchange PCR was conducted using a CKJ 49 vector as a template. For this, the gene was amplified using primers (JY#21, JY#22) and Pfu Turbo polymerase (Agilent). The amplified gene was transformed into Jude1 and then sequenced.

Figure 16:
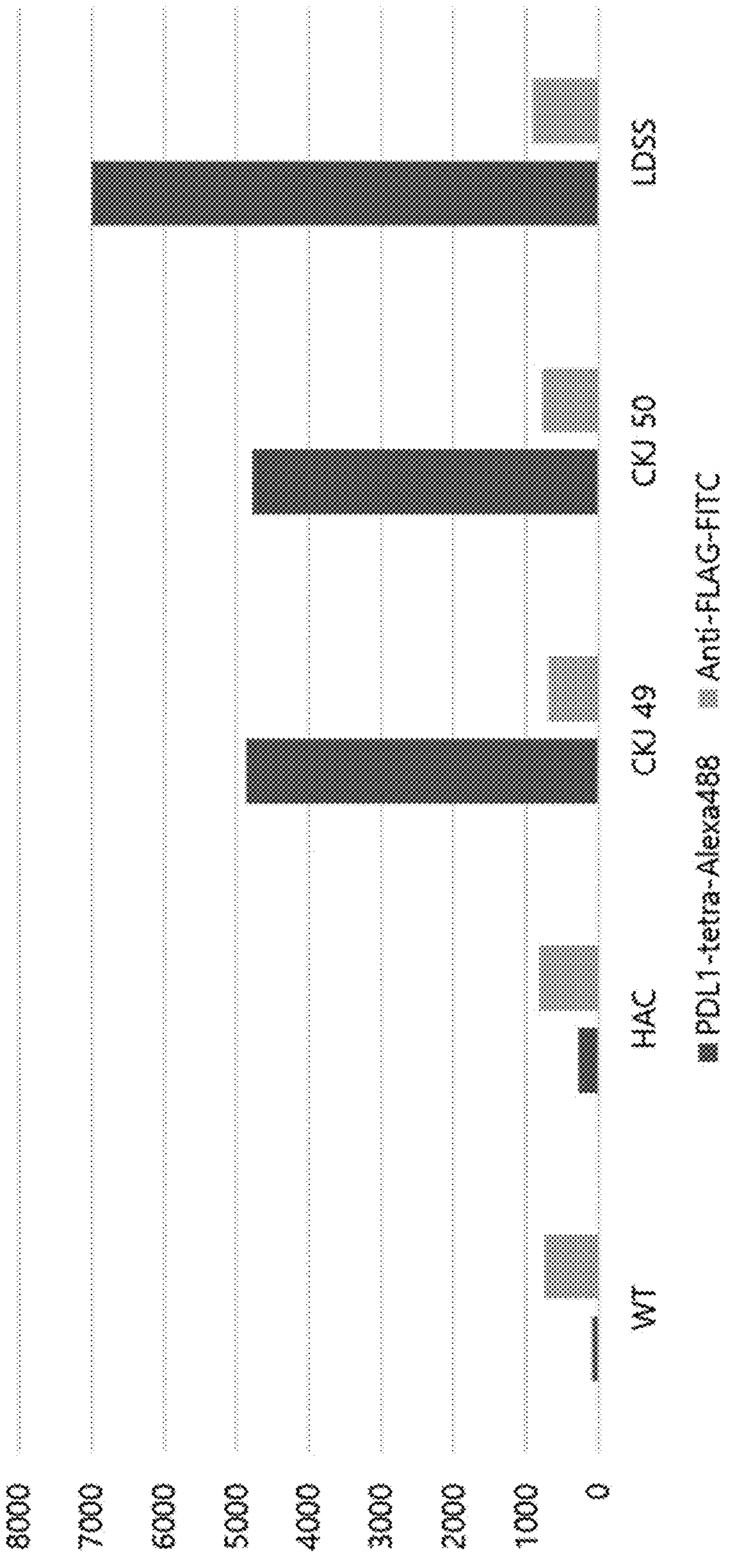
FIG. 16 shows a result of comparing the binding affinity of PD-1 variants and a consensus sequence variant to PD-L1.

Example 21. Comparison of Binding Affinity to PD-L1 Among PD-1 Variants by Flow Cytometry After inoculating each of wild-type PD-1, the HAC-V variant (control group) CKJ 49, CKJ 50 and LDSS to a TB medium containing 2% glucose and 40 μg/mL chloramphenicol, the cells were cultured at 37° C. and 250 rpm for 16 hours. The cultured cells were inoculated to 6 mL of a TB medium containing 40 μg/mL chloramphenicol by diluting to 1:100. After culturing to $OD_{600}$=0.5, followed by cooling for 20 minutes at 25° C. and 250 rpm, the protein overexpression was induced at 25° C. and 250 rpm for 5 hours by adding 1 mM IPTG. The same number of the *E. coli* was added to an e-tube through $OD_{600}$ normalization and the cells were recovered through centrifugation at 14,000 rpm for 1 minute. After conducting spheroplasting in the same manner as described in Example 5, 12.5 nM of a tetrameric PD-L1-Alexa488 probe was added to the prepared spheroplasts and rotated at room temperature for labeling. After conducting the labeling process for 1 hour, centrifugation was performed at 13,500 rpm for 1 minute. After discarding the supernatant, the cells were washed once with 1 mL of PBS and then centrifuged again at 13,500 rpm for 1 minute. The cells were resuspended in 1 mL of PBS and the binding affinity to PD-L1 was analyzed by measuring fluorescence signals using the Guava instrument (FIG. 16). In addition, because the expression level of the PD-1 protein displayed by *E. coli* can affect fluorescence intensity, the expression level of PD-1 was determined. For this, 300 μL of the *E. coli* remaining after resuspending in PBS was taken and 700 μL of PBS and 1 μL of anti-FLAG-FITC were added together and spheroplasts were labeled with the fluorescent probe by rotating at room temperature. After conducting the labeling process for 1 hour, centrifugation was performed at 13,500 rpm for 1 minute. After discarding the supernatant, the cells were washed once with 1 mL of PBS and then centrifuged again at 13,500 rpm for 1 minute. The cells were resuspended in 1 mL of PBS and the binding affinity to anti-FLAG-FITC was analyzed by measuring fluorescence signals by flow cytometry (FIG. 16).

TABLE 4

| SEQ ID | PD-1 variant | Location of PD-1 variant and substituted amino acids |
|---|---|---|
| SEQ ID NO 90 | CKJ 41T | S36P/C69T/L114P |
| SEQ ID NO 91 | CKJ 41Y | S36P/C69Y/L114P |
| SEQ ID NO 92 | CKJ 41G | S36P/C69G/L114P |
| SEQ ID NO 93 | CKJ 41A | S36P/C69A/L114P |
| SEQ ID NO 94 | JY101 | L1S, F13I, L17M, S36P, M46I, C69T, G79R, G100V, L114P, A139L |
| SEQ ID NO 95 | LDSS | F13L, N25D, C69S, N92S |

Additionally screened PD-1 variants with improved binding affinity to PD-L1

Figure 17:
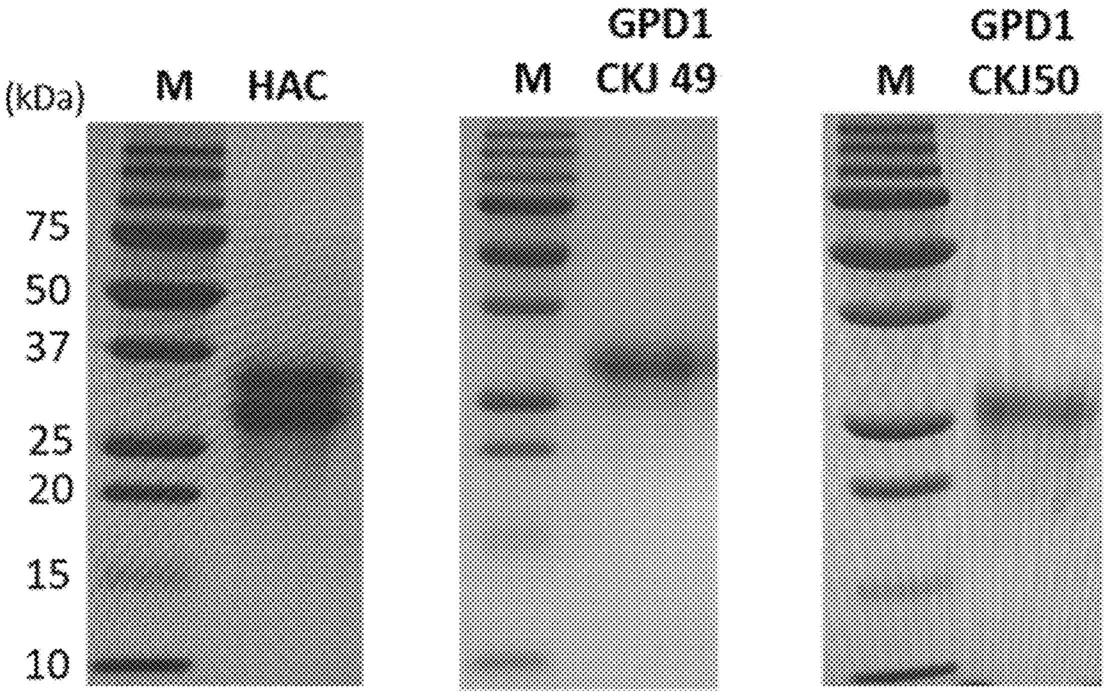
FIG. 17 shows the SDS-PAGE images of purified HAC-V and two PD-1 variant proteins.
Figure 18:
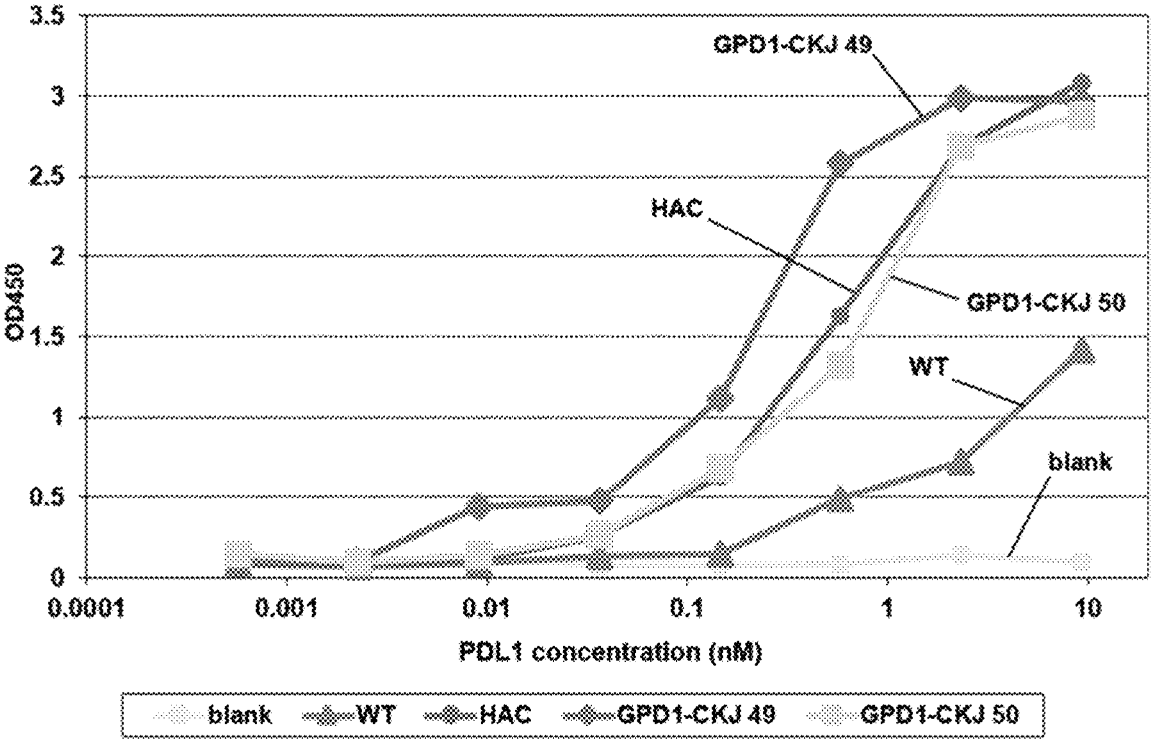
FIG. 18 shows a result of investigating the binding affinity of wild-type PD-1, HAC-V and two PD-1 variants to PD-L1.

Example 22. Expression of PD-1 Variants in Animal Cells, Purification and Verification of Binding Affinity In order to verify the binding affinity of PD-1 variants expressed in animal cells, the PD-1 variants were cloned into mammalian expression vector. The genes of HAC-V (control group) and the screened variants, CKJ 49 and CKJ50 were amplified by PCR using primers (CKJ#1, CKJ#2) and Vent polymerase. The amplified genes were treated with BssHII and XbaI enzymes were ligated into BssHII and XbaI fragment of pMaz vector. The sequence of the ligated plasmid was investigated by individual colony analysis by transforming into Jude1 *E. coli*. The prepared vector for expressing PD-1 glycovariants (pMaz-PD1 HAC-V-His tag, pMaz-PD1 CKJ 49-His tag, pMaz-PD1 CKJ 50-His tag)

were transfected into animal cells (HEK293F). After culturing the cells for 6 days, the cell culture was centrifuged at 6,000 rpm for 20 minutes and the supernatant was taken and filtered through a 0.22-μm filter. The filtered supernatant was applied to 1 mL of Ni-NTA resin (Qiagen) at 4° C. for 16 hours. The protein-bound resin was washed with 10 CV (column volume) of a PBS solution containing 10 mM imidazole (Sigma), and then washed again with 10 CV of a PBS solution containing 20 mM imidazole. Finally, an eluate was recovered with a PBS solution containing 250 mM imidazole (FIG. 17). The binding affinity of the wild-type PD-1, the control group and the two variants (GPD1-CKJ 49: glycosylated form of CKJ 49, GPD1-CKJ 50: glycosylated form of CKJ 50) to PD-L1 was investigated by ELISA. Each protein was diluted with 0.05 M $Na_2CO_3$ (pH 9.6, Junsei) to 200 ng/well and then bound to a high-binding 96-well plate (Costar) at 4° C. for 16 hours. After removing the protein, each 96-well plate was added by blocking solution (PBST (PBS containing 0.5% Tween 20) solution containing 5% skim milk) for 1 hour at room temperature. After discarding the upper solution and washing 4 times with 200 μL of a PBS solution containing 0.5% Tween 20, the PD-L1 tetramer was diluted with a PBS solution and then added to each 96-well plate for 1 hour at room temperature. After washing 4 times with 200 μL of a 0.5% PBST solution, anti-streptavidin-HRP (Genetex) diluted with PBS to 1:2,000 was added to each 96-well plate for 1 hour at room temperature. After discarding the upper solution and washing 4 times with 200 μL of a 0.5% PBST solution, reaction was initiated by adding 50 μL of TMB (Thermo Scientific) and was terminated 20 minutes after with 4 N $H_2SO_4$. As a result, it was confirmed that, although the glycosylation resulted in the change in binding affinity to PD-L1, CKJ 49 showed the best binding affinity (FIG. 18).

Although the specific embodiments of the present disclosure have been described in detail above, it is obvious to those of ordinary skill in the art that they are provided only as preferred exemplary embodiments and do not limit the scope of the present disclosure. Accordingly, the substantial scope of the present disclosure should be defined by the appended claims and their equivalents.

[National Research and Development Project Supporting the Present Disclosure]

[Project ID] 1711053534.

[Ministry in charge] Ministry of Science and ICT.

[R&D management agency] National Research Foundation of Korea.

[Research project name] Rising research supporting project.

[Research title] Development of protein therapeutic agent and bispecific antibody using antigen-binding aglycosylated Fc variant.

[Contribution factor] 1/2.

[Research agency] Kookmin University Industry-Academic Cooperation.

[Research period] 2017.06.01 to 2018.03.31.

[National Research and Development Project Supporting the Present Disclosure]

[Project ID] 1711058394.

[Ministry in charge] Ministry of Science and ICT.

[R&D management agency] National Research Foundation of Korea.

[Research project name] Management of new drug development pipeline.

[Research title] Identification of serum persistent Fc-based next-generation anticancer antibody targeting endothelin GPCR.

[Contribution factor] 1/2.

[Research agency] Kookmin University Industry-Academic Cooperation.

[Research period] 2017.06.30 to 2018.03.29.

The invention claimed is:

1. An immune checkpoint inhibitor that inhibits binding between wild-type PD-1 (programmed cell death protein 1) and PD-L1 (programmed death-ligand 1) consisting of a PD-1 variant having improved binding affinity to PD-L1 compared to wild-type PD-1, wherein the PD-1 variant is selected from the group consisting of the amino acid sequences set forth in SEQ ID NO: 52, SEQ ID NO: 53, and SEQ ID NO: 94.

2. The immune checkpoint inhibitor according to claim 1, wherein the PD-1 variant is an aglycosylated PD-1 variant.

3. A composition comprising the immune checkpoint inhibitor according to claim 1 as an active ingredient.

4. The composition according to claim 3, wherein the composition is a pharmaceutical composition for preventing or treating a cancer disease or an infectious disease.

5. An immune checkpoint inhibitor that inhibits binding between wild-type PD-1 (programmed cell death protein 1) and PD-L1 (programmed death-ligand 1) comprising a PD-1 variant having improved binding affinity to PD-L1 compared to wild-type PD-1, wherein the PD-1 variant has the amino acid sequence of SEQ ID NO: 49, 52, 53, 91, 92, 93, or 94.

6. The immune checkpoint inhibitor according to claim 5, wherein the PD-1 variant has the amino acid sequence of SEQ ID NO: 49.

7. The immune checkpoint inhibitor according to claim 5, wherein the PD-1 variant has the amino acid sequence of SEQ ID NO: 52.

8. The immune checkpoint inhibitor according to claim 5, wherein the PD-1 variant has the amino acid sequence of SEQ ID NO: 53.

9. The immune checkpoint inhibitor according to claim 5, wherein the PD-1 variant has the amino acid sequence of SEQ ID NO: 91.

10. The immune checkpoint inhibitor according to claim 5, wherein the PD-1 variant has the amino acid sequence of SEQ ID NO: 92.

11. The immune checkpoint inhibitor according to claim 5, wherein the PD-1 variant has the amino acid sequence of SEQ ID NO: 93.

12. The immune checkpoint inhibitor according to claim 5, wherein the PD-1 variant has the amino acid sequence of SEQ ID NO: 94.

13. A composition comprising the immune checkpoint inhibitor according to claim 12 as an active ingredient and an acceptable carrier.

14. The composition according to claim 13, wherein the composition is a pharmaceutical composition for preventing or treating a cancer disease or an infectious disease comprising a pharmaceutically acceptable carrier.

* * * * *